United States Patent
Cuny et al.

(10) Patent No.: US 11,174,255 B2
(45) Date of Patent: Nov. 16, 2021

(54) PYRIDO[2,3-D]PYRIMIDIN-7-ONES AND RELATED COMPOUNDS AS INHIBITORS OF PROTEIN KINASES

(71) Applicants: UNIVERSITY OF HOUSTON SYSTEM, Houston, TX (US); TRUSTEES OF TUFTS COLLEGE, Medford, MA (US)

(72) Inventors: Gregory Cuny, Houston, TX (US); Sameer Nikhar, Houston, TX (US); Alexei Degterev, Brookline, MA (US)

(73) Assignees: UNIVERSITY OF HOUSTON SYSTEM, Houston, TX (US); TRUSTEES OF TUFTS COLLEGE, Medford, MA (US)

( * ) Notice: Subject to any disclaimer, the term of this patent is extended or adjusted under 35 U.S.C. 154(b) by 0 days.

(21) Appl. No.: 16/613,003

(22) PCT Filed: May 15, 2018

(86) PCT No.: PCT/US2018/032631
§ 371 (c)(1),
(2) Date: Nov. 12, 2019

(87) PCT Pub. No.: WO2018/213219
PCT Pub. Date: Nov. 22, 2018

(65) Prior Publication Data
US 2020/0172536 A1   Jun. 4, 2020

Related U.S. Application Data

(60) Provisional application No. 62/506,394, filed on May 15, 2017.

(51) Int. Cl.
| | | |
|---|---|---|
| *A61K 31/4375* | (2006.01) | |
| *A61K 31/472* | (2006.01) | |
| *A61K 31/4725* | (2006.01) | |
| *A61K 31/517* | (2006.01) | |
| *A61K 31/519* | (2006.01) | |
| *A61P 9/00* | (2006.01) | |
| *A61P 35/00* | (2006.01) | |
| *A61P 37/00* | (2006.01) | |
| *C07D 217/22* | (2006.01) | |
| *C07D 401/12* | (2006.01) | |
| *C07D 401/14* | (2006.01) | |
| *C07D 403/12* | (2006.01) | |
| *C07D 403/14* | (2006.01) | |
| *C07D 471/04* | (2006.01) | |

(52) U.S. Cl.
CPC .................. *C07D 471/04* (2013.01)

(58) Field of Classification Search
CPC .............. A61K 31/4375; A61K 31/472; A61K 31/4725; A61K 31/517; A61K 31/519; A61P 19/00; A61P 35/00; A61P 37/00; C07D 217/22; C07D 401/12; C07D 401/14; C07D 403/12; C07D 403/14; C07D 471/04

See application file for complete search history.

(56) References Cited

U.S. PATENT DOCUMENTS

| | | | | |
|---|---|---|---|---|
| 5,733,914 | A * | 3/1998 | Blankley | C07D 471/04 |
| | | | | 514/264.1 |
| 8,674,095 | B2 * | 3/2014 | Campbell | A61P 25/18 |
| | | | | 544/279 |
| 9,663,524 | B2 * | 5/2017 | D'Agostino | A61P 1/00 |
| 2013/0252967 | A1 * | 9/2013 | Campbell | A61P 25/28 |
| | | | | 514/252.16 |

FOREIGN PATENT DOCUMENTS

| | | |
|---|---|---|
| WO | 96/34867 | 11/1996 |
| WO | 99/09030 | 2/1999 |

(Continued)

OTHER PUBLICATIONS

Boschelli et al., Synthesis and Tyrosine Kinase Inhibitory Activity of a Series of 2-Amino-8H-pyrido[2,3-d]pyrimidines: Identification of Potent, Selective Platelet-Derived Growth Factor Receptor Tyrosine Kinase Inhibitors, Journal of Medicinal Chemistry, vol. 41, No. 22, pp. 4365-4377 (Year: 1998).*

(Continued)

*Primary Examiner* — Brenda L Coleman
(74) *Attorney, Agent, or Firm* — Jackson Walker LLP

(57) ABSTRACT

Identified compounds demonstrate protein kinase inhibitory activity. More specifically, the compounds having the structures below (I) are demonstrated to inhibit receptor interacting kinase 2 (RIPK2) and/or Activin-like kinase 2 (ALK2). Compounds that are either dual RIPK2/ALK2 inhibitors or that preferentially inhibit RIPK2 or ALK2 could provide therapeutic benefit.

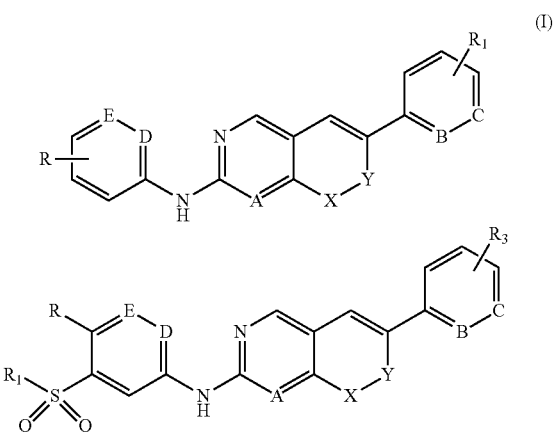

9 Claims, 23 Drawing Sheets

(56) References Cited

FOREIGN PATENT DOCUMENTS

| WO | 2005/034869 | 4/2005 |
|---|---|---|
| WO | 2011/156646 | 12/2011 |
| WO | 2012/122011 | 9/2012 |

OTHER PUBLICATIONS

Diller et al., Kinases, Homology Models, and High Throughput Docking, Journal of Medicinal Chemistry, vol. 46, No. 22, pp. 4638-4647 (Year: 2003).*

Hare et al., CORES: An Automated Method for Generating Three-Dimensional Models of Protein/Ligand Complexes, Journal of Medicinal Chemistry, vol. 47, No. 19, pp. 4731-4740 (Year: 2004).*

Licciulli et al., FRAX597, a Small Molecule Inhibitor of the p21-activated Kinases, Inhibits Tumorigenesis of Neurofibromatosis Type 2 (NF2)-associated Schwannomas, The Journal of Biological Chemistry, vol. 288, No. 40, pp. 29105-29114 (Year: 2013).*

Palmer et al., Structure-activity relationships for 2-anilino-6-phenylpyrido[2,3-d]pyrimidin-7(8H)-ones as inhibitors of the cellular checkpoint kinase Wee1, Bioorganic & Medicinal Chemistry Letters, vol. 15, No. 7, pp. 1931-1935 (Year: 2005).*

Notification of Transmittal of the International Search Report and Written Opinion of the International Search Authority—The European Patent Office—dated Sep. 13, 2019 for International Application No. PCT/US2018/032631, 18 pages.

Klutchko, et al., "2-Substituted Aminopyrido[2,3-d]pyrimidin-7(8H)-ones. Structure-Activity Relationships Against Selected Tyrosine Kinases and in Vitro and in Vivo Anticancer Activity", J. Med. Chem., 1998, 41, pp. 3276-3292.

Caballero, et al., "2D Autocorrelation, CoMFA, and CoMSIA modeling of protein tyrosine kinases' inhibition by substituted pyrido[2,3-d]pyrimidine derivatives", Bioorganic & Medicinal Chemistry, 2008, 16, pp. 810-821.

Canning, et al., "Inflammatory Signaling by NOD-RIPK2 is Inhibited by Clinically Relevant Type II Kinase Inhibitors", Chemistry & Biology, 2015, 22, pp. 1174-1184.

Notification of Transmittal of the International Preliminary Report on Patentability from the International Bureau of WIPO dated Nov. 28, 2019 for International Application No. PCT/US2018/032631, 9 pages.

* cited by examiner

13i = R₁ = phenyl; R₂ = -CH₂CH₃
13j = R₁ = phenyl; R₂ = -CH₂CH₂OH
13k = R₁ = 2,6-di Cl phenyl; R₂ = -CH₂CH₂OCH₃
13l = R₁ = 2,6-di Cl phenyl; R₂ = -benzyl
13m = R₁ = 2,6-di Cl phenyl; R₂ = -isobutyl
13n = R₁ = 4-Cl phenyl; R₂ = -isobutyl
13q = R₁ = 2,6-di Cl phenyl; R₂ = 3-methylsulfonyl benzyl
13r = R₁ = 2,6-di Cl phenyl; R₂ = 4-methylsulfonyl benzyl

PYRIDO[2,3-D]PYRIMIDIN-7-ONES AND RELATED COMPOUNDS AS INHIBITORS OF PROTEIN KINASES

BACKGROUND

This application claims priority to U.S. Provisional Patent Application No. 62/506,394, filed May 15, 2017, entitled "Pyridol[2,3-d]pyrimidin-7-ones and Related Compounds as Inhibitors of Protein Kinases," the entire contents of which are hereby incorporated by reference.

This disclosure pertains to compounds that demonstrate protein kinase inhibitory activity.

Protein kinases are important enzymes in cellular signal transduction. In many pathological conditions aberrant signal transduction occurs. Therefore, protein kinase inhibitors can be used as therapeutic agents for the treatment of various diseases.

This invention was made with government support under grant CA190542 awarded by the National Institutes of Health. The government has certain rights in the invention.

SUMMARY

The present disclosure relates generally to compounds that demonstrate protein kinase inhibitory activity. More specifically, the compounds can inhibit receptor interacting kinase 2 (RIPK2) and/or Activin-like kinase 2 (ALK2). RIPK2 mediates pro-inflammatory signaling and is an emerging therapeutic target in autoimmune and inflammatory diseases, such as inflammatory bowel disease (IBD) and multiple sclerosis. RIPK2 inhibitors could provide therapeutic benefit in the treatment of these and other conditions. Activin-like kinase 2 (ALK2) has been implicated in a number of diseases, such as bone disease (e.g. fibrodysplasia ossificans progressiva, ankylosing spondylitis), cardiovascular diseases (e.g. atherosclerosis and vascular calcification), some cancers (e.g. diffuse intrinsic pontine gliomas) and burns. Many of these maladies also have an inflammatory component that could exacerbate the condition and/or worsen the clinical outcome. Compounds that are either dual RIPK2/ALK2 inhibitors or that preferentially inhibit RIPK2 or ALK2 could provide therapeutic benefit in the treatment of these and other conditions.

DETAILED DESCRIPTION OF PREFERRED EMBODIMENTS

The present disclosure relates to protein kinase inhibitors and uses thereof.

The following figure depicts general structures of preferred embodiments of compounds that inhibit protein kinases, including RIPK2 and/or ALK2.

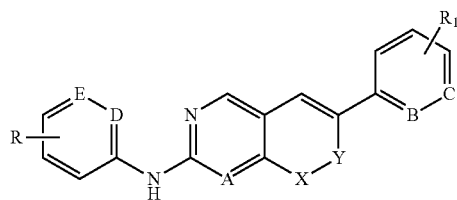

In the above structure, R can be H, or R can be a substituent on any one available position of the phenyl ring that is SO₂Me,

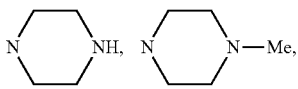

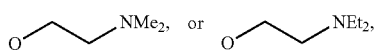

where Me is methyl and Et is ethyl. A and D can independently be N or CH. E can be N, CH, or C—R, with R defined as above. B and C can independently be N, CH, or C—Cl. $R_1$ can be H, or $R_1$ can be C—Cl, C—F, C—OCH₃, C—C(CH₃)₃, or C—OH at any one available position of the ring. X—Y can be C=C, or they can be

where $R_2$ is H, alkyl, including but not limited to methyl, ethyl or isobutyl, alkylhydroxyl, including but not limited to 2-hydroxyethyl, alkylalkoxyl, including but not limited to 2-methoxyethyl, or alkylaryl, including but not limited to benzyl or phenethyl.

The following figure depicts a general structure of additional preferred embodiments of compounds that inhibit protein kinases, including RIPK2 and/or ALK2.

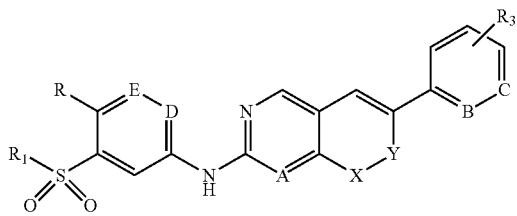

In the above structure, A and D can independently be N or CH. E can be N, CH, or C—R. B and C can independently be N, CH, or C—Cl. X—Y can be C=C, or they can be

where $R_2$ is H, alkyl, including but not limited to methyl, ethyl or isobutyl, alkylhydroxyl, including but not limited to 2-hydroxyethyl, alkylalkoxyl, including but not limited to 2-methoxyethyl, or alkylaryl, including but not limited to benzyl or phenethyl. R can be H.

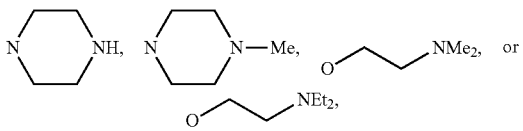

where Me is methyl and Et is ethyl. $R_1$ can be any alkyl group, including but not limited to methyl, ethyl, or propyl, or $R_1$ can be any aryl group, including but not limited to naphthyl, thienyl, indoyl, and the like. $R_3$ can be H, or $R_3$ can be C—Cl, C—F, C—OCH₃, C—C(CH₃)₃, or C—OH at any one available position of the ring.

The exemplary compounds that inhibit protein kinases described herein may occur in different geometric and enantiomeric forms, and both pure forms and mixtures of these separate isomers are included in the scope of this invention, as well as any physiologically functional or pharmacologically acceptable salt derivatives or prodrugs thereof. Production of these alternate forms would be well within the capabilities of one skilled in the art.

Figure 13:
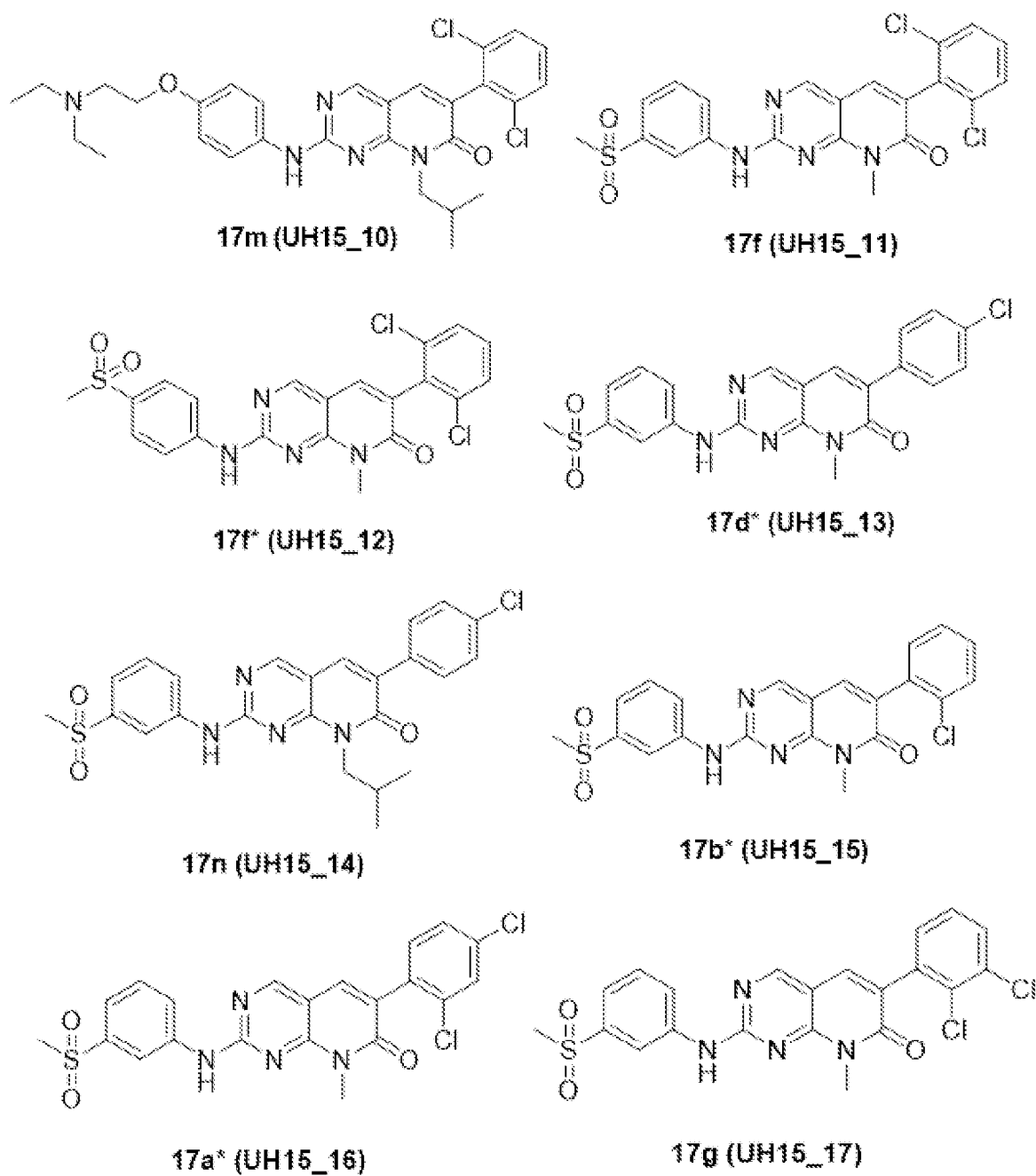
FIG. 13 shows structures for exemplary inhibitors of protein kinase, in accordance with preferred embodiments.
Figure 14:
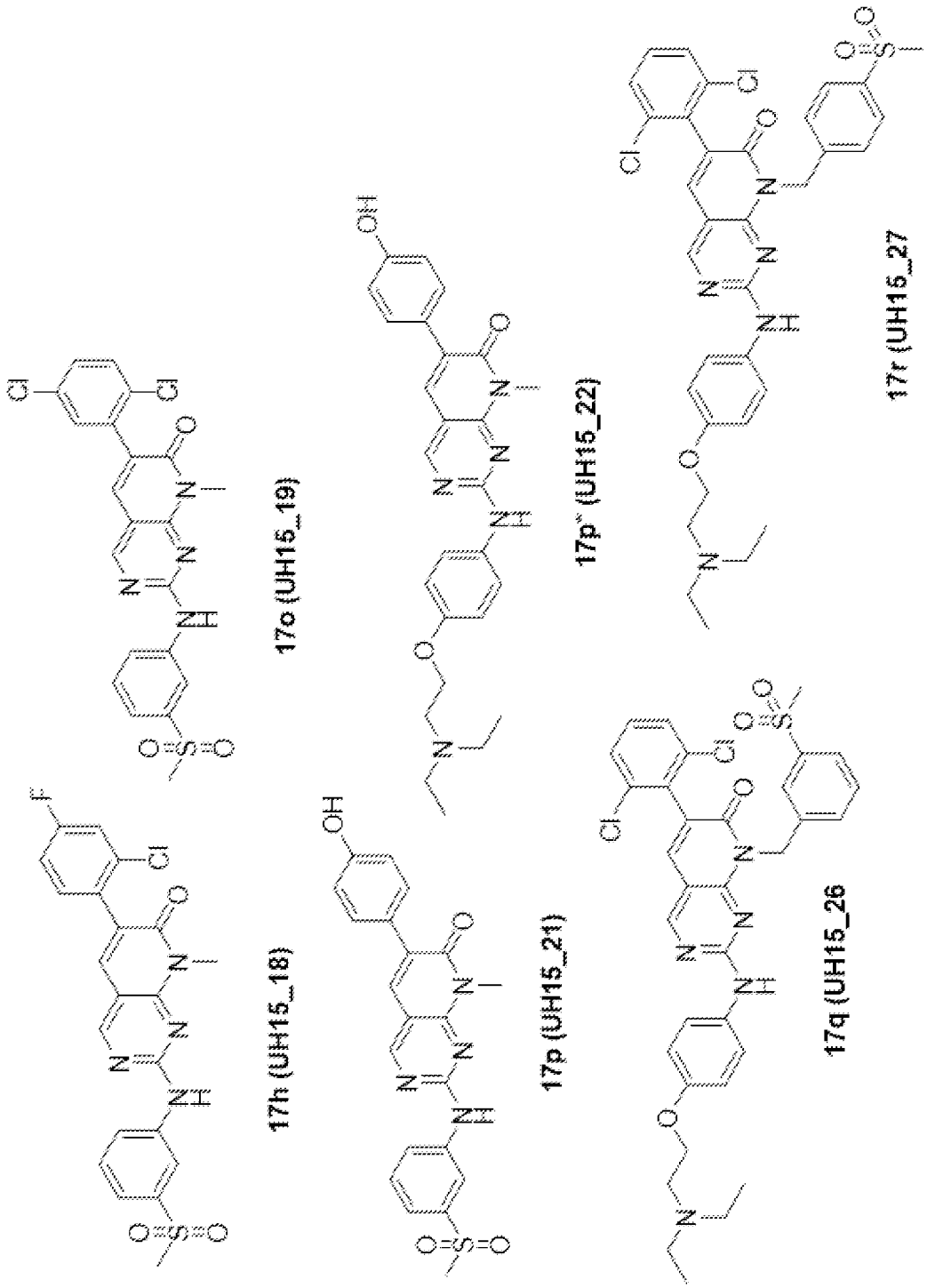
FIG. 14 shows structures for exemplary inhibitors of protein kinase, in accordance with preferred embodiments.
Figure 15:
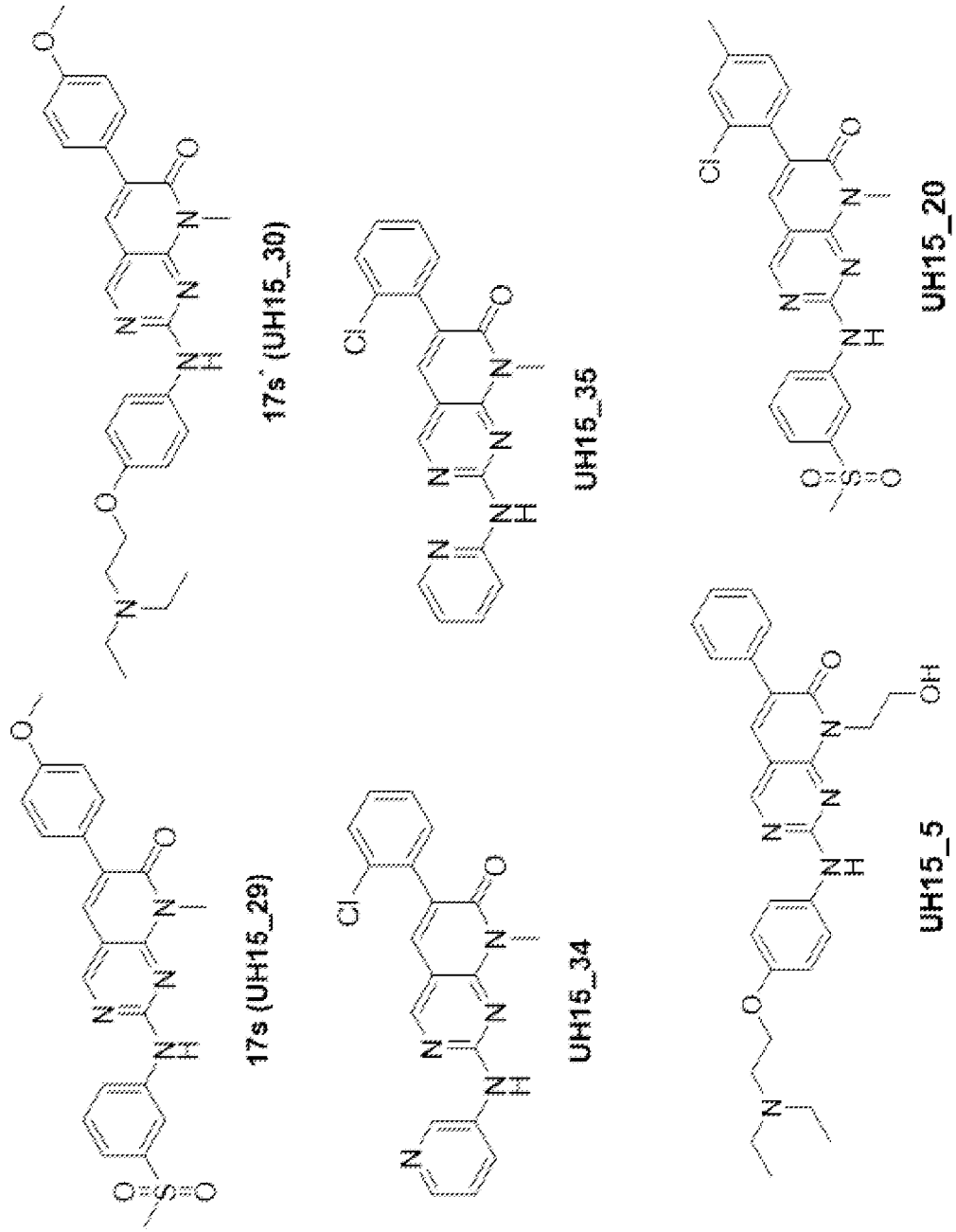
FIG. 15 shows structures for exemplary inhibitors of protein kinase, in accordance with preferred embodiments.

The current invention also pertains to methods of prevention or therapy for diseases involving protein kinase activity, including the step of administering a compound that inhibits protein kinase activity in accordance with preferred embodiments disclosed herein. In preferred embodiments, the methods of prevention or therapy for diseases involving protein kinase activity include the step of administering a compound that is compound 17d* (UH15_15), shown in FIG. 13, compound 61 (UH15_25), shown in FIG. 21, compound 57 (UH15_32), shown in FIG. 16, compound 59 (UH15_33), shown in FIG. 17, or compound UH15_34, shown in FIG. 15.

In another aspect of the present invention there is provided a pharmaceutical composition including a therapeutically effective amount of a compound that inhibits protein kinase as defined above and a pharmaceutically acceptable excipient, adjuvant, carrier, buffer or stabiliser. A "therapeutically effective amount" is to be understood as an amount of an exemplary protein kinase inhibitor compound that is sufficient to show inhibitory effects on protein kinase activity. The actual amount, rate and time-course of administration will depend on the nature and severity of the disease being treated. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral, or by injection, such as cutaneous, subcutaneous, or intravenous injection, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as sodium chloride solution, Ringer's solution, or lactated Ringer's solution. Preservatives, stabilisers, buffers, antioxidants and/or other additives may be included as required.

In another aspect, there is provided the use in the manufacture of a medicament of a therapeutically effective amount of protein kinase inhibitor compound as defined above for administration to a subject.

The term "pharmacologically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like, and potassium carbonate, sodium or potassium hydroxide, ammonia, triethylamine, triethanolamine and the like.

The term "prodrug" means a pharmacological substance that is administered in an inactive, or significantly less active, form. Once administered, the prodrug is metabolised in vivo into an active metabolite.

The term "therapeutically effective amount" means a nontoxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.

Further aspects of the present invention will become apparent from the following description given by way of example only and with reference to the accompanying synthetic schemes.

Figure 1:
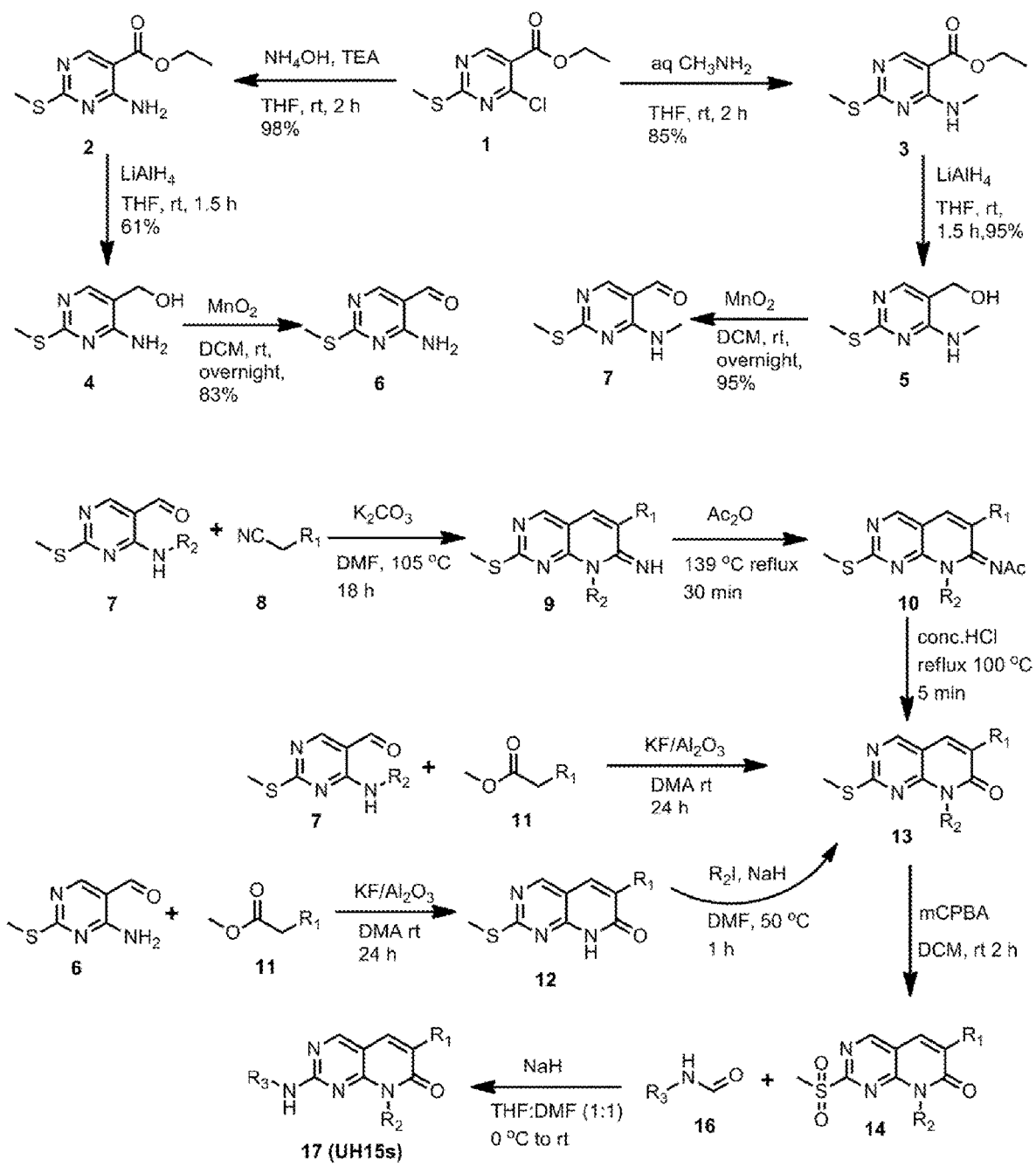
FIG. 1 shows a general overall synthetic scheme for compounds disclosed herein as inhibitors of protein kinases, in accordance with preferred embodiments.
Figure 2:
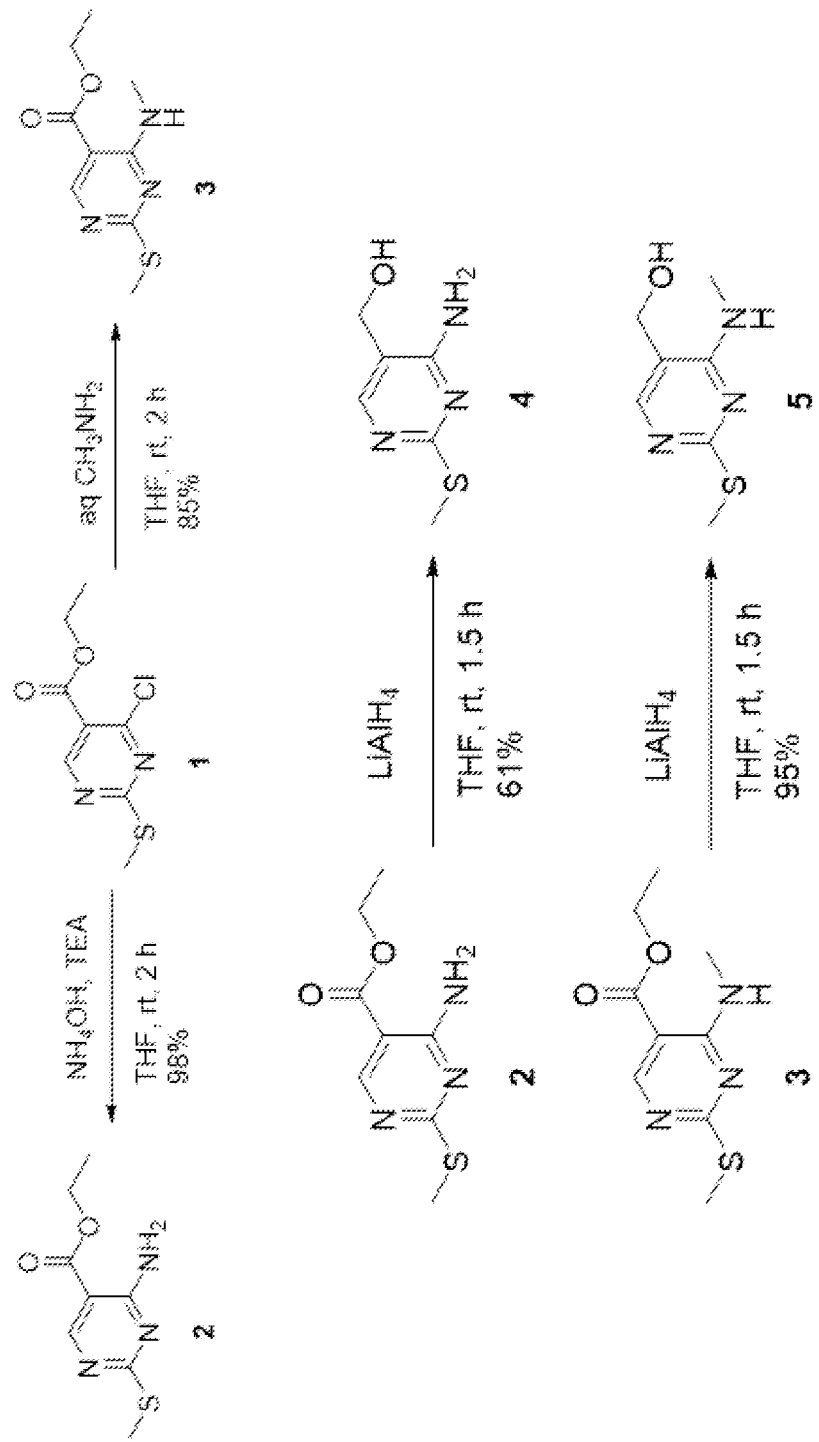
FIG. 2 shows synthetic schemes for intermediate compounds used in the synthesis of exemplary inhibitors of protein kinase.
Figure 3:
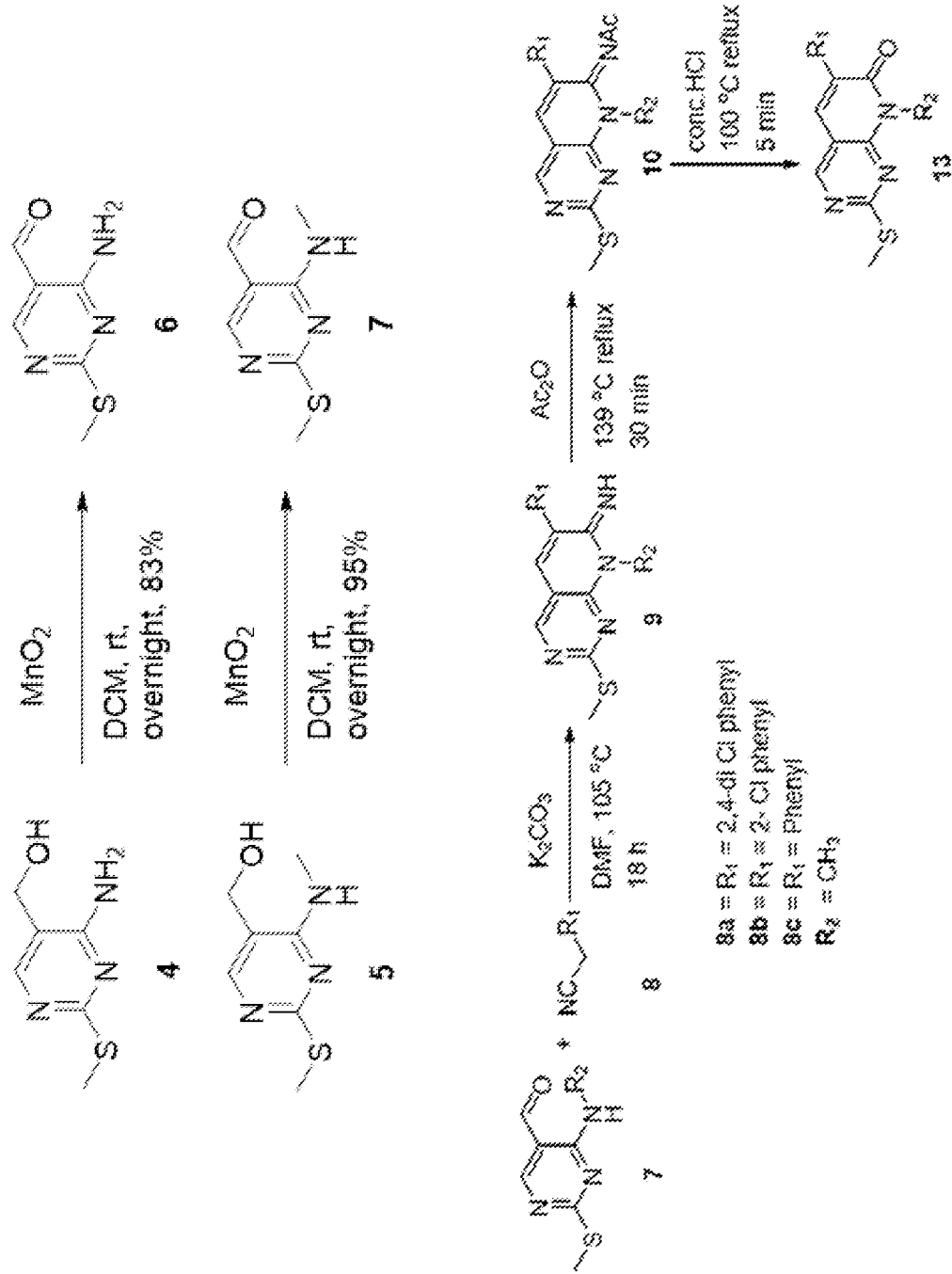
FIG. 3 shows synthetic schemes for intermediate compounds used in the synthesis of exemplary inhibitors of protein kinase.
Figure 4:
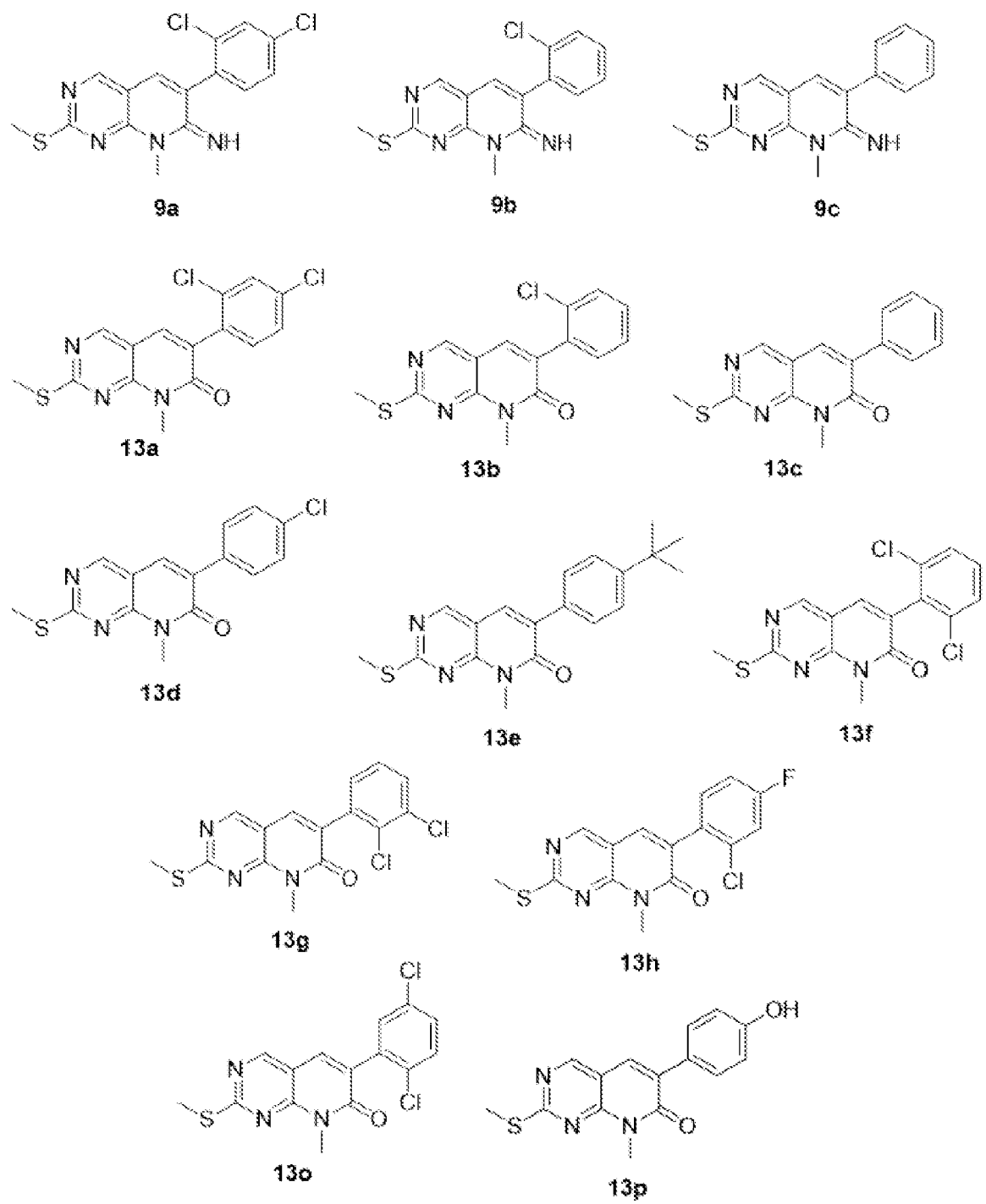
FIG. 4 shows the structures of intermediate compounds used in the synthesis of exemplary inhibitors of protein kinase.
Figure 5:
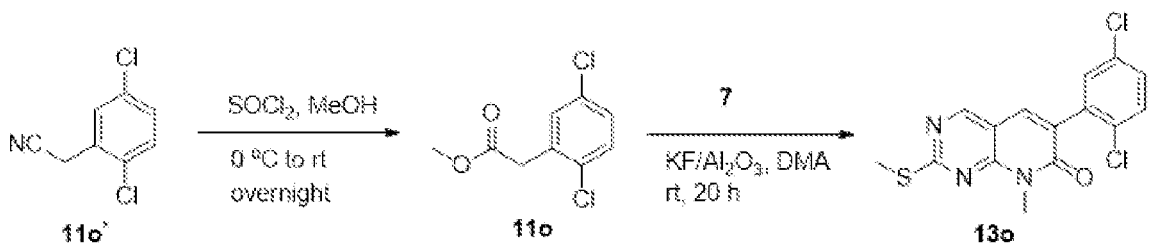
FIG. 5 shows synthetic schemes for intermediate compounds used in the synthesis of exemplary inhibitors of protein kinase.
Figure 5:
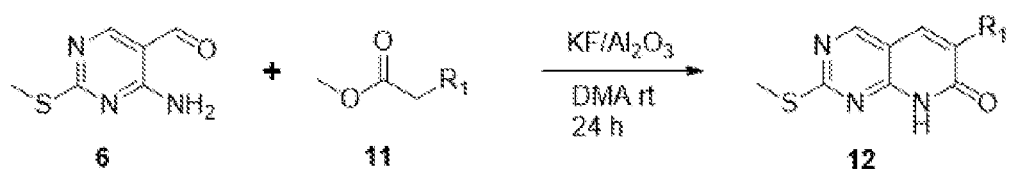
Figure 5:
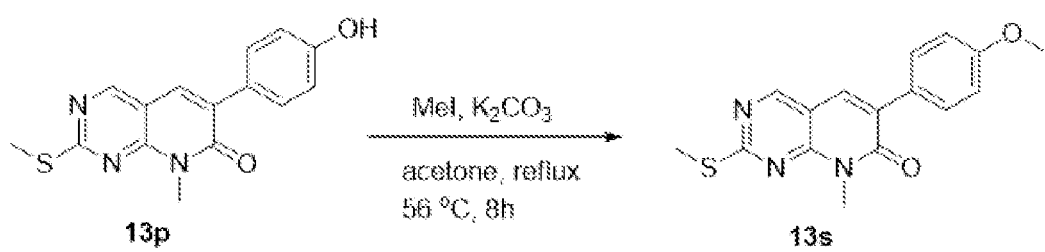
Figure 5:
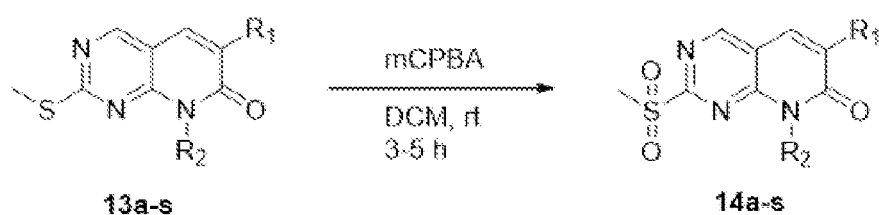
Figure 6:
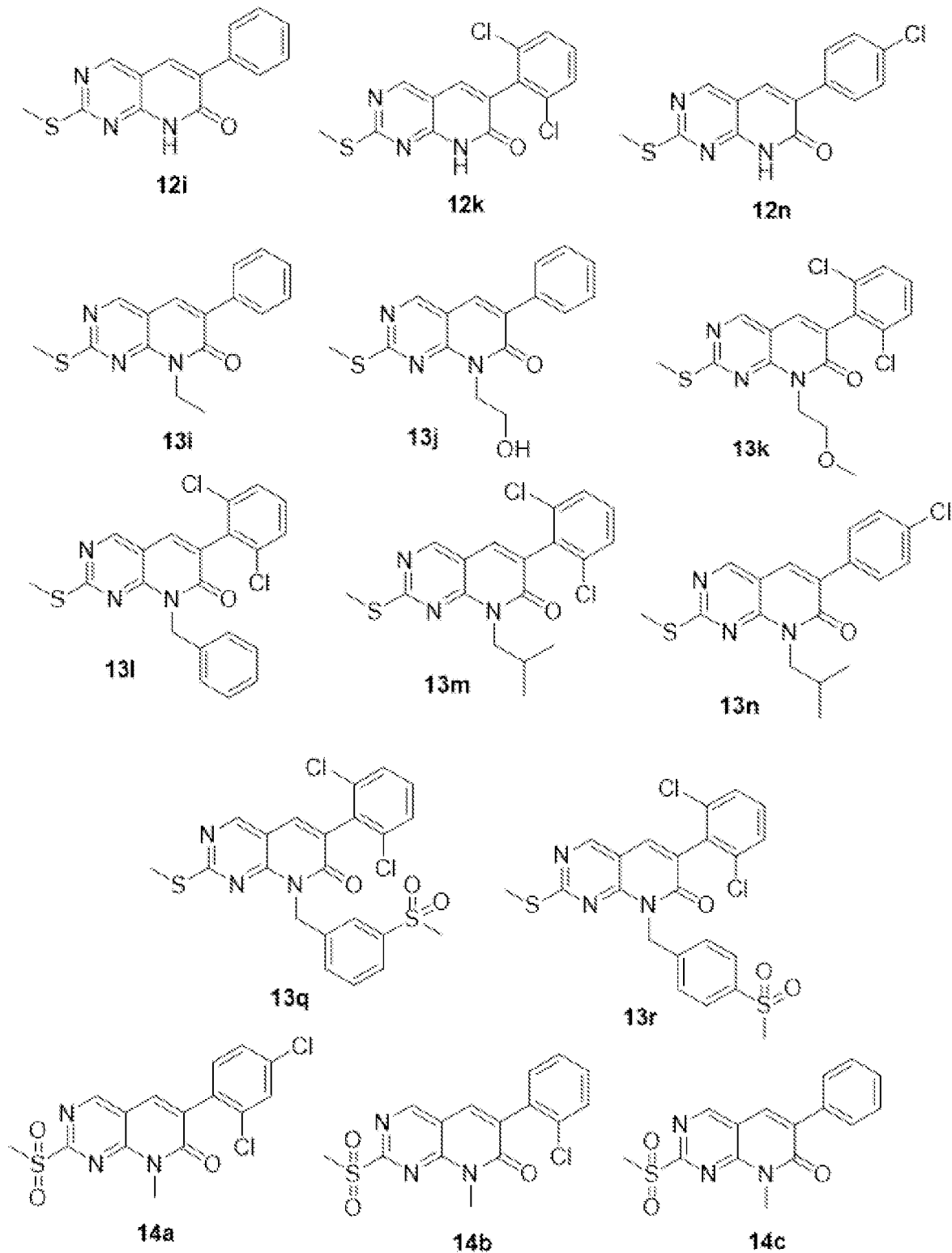
FIG. 6 shows the structures of intermediate compounds used in the synthesis of exemplary inhibitors of protein kinase.
Figure 7:
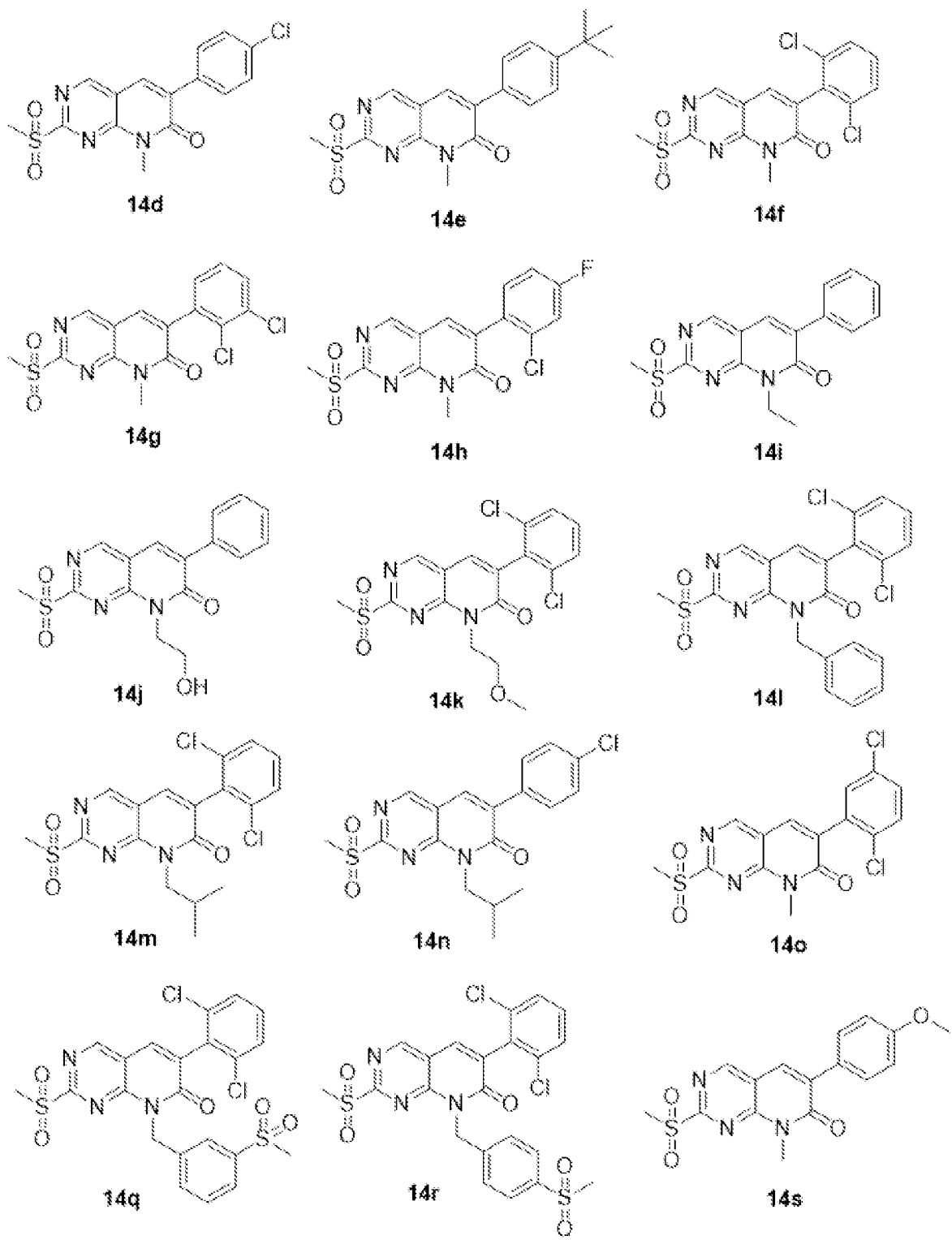
FIG. 7 shows the structures of intermediate compounds used in the synthesis of exemplary inhibitors of protein kinase.
Figure 8:
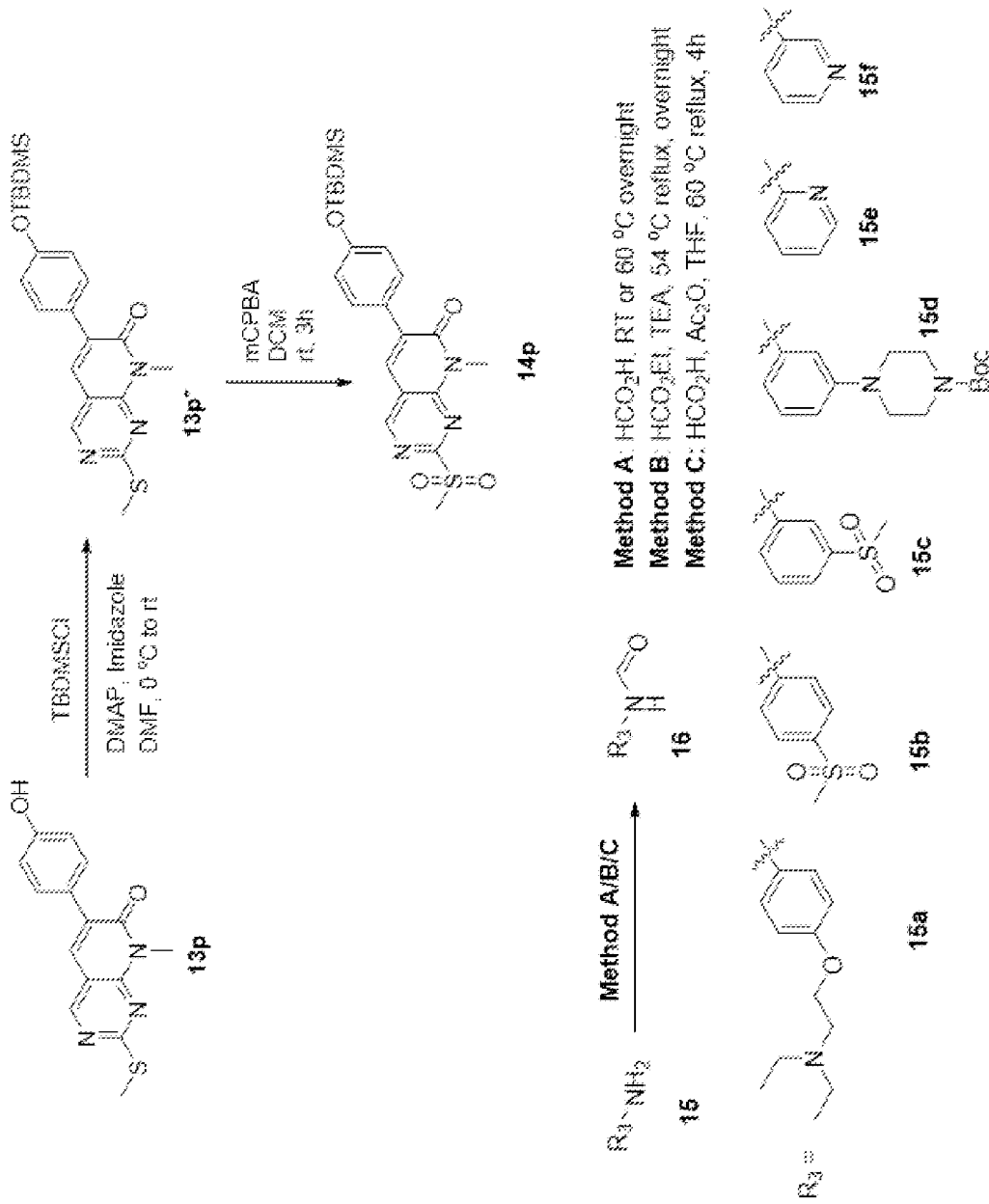
FIG. 8 shows synthetic schemes for intermediate compounds used in the synthesis of exemplary inhibitors of protein kinase.
Figure 9:
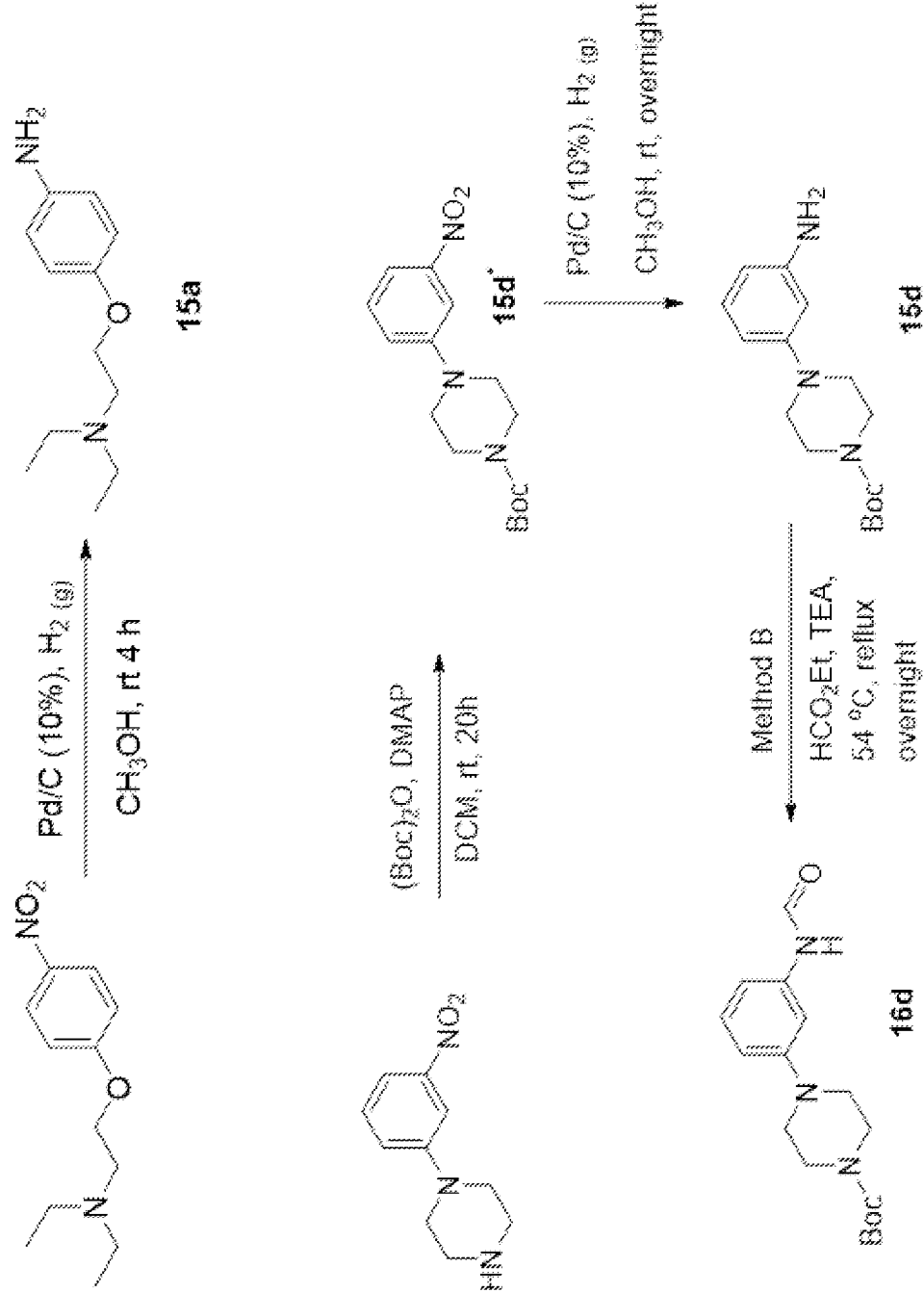
FIG. 9 shows synthetic schemes for intermediate compounds used in the synthesis of exemplary inhibitors of protein kinase.
Figure 10:
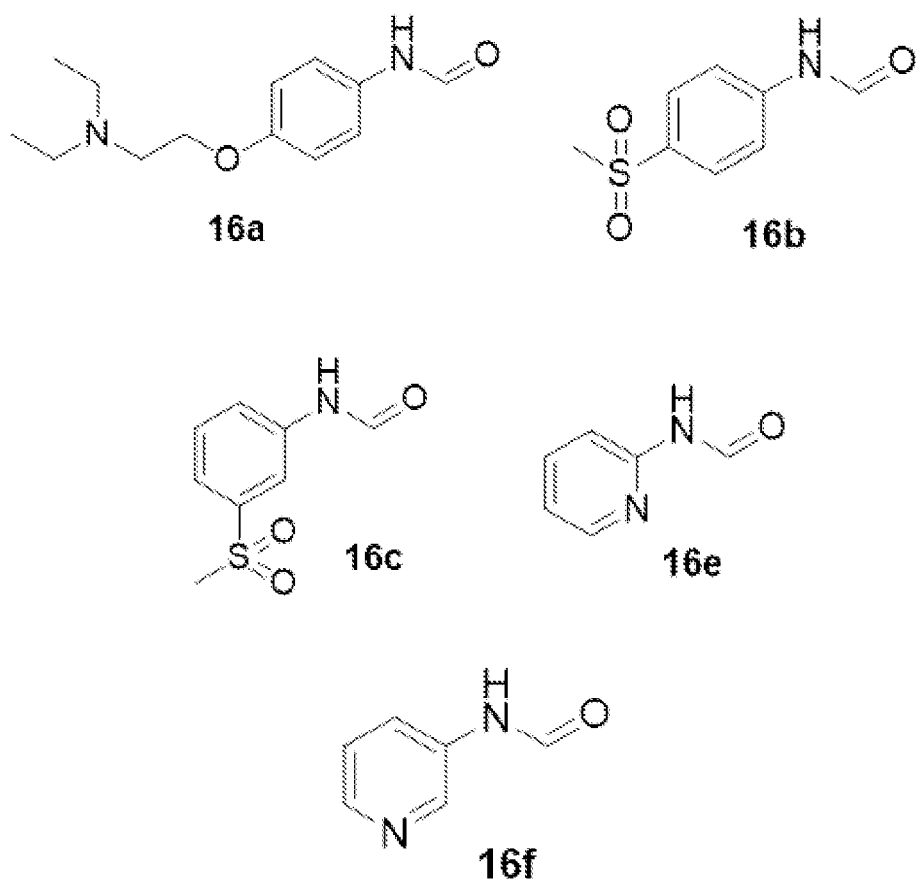
FIG. 10 shows the structures of intermediate compounds used in the synthesis of exemplary inhibitors of protein kinase.

FIG. 1 shows a general overall synthetic scheme for exemplary compounds disclosed herein as inhibitors of protein kinases, referred to generally as UH15 analogs, or UH15s.

EXAMPLES

All reactions were carried out under argon atmosphere with dry solvents under anhydrous conditions, unless otherwise stated. All commercially available chemicals and reagent grade solvents were used directly without further purification unless otherwise specified. Reactions were monitored by thin-layer chromatography (TLC) on Bakerflex® silica gel plates (IB2-F) using UV-light (254 and 365 nm) as visualizing agent and either ethanolic solution of phosphomolybdic acid or ninhydrin solution and heat as developing agents. Flash chromatography was conducted on silica gel (230-400 mesh) using Teledyne ISCO CombiFlash® Rf. NMR spectra were recorded at room temperature using a JEOL ECA-500 (1H NMR and 13C NMR at 400, 500 and 600 MHz) with tetramethylsilane (TMS) as an internal standard. Chemical shifts (δ) are given in parts per million (ppm) with reference to solvent signals [1H-NMR: CDCl$_3$ (7.26 ppm), CD$_3$OD (3.30 ppm), DMSO-d6 (2.49 ppm); 13C-NMR: CDCl$_3$ (77.0 ppm), CD$_3$OD (49.0 ppm), DMSO-d6 (39.5 ppm)]. Signal patterns are reported as s (singlet), d (doublet), t (triplet), q (quartet), dd (doublet of doublets), td (triplet of doublets), m (multiplet) and brs (broad singlet). Coupling constants (J) are given in Hz. High resolution mass spectra (HRMS) were carried out using Agilent 6530 Q-TOF instrument by Mass spectrometry facility at Department of Chemistry, the University of Texas at Austin. Electrospray ionization (ESI) were used as ionization source and the spectra were reported as m/z (relative intensity) for the molecular [M] or [M+H]$^+$ ion species. Purity of compounds were determined by high-performance liquid chromatography (HPLC) analyses using binary hplc pump (Waters) and Kinetex 5 um C18 100A column (250× 4.6 mm). UV absorption was monitored at λ=254 nm. The injection volume was 15 µL. The HPLC gradient went from 2% acetonitrile/98% water to 90% acetonitrile/10% water (both solvents contain 0.1% trifluoroacetic acid) with a total run time of 30 min and flow rate of 1 mL/min.

Example 1

Synthesis

FIGS. 2-3, 5, and 8-9 show synthetic schemes for intermediate compounds used in the synthesis of exemplary inhibitors of protein kinase, in accordance with preferred embodiments. FIGS. 4, 6-7, and 10 show structures for intermediate compounds used in the synthesis of exemplary inhibitors of protein kinase, in accordance with preferred embodiments.

Ethyl 4-amino-2-(methylthio)pyrimidine-5-carboxylate (2):

To a solution of ethyl 4-chloro-2-(methylthio)pyrimidine-5-carboxylate (1) (100 mg, 0.43 mmol) in dry THF (2 mL) was added triethylamine (0.2 mL, 1.29 mmol) and ammonium hydroxide (0.5 mL). The resulting mixture was stirred at rt for 2 h till completion. After evaporation in vacuo to remove THF, the crude mixture then partitioned between H$_2$O and EtOAc. The organic layer was washed with brine, dried over anhydrous Na$_2$SO$_4$, filtered and concentrated. The residue was purified by column chromatography on silica gel (15% EtOAc/hexane) to afford 2 (90 mg, 98%) as white solid. $^1$H NMR (400 MHz, CDCl$_3$) δ (ppm) 8.65 (s, 1H), 7.81 (s, 1H), 6.05 (s, 1H), 4.29 (q, J=7.2 Hz, 2H), 2.46 (s, 3H), 1.32 (t, J=7.1 Hz, 3H). $^{13}$C NMR (100 MHz, CDCl$_3$) δ 176.06, 166.42, 161.87, 158.93, 101.15, 61.02, 14.32, 14.14.

Ethyl 4-(methylamino)-2-(methylthio)pyrimidine-5-carboxylate (3):

To a solution of ethyl 4-chloro-2-(methylthio)pyrimidine-5-carboxylate (1) (3000 mg, 12.93 mmol) in dry THF (20 mL) was added aqueous (aq) methyl amine (6 mL). The resulting mixture was stirred at rt for 2 h till completion. After evaporation in vacuo to remove THF, the crude mixture then partitioned between H$_2$O and EtOAc. The organic layer was washed with brine, dried over anhydrous Na$_2$SO$_4$, filtered and concentrated. The residue was purified by column chromatography on silica gel (10% EtOAc/hexane) to afford 3 (2500 mg, 85%) as white solid. $^1$H NMR (400 MHz, CDCl$_3$) δ (ppm) 8.59 (s, 1H), 8.16 (s, 1H), 4.29 (q, J=7.0 Hz, 2H), 3.06 (d, J=5.0 Hz, 3H), 2.53 (s, 3H), 1.35 (t, J=7.1 Hz, 3H). $^{13}$C NMR (100 MHz, CDCl$_3$) δ 176.10, 167.13, 160.77, 158.25, 101.03, 60.88, 27.37, 14.34, 14.29.

(4-amino-2-(methylthio)pyrimidin-5-yl)methanol (4):

The suspension of LiAlH$_4$ (120 mg, 3.16 mmol) in THF (4 mL) was cooled at 0° C. and to this the solution of 2 (450 mg, 2.11 mmol) in THF (2 mL) was added dropwise under argon and allowed to stir at rt for 30 min The reaction mixture was then cooled at 0° C. and 15% NaOH (0.5 mL) and water (1 mL) was added dropwise. The reaction mixture was allowed to stir for 1 h, filtered and washed with EtOAc. Evaporation to remove EtOAc in vacuo afforded 4 (220 mg, 61%) as light yellow solid which was used in next step without purification. $^1$H NMR (400 MHz, CD$_3$OD) δ (ppm) 7.84 (s, 1H), 4.45 (s, 2H), 2.47 (s, 3H). $^{13}$C NMR (100 MHz, CD$_3$OD) δ 170.41, 162.27, 152.62, 111.92, 58.47, 12.58.

(4-(methylamino)-2-(methylthio)pyrimidin-5-yl)methanol (5):

The suspension of LiAlH$_4$ (626 mg, 16.50 mmol) in THF (10 mL) was cooled at 0° C. and to this the solution of 3 (2500 mg, 11.00 mmol) in THF (5 mL) was added dropwise under argon and allowed to stir at rt for 30 min The reaction mixture was then cooled at 0° C. and 15% NaOH (2 mL) and water (4 mL) was added dropwise. The reaction mixture was allowed to stir for 1 h, filtered and washed with EtOAc. Evaporation to remove EtOAc in vacuo afforded 5 (1790 mg, 95%) as light yellow solid which was used in next step without purification. $^1$H NMR (400 MHz, CD3OD) δ (ppm) 7.72 (s, 1H), 4.42 (s, 2H), 3.01 (s, 3H), 2.51 (s, 3H).

4-amino-2-(methylthio)pyrimidine-5-carbaldehyde (6):

To a solution of 4 (220 mg, 1.28 mmol) in DCM (5 mL), was added MnO$_2$ (670 mg, 7.71 mmol) and the mixture was allowed to stir overnight at rt under argon. The reaction mixture was then filtered, concentrated to remove DCM and purified by column chromatography on silica gel (30% EtOAc/hexane) to afford 6 (180 mg, 83%) as light yellow solid. $^1$H NMR (400 MHz, CDCl$_3$) δ (ppm) 9.77 (s, 1H), 8.41 (s, 1H), 8.19 (s, 1H), 5.81 (s, 1H), 2.54 (s, 3H). $^{13}$C NMR (100 MHz, CDCl$_3$) δ 190.75, 177.65, 162.95, 160.38, 109.42, 14.33.

4-(methylamino)-2-(methylthio)pyrimidine-5-carbaldehyde (7):

To a solution of 5 (1795 mg, 10.489 mmol) in DCM (15 mL), was added MnO$_2$ (5471 mg, 62.93 mmol) and the mixture was allowed to stir overnight at rt under argon. The reaction mixture was then filtered, concentrated to remove DCM and purified by column chromatography on silica gel (20% EtOAc/hexane) to afford 7 (1470 mg, 77%) as light yellow solid. IH NMR (400 MHz, CDCl$_3$) δ (ppm) 9.69 (s, 1H), 8.55 (s, 1H), 8.29 (s, 1H), 3.11 (d, J=5.0 Hz, 3H), 2.56 (s, 3H). $^{13}$C NMR (100 MHz, CDCl$_{13}$) δ 190.23, 177.59, 162.84, 159.55, 109.52, 27.21, 14.38.

General procedure for the preparation of 9a-c:

To a mixture of 4-(methylamino)-2-(methylthio)pyrimidine-5-carbaldehyde (7) (250 mg, 1.37 mmol), 2-(2,4-dichlorophenyl)acetonitrile (8a) (381 mg, 2.05 mmol) and K$_2$CO$_3$ (944 mg, 6.82 mmol) was added DMF (4 mL) under argon and the solution was refluxed at 105° C. for 18 h. After completion, the reaction mixture was partitioned between water and EtOAc and the organic layer was washed with brine solution. Evaporation to remove EtOAc in vacuo gave residue which was purified by column chromatography on silica gel (5% MeOH/DCM) to afford 9a.

6-(2,4-dichlorophenyl)-8-methyl-2-(methylthio)pyrido[2,3-d]pyrimidin-7(8H)-imine (9a):

Yield 63%, light red solid; $^1$H NMR (400 MHz, CDCl$_3$) δ (ppm) 8.34 (s, 1H), 7.57 (d, J=2 Hz, 1H), 7.41-7.37 (dd, J=2.4, 2 Hz, 1H), 7.25-7.23 (m, 1H), 7.05 (s, 1H), 3.79 (s, 3H), 2.63 (s, 3H).

6-(2-chlorophenyl)-8-methyl-2-(methylthio)pyrido[2,3-d]pyrimidin-7(8H)-imine (9b):

7 (500 mg, 2.73 mmol) and 8b (621 mg, 4.10 mmol) was used to make 9b which was used in next step without purification.

8-methyl-2-(methylthio)-6-phenylpyrido[2,3-d]pyrimidin-7(8H)-imine (9c):

7 (600 mg, 3.28 mmol) and 8c (576 mg, 4.91 mmol) was used to make 9c.

Yield 54%, light red solid; $^1$H NMR (400 MHz, CDCl$_3$) δ (ppm) 8.32 (s, 1H), 7.50-7.45 (m, 3H), 7.41-7.37 (m, 2H), 7.04 (s, 1H), 3.79 (s, 3H), 2.63 (s, 3H).

General procedure for the preparation of 13a-c:

A suspension of 9a (200 mg, 0.57 mmol) in acetic anhydride (3 mL) was refluxed at 139° C. for 30 min. Evaporation of solvent in vacuo gave residue which was treated with concentrated HCl (2 mL) and refluxed at 100° C. for 5 min The reaction mixture was then neutralized with saturated solution of NaHCO$_3$ and partitioned between water and EtOAc. The organic layer was then washed with brine solution and following concentration the residue was purified by column chromatography on silica gel (30% EtOAc/Hexane) to afford 13a.

6-(2,4-dichlorophenyl)-8-methyl-2-(methylthio)pyrido[2,3-d]pyrimidin-7(8H)-one (13a):

Yield 65%, light yellow solid; $^1$H NMR (400 MHz, CDCl$_3$) δ (ppm) 8.64 (s, 1H), 7.65-7.62 (m, 1H), 7.51 (s, 1H), 7.34-7.29 (m, 2H), 3.82 (s, 3H), 2.66 (s, 3H).

6-(2-chlorophenyl)-8-methyl-2-(methylthio)pyrido[2,3-d]pyrimidin-7(8H)-one (13b):

9b (350 mg, 1.10 mmol) was used to make 13b.

Yield 61%, light yellow solid; $^1$H NMR (400 MHz, CDCl$_3$) δ (ppm) 8.64 (s, 1H), 7.64 (s, 1H), 7.48-7.46 (m, 1H), 7.36-7.33 (m, 3H), 3.81 (s, 3H), 2.65 (s, 3H). $^{13}$C NMR (100 MHz, CDCl$_3$) δ 173.46, 161.80, 156.48, 154.35, 134.99, 134.71, 133.72, 131.60, 131.49, 129.94, 129.88, 126.86, 109.38, 28.55, 14.62.

8-methyl-2-(methylthio)-6-phenylpyrido[2,3-d]pyrimidin-7(8H)-one (13c):

9c (200 mg, 0.71 mmol) was used to make 13c.

Yield 55%, yellow solid; $^1$H NMR (500 MHz, CDCl$_3$) δ (ppm) 8.63 (s, 1H), 7.69 (s, 1H), 7.67-7.63 (m, 2H), 7.45-7.36 (m, 3H), 3.81 (s, 3H), 2.64 (s, 3H). $^{13}$C NMR (125 MHz, CDCl$_3$) δ 172.83, 162.41, 156.26, 153.94, 135.62, 132.82, 132.61, 128.91, 128.71, 128.42, 109.91, 28.49, 14.58.

General procedure for the preparation of 13d-p:

To a stirred solution of 7 (15 mg, 0.08 mmol) and 11d (23 mg, 0.12 mmol) in dry DMA (1.5 mL), KF/Al$_2$O$_3$ (76 mg, 40 wt %) was added and the reaction mixture was stirred at rt for 24 h under argon. After completion the reaction mixture was filtered through Celite and the residual solid was washed with DCM and filtrate was concentrated. The residue was purified by column chromatography over silica gel using 15% EtOAc/Hexane to give 13d as light yellow solid.

6-(4-chlorophenyl)-8-methyl-2-(methylthio)pyrido[2,3-d]pyrimidin-7(8H)-one (13d):

Yield 58%, light yellow solid; $^1$H NMR (500 MHz, CDCl$_3$) δ (ppm) 8.65 (s, 1H), 7.67 (s, 1H), 7.61 (d, J=8.5 Hz, 2H), 7.40 (d, J=8.5 Hz, 2H), 3.81 (s, 3H), 2.65 (s, 3H). $^{13}$C NMR (125 MHz, CDCl$_3$) δ 173.19, 162.23, 156.38, 153.94, 134.73, 134.01, 132.69, 131.55, 130.23, 128.63, 109.76, 28.54, 14.60.

6-(4-(tert-butyl)phenyl)-8-methyl-2-(methylthio)pyrido[2,3-d]pyrimidin-7(8H)-one (13e):

Yield 41%, yellow solid; $^1$H NMR (400 MHz, CDCl$_3$) δ (ppm) 8.64 (s, 1H), 7.68 (s, 1H), 7.61 (d, J=6 Hz, 2H), 7.46 (d, J=7.6 Hz, 2H), 3.81 (s, 3H), 2.64 (s, 3H), 1.35 (s, 9H). $^{13}$C NMR (100 MHz, CDCl$_3$) δ 172.61, 162.56, 156.16, 153.88, 151.86, 132.74, 132.68, 132.09, 128.59, 125.45, 110.01, 34.80, 31.39, 28.51, 14.59.

6-(2,6-dichlorophenyl)-8-methyl-2-(methylthio)pyrido[2,3-d]pyrimidin-7(8H)-one (13f):

Yield 30%, white solid; $_1$H NMR (400 MHz, CDCl$_3$) δ (ppm) 8.67 (s, 1H), 7.61 (s, 1H), 7.42 (d, J=7.8 Hz, 2H), 7.33-7.26 (m, 1H), 3.84 (s, 3H), 2.67 (s, 3H). $^{13}$C NMR (100 MHz, CDCl$_3$) δ 173.85, 161.03, 156.62, 154.52, 136.01, 135.51, 133.76, 130.29, 129.55, 128.18, 109.26, 28.55, 14.64.

6-(2,3-dichlorophenyl)-8-methyl-2-(methylthio)pyrido[2,3-d]pyrimidin-7(8H)-one (13g):

Yield 38%, white solid; $^1$H NMR (500 MHz, CDCl$_3$) δ (ppm) 8.65 (s, 1H), 7.64 (s, 1H), 7.52 (dd, J=7.5, 2 Hz, 1H), 7.30-7.24 (m, 2H), 3.82 (s, 3H), 2.67 (s, 3H).

6-(2-chloro-4-fluorophenyl)-8-methyl-2-(methylthio)pyrido[2,3-d]pyrimidin-7(8H)-one (13h):

Yield 35%, white solid; $^1$H NMR (400 MHz, CDCl$_3$) δ (ppm) 8.63 (s, 1H), 7.64 (s, 1H), 7.35-7.30 (m, 1H), 7.24-7.15 (m, 1H), 7.04 (td, J=8.4, 2.8 Hz, 1H), 3.80 (s, 3H), 2.64 (s, 3H). $^{13}$C NMR (150 MHz, CDCl$_3$) δ 173.65, 163.34, 161.78, 161.67, 156.50, 154.33, 135.30, 134.72, 134.65, 132.65, 132.59, 130.81, 130.51, 117.41, 117.25, 114.28, 114.14, 109.27, 28.54, 14.59.

Preparation of (13o):

Methyl 2-(2,5-dichlorophenyl)acetate (11o):

To a stirred solution of 11o* (100 mg, 0.537 mmol) in methanol (3 mL) thionly chloride (0.5 mL) was added dropwise at 0° C. The reaction mixture was maintained at the same temperature for 5 h and then stirred overnight at room temperature. Following completion, the reaction mixture was concentrated and diluted with EtOAc. The organic layer was then washed with sodium bicarbonate and brine solutions and following concentration the residue was purified by column chromatography on silica gel (20% EtOAc/Hexane) to afford 11o. Yield 59%, colourless liquid; $^1$H NMR (400 MHz, CDCl$_3$) δ (ppm) 7.32-7.28 (m, 2H), 7.22-7.19 (m, 1H), 3.74 (s, 2H), 3.72 (s, 3H). $^{13}$C NMR (100 MHz, CDCl$_3$) δ 170.47, 134.04, 132.96, 132.69, 131.47, 130.62, 128.88, 52.44, 38.83.

6-(2,5-dichlorophenyl)-8-methyl-2-(methylthio)pyrido[2,3-d]pyrimidin-7(8H)-one (13o)

Yield 23%, white solid; $^1$H NMR (400 MHz, CDCl$_3$) δ (ppm) 8.65 (s, 1H), 7.66 (s, 1H), 7.43-7.31 (m, 3H), 3.82 (s, 3H), 2.66 (s, 3H).

6-(4-hydroxyphenyl)-8-methyl-2-(methylthio)pyrido[2,3-d]pyrimidin-7(8H)-one (13p)

Yield 55%, light yellow solid; $^1$H NMR (400 MHz, DMSO-d6) δ (ppm) 9.68 (s, 1H), 8.87 (s, 1H), 7.99 (s, 1H), 7.54 (d, J=8.8 Hz, 2H), 6.81 (d, J=8 Hz, 2H), 3.64 (s, 3H), 2.59 (s, 3H).

General procedure for preparation of 12i, 12k and 12n:

To a stirred solution of 6 (37 mg, 0.22 mmol) and methyl 2-phenylacetate (11i) (30 mg, 0.20 mmol) in dry DMA (2.0 mL), KF/Al$_2$O$_3$ (187 mg, 40 wt %) was added and the reaction mixture was stirred at rt for 24 h under argon. After completion the reaction mixture was filtered through Celite and the residual solid was washed with DCM and filtrate was concentrated. The residue was purified by column chromatography over silica gel using 30% EtOAc/Hexane to give 12i as white solid.

2-(methylthio)-6-phenylpyrido[2,3-d]pyrimidin-7(8H)-one (12i):

Yield 51%, white solid; $^1$H NMR (500 MHz, CDCl$_3$) δ (ppm) 9.66 (s, 1H), 8.70 (s, 1H), 7.77 (s, 1H), 7.70 (d, J=7.5 Hz, 2H), 7.47-7.39 (m, 3H), 2.62 (s, 3H). $^{13}$C NMR (125 MHz, CDCl$_3$) δ 173.59, 162.29, 156.05, 152.33, 134.76, 134.05, 133.58, 128.97, 128.79, 128.53, 109.60, 14.47.

6-(2,6-dichlorophenyl)-2-(methylthio)pyrido[2,3-d]pyrimidin-7(8H)-one (12k):

Yield 28%, light yellow solid; $^1$H NMR (400 MHz, CDCl$_3$) δ (ppm) 9.81 (s, 1H), 8.70 (s, 1H), 7.65 (s, 1H), 7.41 (d, J=8.4 Hz, 2H), 7.30 (dd, J=8.7, 7.8 Hz, 1H), 2.60 (s, 3H). $^{13}$C NMR (100 MHz, CDCl$_3$) δ 174.52, 160.89, 156.42, 153.96, 137.76, 135.57, 132.95, 130.47, 130.33, 128.21, 108.85, 14.51.

6-(4-chlorophenyl)-2-(methylthio)pyrido[2,3-d]pyrimidin-7(8H)-one (12n):

Yield 40%, white solid; $^1$H NMR (400 MHz, CDCl$_3$) δ (ppm) 9.54 (s, 1H), 8.71 (s, 1H), 7.77 (s, 1H), 7.66 (d, J=8.8 Hz, 2H), 7.42 (d, J=8.8 Hz, 2H), 2.62 (s, 3H). $^{13}$C NMR (100 MHz, CDCl$_3$) δ 173.93, 161.96, 156.14, 153.31, 135.03, 134.12, 133.13, 132.31, 130.10, 128.76, 109.44, 14.50.

General procedure for preparation of 13i-r:

To a mixture of 12i (20 mg, 0.07 mmol) and NaH (3 mg, 0.11 mmol) was added DMF (1.5 mL) under argon followed by drop wise addition of iodoethane (10 0.11 mmol). The reaction mixture was heated at 50° C. for 1 h and was partitioned between water and EtOAc after completion. The organic layer was then washed with brine solution, dried over anhydrous Na$_2$SO$_4$, filtered and concentrated. The residue was purified by column chromatography on silica gel (10% EtOAc/hexane) to afford 13i as colourless liquid.

8-ethyl-2-(methylthio)-6-phenylpyrido[2,3-d]pyrimidin-7(8H)-one (13i):

Yield 74%, colourless liquid; $^1$H NMR (400 MHz, CDCl$_3$) δ (ppm) 8.66 (s, 1H), 7.71-7.65 (m, 3H), 7.47-7.36 (m, 3H), 4.56 (q, J=7.2 Hz, 2H), 2.65 (s, 3H), 1.37 (t, J=7.1 Hz, 3H). $^{13}$C NMR (100 MHz, CDCl$_3$) δ 172.79, 161.86, 156.37, 153.45, 135.66, 133.05, 132.63, 128.97, 128.72, 128.42, 109.95, 29.81, 14.56, 13.07.

8-(2-hydroxyethyl)-2-(methylthio)-6-phenylpyrido [2,3-d]pyrimidin-7(8H)-one (13j):

Purified by column chromatography on silica gel (40% EtOAc/hexane) to afford 13j (Yield 48%), light yellow viscous liquid; $^1$H NMR (400 MHz, CDCl$_3$) δ (ppm) 8.61 (s, 1H), 7.67 (s, 1H), 7.54 (d, J=8 Hz, 2H), 7.39-7.31 (m, 3H), 4.63 (t, J=6 Hz, 2H), 3.88 (t, J=6 Hz, 2H), 2.56 (s, 3H). $^{13}$C NMR (100 MHz, CDCl$_3$) δ 172.93, 163.05, 156.53, 153.70, 135.30, 133.37, 132.90, 128.84, 128.79, 128.40, 109.97, 59.94, 43.65, 14.45.

6-(2,6-dichlorophenyl)-8-(2-methoxyethyl)-2-(methylthio)pyrido[2,3-d]pyrimidin-7(8H)-one (13k):

Yield 44%, colourless liquid; $^1$H NMR (400 MHz, CDCl$_3$) δ (ppm) 8.67 (s, 1H), 7.62 (s, 1H), 7.41 (d, J=7.8 Hz, 2H), 7.34-7.25 (m, 1H), 4.74 (t, J=6.2 Hz, 2H), 3.78 (t, J=6.2 Hz, 2H), 3.39 (s, 3H), 2.65 (s, 3H). $^{13}$C NMR (100 MHz, CDCl$_3$) δ 173.77, 160.73, 156.77, 154.39, 136.24, 135.50, 133.71, 130.26, 129.59, 128.17, 109.27, 68.99, 58.95, 40.33, 14.64.

8-benzyl-6-(2,6-dichlorophenyl)-2-(methylthio)pyrido[2,3-d]pyrimidin-7(8H)-one (13l):

Yield 29%, white semisolid; $^1$H NMR (400 MHz, CDCl$_3$) δ (ppm) 8.65 (s, 1H), 7.61 (s, 1H), 7.47 (d, J=6.9 Hz, 2H), 7.41 (d, J =8.2 Hz, 2H), 7.32-7.22 (m, 4H), 5.70 (s, 2H), 2.61 (s, 3H). $^{13}$C NMR (100 MHz, CDCl$_3$) δ 173.87, 160.94, 156.76, 154.21, 136.85, 136.33, 135.52, 133.76, 130.31, 129.80, 128.93, 128.59, 128.57, 128.20, 127.65, 109.38, 44.72, 14.73.

6-(2,6-dichlorophenyl)-8-isobutyl-2-(methylthio)pyrido [2,3-d]pyrimidin-7(8H)-one (13m):

Yield 28%, white solid; $^1$H NMR (400 MHz, CDCl$_3$) δ (ppm) 8.66 (s, 1H), 7.60 (s, 1H), 7.41 (d, J=8 Hz, 2H), 7.29 (t, J=8, 7.2 Hz, 1H), 4.36 (d, J=7.6 Hz, 2H), 2.65 (s, 3H), 2.40-2.30 (sep, J=6.8, 7.2 Hz, 1H), 0.98 (d, J=6.9 Hz, 6H). $^{13}$C NMR (100 MHz, CDCl$_3$) δ 173.48, 161.02, 156.76, 154.49, 135.90, 135.48, 133.92, 130.21, 129.77, 128.15, 109.16, 48.39, 27.57, 20.37, 14.59.

6-(4-chlorophenyl)-8-isobutyl-2-(methylthio)pyrido[2,3-d]pyrimidin-7(8H)-one (13n):

Yield 73%, yellow solid; $^1$H NMR (400 MHz, CDCl$_3$) δ (ppm) 8.66 (s, 1H), 7.70 (s, 1H), 7.63 (d, J=8.8 Hz, 2H), 7.41 (d, J=8.8 Hz, 2H), 4.36 (d, J=7.3 Hz, 2H), 2.64 (s, 3H), 2.33 (sep, J=7.2, 6.8 Hz, 1H), 0.98 (d, J=6.8 Hz, 6H).

6-(2,6-dichlorophenyl)-8-(3-(methylsulfonyl)benzyl)-2-(methylthio)pyrido[2,3-d]pyrimidin-7(8H)-one (13q):

Yield 36%, light yellow solid; $^1$H NMR (400 MHz, CDCl$_3$) δ (ppm) 8.69 (s, 1H), 8.08 (s, 1H), 7.84 (d, J=8 Hz, 1H), 7.75 (d, J=8 Hz, 1H), 7.65 (s, 1H), 7.51 (t, J=7.8 Hz, 1H), 7.43 (d, J=8 Hz, 2H), 7.32-7.28 (m, 1H), 5.76 (s, 2H), 3.03 (s, 3H), 2.63 (s, 3H).

6-(2,6-dichlorophenyl)-8-(4-(methylsulfonyl)benzyl)-2-(methylthio)pyrido[2,3-d]pyrimidin-7(8H)-one (13r):

Yield 53%, pale yellow solid; $^1$H NMR (400 MHz, CDCl$_3$) δ (ppm) 8.70 (s, 1H), 7.87 (d, J=8.4 Hz, 2H), 7.67-7.61 (m, 3H), 7.42 (d, J=8 Hz, 2H), 7.32-7.28 (m, 1H), 5.76 (s, 2H), 3.02 (s, 3H), 2.58 (s, 3H).

6-(4-methoxyphenyl)-8-methyl-2-(methylthio)pyrido[2,3-d]pyrimidin-7(8H)-one (13s):

To a solution of 13p (20 mg, 0.06 mmol) in acetone (2 mL) was added anhydrous potassium carbonate (14 mg, 0.10 mmol), iodomethane (10 μl, 0.10 mmol) and the mixture was allowed to reflux for 8h. After completion, the crude mixture was extracted with ethyl acetate and water, concentrated and purified by column chromatography using silica gel (20% EtOAc/Hexane) to get 13s (20 mg, 95%) as light yellow solid. $^1$H NMR (400 MHz, CDCl$_3$) δ (ppm) 8.64 (s, 1H), 7.65-7.62 (m, 3H), 6.96 (d, J=8.8 Hz, 2H), 3.85 (s, 3H), 3.81 (s, 3H), 2.65 (s, 3H). $^{13}$C NMR (100 MHz, CDCl$_3$) δ 172.42, 162.64, 160.05, 156.04, 153.78, 132.40, 131.40, 130.20, 127.99, 113.86, 110.07, 55.47, 28.51, 14.58.

General procedure for preparation of 14a-s:

To a solution of 6-(2,4-dichlorophenyl)-8-methyl-2-(methylthio)pyrido[2,3-d]pyrimidin-7(8H)-one (13a) (38 mg, 0.108 mmol) in DCM (2 mL), mCPBA (85 mg, 55%) was added and allowed to stir for 3 h. The reaction mixture was then partitioned between water and DCM and the organic layer was washed with brine. Following concentration the residue was purified by column chromatography using silica gel (40% EtOAc/Hexane) to get 14a as white powder.

6-(2,4-dichlorophenyl)-8-methyl-2-(methylsulfonyl)pyrido[2,3-d]pyrimidin-7(8H)-one (14a):

Yield 63%, white solid; $^1$H NMR (400 MHz, CDCl$_3$) δ (ppm) 9.01 (s, 1H), 7.82 (s, 1H), 7.53 (d, J=1.8 Hz, 1H), 7.36 (dd, J=8.2, 2.3 Hz, 1H), 7.31 (d, J=8.2 Hz, 1H), 3.89 (s, 3H), 3.43 (s, 3H). $^{13}$C NMR (100 MHz, CDCl$_3$) δ 164.74, 161.01, 157.38, 155.18, 136.0, 135.42, 134.32, 134.03, 132.11, 132.05, 131.01, 127.44, 114.90, 39.32, 29.39.

6-(2-chlorophenyl)-8-methyl-2-(methylsulfonyl)pyrido[2,3-d]pyrimidin-7(8H)-one (14b):

Yield 45%, white solid; $^1$H NMR (400 MHz, CDCl$_3$) δ (ppm) 9.00 (s, 1H), 7.82 (s, 1H), 7.48 (d, J=7.2 Hz, 1H), 7.42-7.32 (m, 3H), 3.87 (s, 3H), 3.42 (s, 3H). $^{13}$C NMR (100 MHz, CDCl$_3$) δ 164.51, 161.17, 157.31, 155.12, 136.52, 133.79, 133.71, 133.44, 131.20, 130.63, 130.03, 127.04, 115.06, 39.45, 29.31.

8-methyl-2-(methylsulfonyl)-6-phenylpyrido[2,3-d]pyrimidin-7(8H)-one (14c):

Yield 54%, light yellow solid; IH NMR (400 MHz, CDCl$_3$) δ (ppm) 9.00 (s, 1H), 7.85 (s, 1H), 7.70-7.66 (m, 2H), 7.49-7.44 (m, 3H), 3.88 (s, 3H), 3.42 (s, 3H). $^{13}$C NMR (100 MHz, CDCl$_3$) δ 164.02, 161.87, 156.91, 154.62, 137.62, 134.54, 131.150, 129.73, 129.0, 128.64, 115.60, 39.34, 29.30.

6-(4-chlorophenyl)-8-methyl-2-(methylsulfonyl)pyrido[2,3-d]pyrimidin-7(8H)-one (14d):

Yield 72%, white solid; $^1$H NMR (400 MHz, CDCl$_3$) δ (ppm) 9.01 (s, 1H), 7.86 (s, 1H), 7.652 (d, J=8.8 Hz, 2H), 7.445 (d, J=8.8 Hz, 2H), 3.89 (s, 3H), 3.43 (s, 3H). $^{13}$C NMR (100 MHz, CDCl$_3$) δ 164.25, 161.66, 157.04, 154.67, 136.40, 135.91, 132.91, 131.17, 130.35, 128.90, 115.43, 39.32, 29.37.

6-(4-(tert-butyl)phenyl)-8-methyl-2-(methylsulfonyl)pyrido[2,3-d]pyrimidin-7(8H)-one (14e):

Yield 81%, white solid; $^1$H NMR (400 MHz, CDCl$_3$) δ (ppm) 8.98 (s, 1H), 7.84 (s, 1H), 7.63 (d, J=8.8 Hz, 2H), 7.47 (d, J=8 Hz, 2H), 3.86 (s, 3H), 3.40 (s, 3H), 1.34 (s, 9H). $^{13}$C NMR (100 MHz, CDCl$_3$) δ 163.80, 161.99, 156.86, 154.47, 153.03, 137.37, 131.67, 130.63, 128.74, 125.63, 115.72, 39.36, 34.91, 31.33, 29.27.

6-(2,6-dichlorophenyl)-8-methyl-2-(methylsulfonyl)pyrido[2,3-d]pyrimidin-7(8H)-one (14f):

Yield 93%, white solid; $^1$H NMR (600 MHz, CDCl$_3$) δ (ppm) 9.03 (s, 1H), 7.77 (s, 1H), 7.45 (d, J=7.8 Hz, 2H), 7.35 (t, J=7.8, 9 Hz, 1H), 3.91 (s, 3H), 3.44 (s, 3H).

6-(2,3-dichlorophenyl)-8-methyl-2-(methylsulfonyl)pyrido[2,3-d]pyrimidin-7(8H)-one (14g):

Yield 65%, light yellow solid; $^1$H NMR (400 MHz, CDCl$_3$) δ (ppm) 9.02 (s, 1H), 7.82 (s, 1H), 7.57 (dd, J=8, 2 Hz, 1H), 7.34-7.25 (m, 2H), 3.90 (s, 3H), 3.44 (s, 3H). $^{13}$C NMR (100 MHz, CDCl$_3$) δ 164.75, 160.90, 157.41, 155.23, 136.46, 135.86, 133.94, 133.73, 132.07, 131.40, 129.24, 127.65, 114.92, 39.34, 29.39.

6-(2-chloro-4-fluorophenyl)-8-methyl-2-(methylsulfonyl)pyrido[2,3-d]pyrimidin-7(8H)-one (14h):

Yield 40%, white solid; $^1$H NMR (400 MHz, CDCl$_3$) δ (ppm) 9.02 (s, 1H), 7.83 (s, 1H), 7.37 (dd, J=14, 6.6 Hz, 1H), 7.29-7.26 (m, 1H), 7.11 (td, J=8, 2.4 Hz, 1H), 3.90 (s, 3H), 3.44 (s, 3H). $^{13}$C NMR (150 MHz, CDCl$_3$) δ 164.69, 163.74, 162.06, 161.17, 157.30, 155.16, 135.53, 134.58, 134.51, 134.06, 132.47, 132.41, 129.76, 117.70, 117.54, 114.94, 114.56, 114.42, 39.32, 29.37. DEPT 6 157.31, 134.06, 132.48, 132.41, 117.71, 117.54, 114.56, 114.43, 39.32, 29.37.

8-ethyl-2-(methylsulfonyl)-6-phenylpyrido[2,3-d]pyrimidin-7(8H)-one (14i):

Yield 55%, white solid; $^1$H NMR (400 MHz, CDCl$_3$) δ (ppm) 9.01 (s, 1H), 7.85 (s, 1H), 7.72-7.67 (m, 2H), 7.52-7.44 (m, 3H), 4.60 (q, J=7.0 Hz, 2H), 3.42 (s, 3H), 1.40 (t, J=7.1 Hz, 3H).

8-(2-hydroxyethyl)-2-(methylsulfonyl)-6-phenylpyrido[2,3-d]pyrimidin-7(8H)-one (14j):

Yield 81%, light yellow solid which was used without purification in next step.

6-(2,6-dichlorophenyl)-8-(2-methoxyethyl)-2-(methylsulfonyl)pyrido[2,3-d]pyrimidin-7(8H)-one (14k):

Yield 58%, white solid; $^1$H NMR (400 MHz, CDCl$_3$) δ (ppm) 9.02 (s, 1H), 7.78 (s, 1H), 7.43 (d, J=8.2 Hz, 2H), 7.33 (dd, J=8.8, 7.2 Hz, 1H), 4.79 (t, J=5.6 Hz, 2H), 3.80 (t, J=5.6 Hz, 2H), 3.41 (s, 3H), 3.36 (s, 3H). $^{13}$C NMR (100 MHz, CDCl$_3$) δ 164.64, 160.21, 157.62, 155.39, 135.10, 134.58, 132.73, 130.87, 128.32, 114.87, 69.08, 58.97, 41.25, 39.42.

8-benzyl-6-(2,6-dichlorophenyl)-2-(methylsulfonyl)pyrido[2,3-d]pyrimidin-7(8H)-one (14l):

Yield 61%, white solid; $^1$H NMR (400 MHz, CDCl$_3$) δ (ppm) 9.01 (s, 1H), 7.78 (s, 1H), 7.59 (d, J=7.6 Hz, 2H), 7.45 (d, J=8 Hz, 2H), 7.39-7.24 (m, 4H), 5.73 (s, 2H), 3.33 (s, 3H). $^{13}$C NMR (100 MHz, CDCl$_3$) δ 164.58, 160.37, 157.60, 154.88, 135.84, 135.08, 134.92, 132.76, 130.92, 129.35, 128.76, 128.35, 128.19, 115.04, 45.49, 39.48.

6-(2,6-dichlorophenyl)-8-isobutyl-2-(methylsulfonyl)pyrido[2,3-d]pyrimidin-7(8H)-one (14m):

Yield 87%, white solid; $^1$H NMR (400 MHz, CDCl$_3$) δ (ppm) 9.03 (s, 1H), 7.77 (s, 1H), 7.43 (d, J=7.6 Hz, 2H), 7.33 (dd, J=9.0, 7.4 Hz, 1H), 4.40 (d, J=7.3 Hz, 2H), 3.41 (s, 3H), 2.37-2.27 (sep, J=6.8, 7.2 Hz, 1H), 0.98 (d, J=6.9 Hz, 6H). $^{13}$C NMR (100 MHz, CDCl$_3$) δ 164.67, 160.45, 157.70, 155.21, 135.04, 134.83, 134.71, 132.88, 130.84, 128.30, 114.80, 49.14, 39.27, 27.60, 20.27.

6-(4-chlorophenyl)-8-isobutyl-2-(methylsulfonyl)pyrido[2,3-d]pyrimidin-7(8H)-one (14n):

Yield 66%, light brown solid which was used without purification in next step.

6-(2,5-dichlorophenyl)-8-methyl-2-(methylsulfonyl)pyrido[2,3-d]pyrimidin-7(8H)-one (14o):

Yield 75%, white solid; $^1$H NMR (400 MHz, CDCl$_3$) δ ppm) 9.02 (s, 1H), 7.83 (s, 1H), 7.46-7.47 (m, 1H), 7.39-7.36 (m, 2H), 3.89 (s, 3H), 3.44 (s, 3H). $^{13}$C NMR (100 MHz, CDCl$_3$) δ 164.84, 160.84, 157.46, 155.23, 135.36, 135.00, 134.11, 132.95, 131.89, 131.17, 131.11, 130.64, 114.83, 39.33, 29.40.

6-(4-((tert-butyldimethylsilyl)oxy)phenyl)-8-methyl-2-(methylthio)pyrido[2,3-d]pyrimidin-7(8H)-one (13p*):

To a solution of 13p (160 mg, 0.53 mmol) in DMF (2 mL), Imidazole (109 mg, 1.60 mmol) and DMAP (catalytic 3 mg) were added and the temperature was reduced to 0° C. TBDMSCl (121 mg, 0.80 mmol) in DMF (1 mL) was added to the above solution and the resulting mixture was stirred at rt overnight. Following completion, the reaction was partitioned between EtOAc and water and the organic layer was filtered, concentrated and purified by column chromatography using silica gel (5% EtOAc/DCM) to get 13p* (194 mg, 88%) as light yellow solid. $^1$H NMR (600 MHz, CDCl$_3$) δ (ppm) 8.64 (s, 1H), 7.66 (s, 1H), 7.57 (d, J=8.4 Hz, 2H), 6.89 (d, J=7.8 Hz, 2H), 3.81 (s, 3H), 2.65 (s, 3H), 0.99 (s, 9H), 0.22 (s, 6H).

6-(4-((tert-butyldimethylsilyl)oxy)phenyl)-8-methyl-2-(methylsulfonyl)pyrido[2,3-d]pyrimidin-7(8H)-one (14p):

Yield 64%, light yellow solid; $^1$H NMR (600 MHz, CDCl$_3$) δ (ppm) 8.96 (s, 1H), 7.80 (s, 1H), 7.60 (d, J=8.4 Hz, 2H), 6.88 (d, J=8.4 Hz, 2H), 3.85 (s, 3H), 3.39 (s, 3H), 0.98 (s, 9H), 0.21 (s, 6H). $^{13}$C NMR (150 MHz, CDCl$_3$) δ 163.62, 161.99, 157.25, 156.61, 154.28, 136.96, 130.41, 129.87, 127.53, 120.19, 115.76, 39.34, 29.22, 25.74, 18.32.

6-(2,6-dichlorophenyl)-2-(methylsulfonyl)-8-(3-(methylsulfonyl)benzyl)pyrido[2,3-d]pyrimidin-7(8H)-one (14q):

Yield 79%, white powder; $^1$H NMR (500 MHz, CDCl$_3$) δ (ppm) 9.03 (s, 1H), 8.25 (s, 1H), 7.91 (d, J=8 Hz, 1H), 7.86 (d, J=8 Hz, 1H), 7.81 (s, 1H), 7.52 (t, J=7.5 Hz, 1H), 7.46 (d, J=7.5 Hz, 2H), 7.38-7.33 (m, 1H), 5.79 (s, 2H), 3.39 (s, 3H), 3.09 (s, 3H).

6-(2,6-dichlorophenyl)-2-(methylsulfonyl)-8-(4-(methylsulfonyl)benzyl)pyrido[2,3-d]pyrimidin-7(8H)-one (14r):

Yield 72%, white powder; $^1$H NMR (500 MHz, CDCl$_3$) δ (ppm) 9.03 (s, 1H), 7.89-7.81 (m, 5H), 7.46 (d, J=8 Hz, 2H), 7.38-7.35 (m, 1H), 3.37 (s, 3H), 3.01 (s, 3H).

6-(4-methoxyphenyl)-8-methyl-2-(methylsulfonyl)pyrido[2,3-d]pyrimidin-7(8H)-one (14s):

Yield 97%, yellow solid; $^1$H NMR (400 MHz, CDCl$_3$) δ (ppm) 8.98 (s, 1H), 7.80 (s, 1H), 7.68 (d, J=8.8 Hz, 2H), 6.98 (d, J=8.8 Hz, 2H), 3.88 (s, 3H), 3.86 (s, 3H), 3.42 (s, 3H).

4-(2-(diethylamino)ethoxy)aniline (15a):

To a solution of N,N-diethyl-2-(4-nitrophenoxy)ethanamine (490 mg, 2.06 mmol) in CH$_3$OH (10 mL) was added 10% Pd/C (125 mg) in excess and H$_2$ (g) was passed through latex valve bladder for 4 h. The reaction mixture was then filtered through Celite and concentrated to afford 15a (412 mg, 96%) as brown viscous liquid. $^1$H NMR (400 MHz, CDCl$_3$) δ (ppm) 6.75-6.73 (m, 2H), 6.64-6.62 (m, 2H), 3.98 (t, J=6.4 Hz, 2H), 2.84 (t, J =6.4 Hz, 2H), 2.63 (q, J=7.2 Hz, 4H), 1.06 (t, J=7.2 Hz, 6H). $^{13}$C NMR (100 MHz, CDCl$_3$) δ 152.11, 140.03, 116.49, 115.68, 66.98, 51.88, 47.82, 11.80.

N-(4-(2-(diethylamino)ethoxy)phenyl)formamide (16a):

Method A: Formic acid (1 mL) was added to 15a (100 mg, 0.48 mmol) in round bottom flask containing molecular sieves. The reaction mixture was heated at 60° C. for 6 h and then partitioned between saturated solution of NaHCO$_3$ and EtOAc. The organic layer was then washed with brine solution and then concentrated to give 16a (90 mg, 79%) as brown viscous liquid which was used directly into next step without purification.

N-(4-(methylsulfonyl)phenyl)formamide (16b):

16b was prepared by method A where the reaction mixture was stirred at room temperature with overnight stirring. Yield 80%, white solid which was directly used in next step without purification.

N-(3-(methylsulfonyl)phenyl)formamide (16c):

16c was prepared by method A where the reaction mixture was stirred at room temperature with overnight stirring. Yield 80%, white solid; $^1$H NMR (400 MHz, DMSO-d6) δ (ppm) 10.64 (s, 1H), 8.40 (s, 1H), 8.28 (s, 1H), 7.89-7.86 (m, 1H), 7.67-7.63 (m, 2H), 3.24 (s, 3H). $^{13}$C NMR (100 MHz, DMSO-d6) δ 160.74, 141.95, 139.44, 130.80, 124.15, 122.51, 117.54, 44.08.

Preparation of (16d):

tert-Butyl 4-(3-nitrophenyl)piperazine-1-carboxylate (15d*):

To a solution of Boc anhydride (790 mg, 3.62 mmol) in DCM (10 mL), DMAP (60 mg, 0.49 mmol) was added and the solution was allowed to stir for 5 min 1-(3-nitrophenyl)piperazine (500 mg, 2.41 mmol) was then added to the above solution and allowed to stir for 20 h at room temperature. Following completion, the reaction mixture was concentrated and purified by column chromatography using silica gel (30% EtOAc/Hexane) to get 15d* (700 mg, 94%) as yellow solid. $^1$H NMR (400 MHz, CDCl$_3$) δ (ppm) 7.71-7.66 (m, 2H), 7.38 (t, J=8.2 Hz, 1H), 7.19-7.17 (m, 1H), 3.59 (t, J=5.2 Hz, 4H), 3.23 (t, J=5 Hz, 4H), 1.48 (s, 9H). $^{13}$C NMR (100 MHz, CDCl$_3$) δ 154.68, 151.83, 149.31, 129.90, 121.74, 114.33, 110.23, 80.30, 48.59, 28.49.

tert-Butyl 4-(3-aminophenyl)piperazine-1-carboxylate (15d):

To a solution of 15d* (700 mg, 2.27 mmol) in CH$_3$OH (15 mL) was added 10% Pd/C (200 mg) in excess and H2 (g) was passed through latex valve bladder for overnight. The reaction mixture was then filtered through celite and concentrated to afford 15d (600 mg, 95%) as brown viscous liquid which was used in next step without purification.

tert-Butyl 4-(3-formamidophenyl)piperazine-1-carboxylate (16d):

Method B: To a round bottom flask fitted with reflux condenser was added 15d (200 mg, 0.72 mmol) and ethyl formate (1.16 mL, 14.4 mmol). TEA (0.15 mL, 1.08 mmol) was added to the above mixture and heated under reflux. After overnight stirring, solvent was evaporated, and the mixture was dissolved in DCM and extracted with water and brine solution. The extract was concentrated and purified by column chromatography using silica gel (30% EtOAc/Hexane) to get 16d (100mg, 45%) as colourless liquid.

N-(pyridin-2-yl)formamide (16e):

Method C: Formic acid (0.28 mL, 7.43 mmol) was added dropwise to acetic anhydride (0.60 mL, 6.37 mmol) maintained at 0° C. The mixture was heated to reflux at 60° C. for 2 h to generate acetic formic anhydride reagent. The mixture was cooled to room temperature and 2 mL THF was added. 15e (200 mg, 2.12 mmol) dissolved in THF (1 mL) was added to acetic formic anhydride mixture and refluxed for another 2 h. Solvent was evaporated after completion, extracted in EtOAc/water system. Extract was concentrated and purified by column chromatography using silica gel (3% MeOH/DCM) to get 16e (173 mg, 67%) as white solid.

N-(pyridin-3-yl)formamide (16f):

16f was prepared by method C: Yield 75%, white solid.

Figure 11:
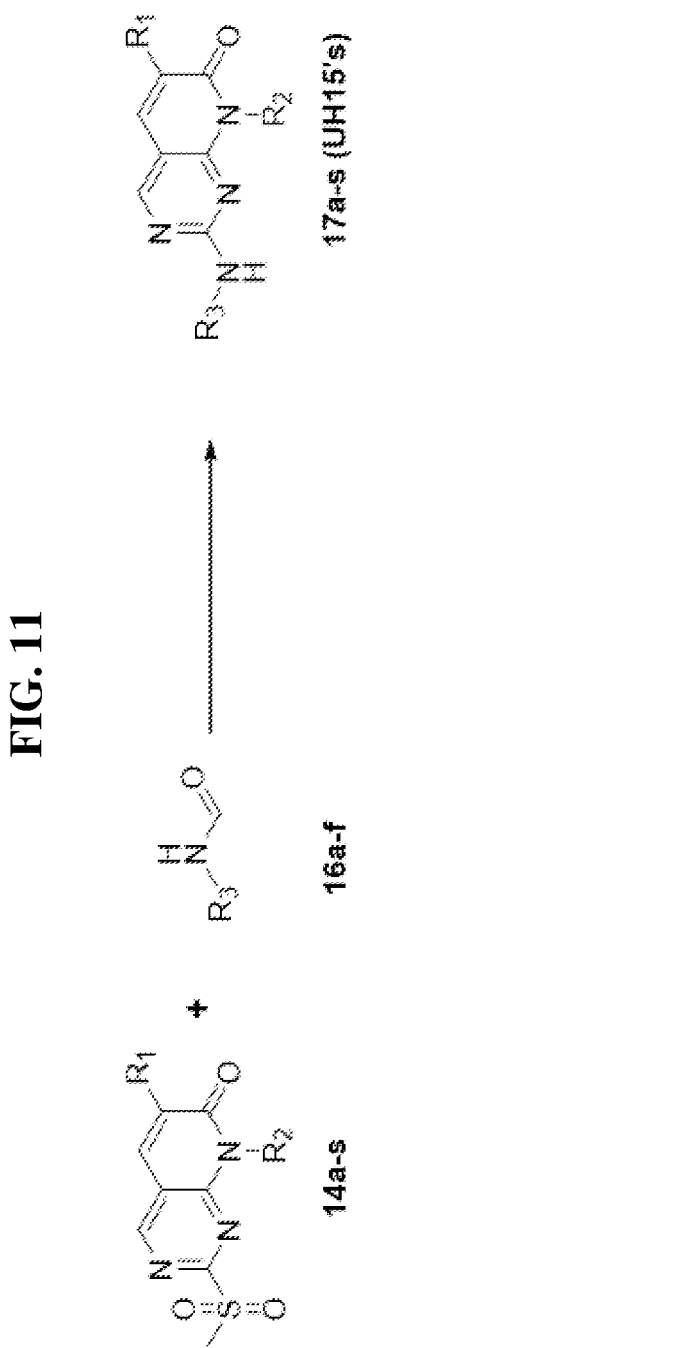
FIG. 11 shows a synthetic scheme for exemplary inhibitors of protein kinase, in accordance with preferred embodiments.
Figure 12:
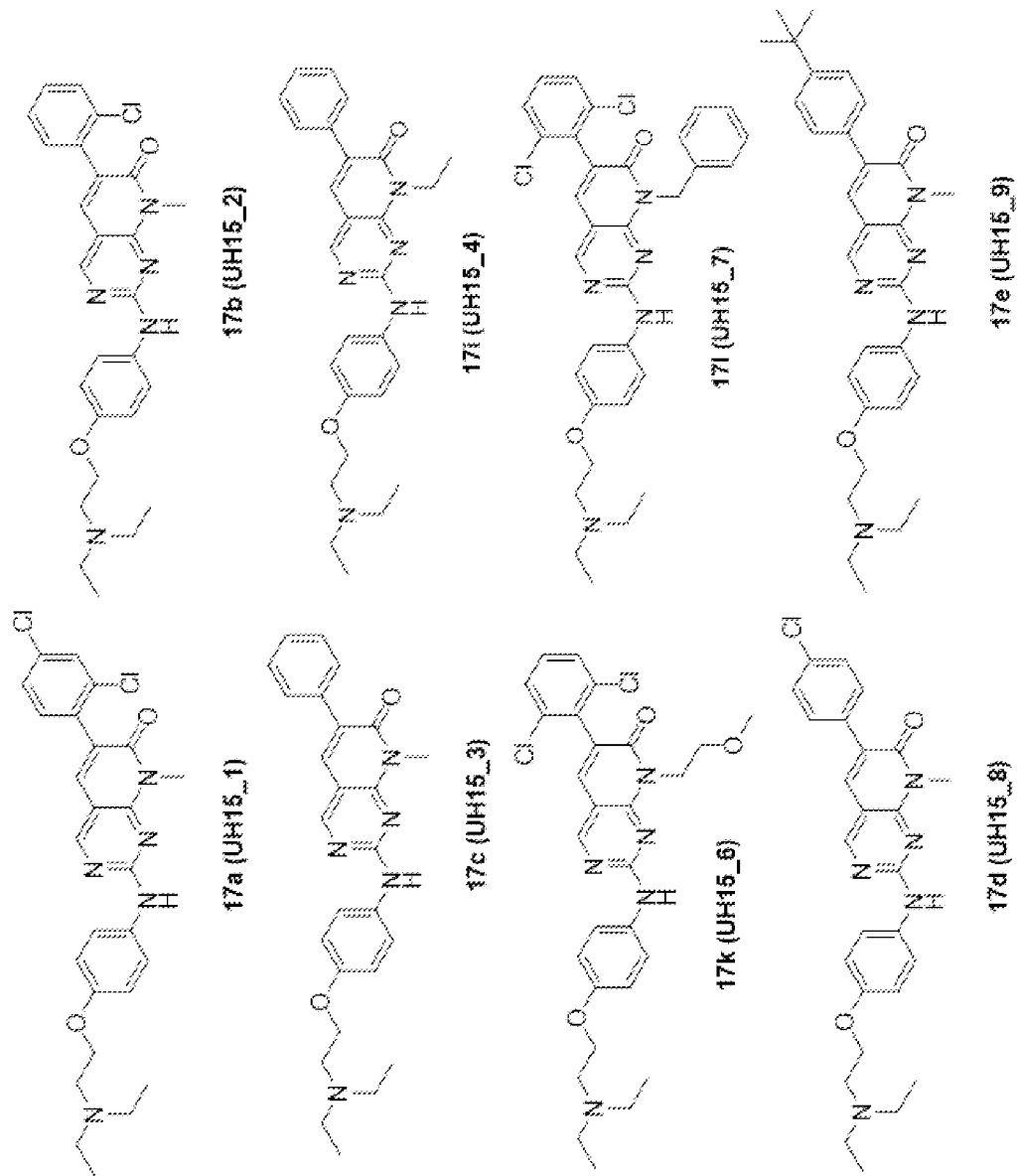
FIG. 12 shows structures for exemplary inhibitors of protein kinase, in accordance with preferred embodiments.

General procedure for preparation of 17a-s:

FIG. 11 shows a synthetic scheme for exemplary inhibitors of protein kinase, compounds 17a-s (UH15's). FIGS. 12-15 show structures for exemplary inhibitors of protein kinase, in accordance with preferred embodiments.

To a solution of 16a (30 mg, 0.13 mmol) in THF (0.5 mL) and DMF (0.5 mL) was added 60% NaH (8 mg, 0.33 mmol) at 0° C. and the mixture was stirred for 30 min at rt under argon. The mixture was then cooled to 0° C. and 14a (25 mg, 0.06 mmol) was added and stirred for 2 h at rt. The reaction mixture was quenched by addition of ice and NaOH (0.5 mL, 2N) solution and then partitioned between water and EtOAc. Following filtration through anhydrous $Na_2SO_4$ and concentration, the crude mixture was purified by column chromatography using silica gel (5% MeOH/DCM) to get 17a (UH15_1) as yellow solid.

6-(2,4-dichlorophenyl)-2-44-(2-(diethylamino)ethoxy)phenyl)amino)-8-methylpyrido[2,3-d]pyrimidin-7(8H)-one (17a) UH15_1:

Yield 74%, yellow solid; $_1$H NMR (400 MHz, $CDCl_3$) δ (ppm) 8.54 (s, 1H), 7.55 (d, J=7.8 Hz, 4H), 7.49 (s, 1H), 7.30 (s, 2H), 6.94 (d, J=9.2 Hz, 2H), 4.07 (t, J =6.2 Hz, 2H), 3.75 (s, 3H), 2.89 (t, J=6.2 Hz, 2H), 2.65 (q, J=7.2 Hz, 4H), 1.08 (t, J=7.1 Hz, 6H). $^{13}$C NMR (100 MHz, $CDCl_3$) δ 162.16, 159.40, 158.60, 155.90, 155.59, 135.75, 134.69, 134.66, 133.75, 132.57, 131.55, 129.68, 127.09, 126.51, 122.05, 114.97, 106.38, 66.92, 51.82, 47.90, 28.62, 11.90. HRMS m/z calculated for $C_{26}H_{27}Cl_2N_5O_2$ [M+H]$^{30}$; 512.1615; found 512.1626; purity 95.6% ($t_R$ 21.56 min).

6-(2-chlorophenyl)-2-44-(2-(diethylamino)ethoxy)phenyl)amino)-8-methylpyrido2,3-d]pyrimidin-7(8H)-one (17b) UH15_2:

16a (40 mg, 0.17 mmol) and 14b (89 mg, 0.25 mmol) were used to make 17b.

Yield 62%, yellow solid; $^1$H NMR (400 MHz, $CDCl_3$) δ (ppm) 8.53 (s, 1H), 7.55 (d, J=6.9 Hz, 3H), 7.49-7.44 (m, 1H), 7.38-7.28 (m, 3H), 6.94 (d, J=8.7 Hz, 2H), 4.07 (t, J=6.4 Hz, 2H), 3.75 (s, 3H), 2.89 (t, J=6.2 Hz, 2H), 2.65 (q, J=7.2 Hz, 4H), 1.08 (t, J=7.3 Hz, 6H). $^{13}$C NMR (100 MHz, $CDCl_3$) δ 162.34, 159.34, 158.47, 155.86, 155.46, 135.49, 135.24, 133.91, 131.74, 129.80, 129.55, 127.79, 126.77, 122.02, 114.95, 106.51, 66.88, 51.83, 47.89, 28.61, 11.90. HRMS m/z calculated for $C_{26}H_{28}ClN_5O_2$ [M+H]$^+$: 478.2004; found 478.2007; purity 99.15% ($t_R$ 19.93 min).

2-44-(2-(diethylamino)ethoxy)phenyl)amino)-8-methyl-6-phenylpyrido[2,3-d]pyrimidin-7(8H)-one (17c) UH15_3:

16a (40 mg, 0.17 mmol) and 14c (20 mg, 0.06 mmol) were used to make 17c.

Yield 64%, yellow solid; $^1$H NMR (400 MHz, $CDCl_3$) δ (ppm) 8.55 (s, 1H), 7.68-7.63 (m, 3H), 7.56 (d, J=8.7 Hz, 2H), 7.45-7.33 (m, 3H), 6.94 (td, J=6.2, 4.1 Hz, 2H), 4.12 (t, J=6.2 Hz, 2H), 3.77 (s, 3H), 2.96 (t, J=6.2 Hz, 2H), 2.73 (q, J=7.2 Hz, 4H), 1.13 (t, J=7.1 Hz, 6H). $^{13}$C NMR (100 MHz, $CDCl_3$) δ 162.96, 159.06, 158.29, 155.43, 155.21, 136.22, 133.30, 131.90, 129.22, 128.88, 128.34, 128.18, 121.90, 114.97, 107.13, 66.44, 51.70, 47.81, 28.60, 11.51. HRMS m/z calculated for $C_{26}H_{29}N_5O_2$ [M+H]$^+$: 444.2394; found 444.2397; purity 99.4% ($t_R$ 19.75 min).

2-44-(2-(diethylamino)ethoxy)phenyl)amino)-8-ethyl-6-phenylpyrido[2,3-d]pyrimidin-7(8H)-one (17i) UH15_4:

16a (30 mg, 0.13 mmol) and 14i (40 mg, 0.12 mmol) were used to make 17i.

Yield 54%, yellow solid; $^1$H NMR (400 MHz, $CDCl_3$) δ (ppm) 8.56 (s, 1H), 7.67 (d, J=3.6 Hz, 2H), 7.64 (s, 1H), 7.56 (d, J=9.2 Hz, 2H), 7.46-7.30 (m, 3H), 6.94 (d, J=8.8 Hz, 2H), 4.50 (q, J=7.0 Hz, 2H), 4.07 (t, J=6.2 Hz, 2H), 2.90 (t, J=6.2 Hz, 2H), 2.66 (q, J=7.0 Hz, 4H), 1.38 (t, J=7.1 Hz, 3H), 1.09 (t, J=7.1 Hz, 6H). HRMS m/z calculated for $C_{27}H_{31}N_5O_2$ [M+H]$^+$: 458.2551; found 458.2556. purity 95.8% ($t_R$ 20.50 min).

2-44-(2-(diethylamino)ethoxy)phenyl)amino)-8-(2-hydroxyethyl)-6-phenylpyrido[2,3-d]pyrimidin-7(8H)-one (17j) UH15_5:

16a (30 mg, 0.13 mmol) and 14j (44 mg, 0.13 mmol) were used to make 17j.

Yield 33%, yellow solid; $^1$H NMR (600 MHz, $CD_3OD$) δ (ppm) 8.70 (s, 1H), 7.88 (s, 1H), 7.68 (d, J=7.8 Hz, 2H), 7.64 (d, J=7.8 Hz, 2H), 7.41 (t, J=7.5 Hz, 2H), 7.35 (d, J=7.5 Hz, 1H), 7.01 (d, J=9Hz, 2H), 4.63 (t, J=6.3 Hz, 2H), 4.27 (t, J=4.8 Hz, 2H), 3.89 (t, J=6.6 Hz, 2H), 3.37-3.34 (m, 2H), 3.13-3.12 (m, 4H), 1.28 (t, J=7.2 Hz, 6H). HRMS m/z calculated for $C_{27}H_{31}N_5O_3$ [M+H]$^+$: 474.2500; found 474.2504.

6-(2,6-dichlorophenyl)-2-44-(2-(diethylamino)ethoxy)phenyl)amino)-8-(2-methoxyethyl)pyrido[2,3-d]pyrimidin-7(8H)-one (17k) UH15_6:

16a (22 mg, 0.09 mmol) and 14k (20 mg, 0.05 mmol) were used to make 17k.

Yield 61%, yellow solid; $^1$H NMR (400 MHz, $CDCl_3$) δ (ppm) 8.56 (s, 1H), 7.56-7.52 (m, 3H), 7.41 (d, J=8 Hz, 3H), 7.28-7.24 (m, 1H), 6.94 (d, J=9.2 Hz, 2H), 4.67 (t, J=6 Hz, 2H), 4.07 (t, J=6.4 Hz, 2H), 3.76 (t, J=6.2 Hz, 2H), 3.37 (s, 3H), 2.90 (t, J=6.2 Hz, 2H), 2.66 (q, J=7.2 Hz, 4H), 1.63 (t, J=7.2 Hz, 6H). $^{13}$C NMR (100 MHz, $CDCl_3$) δ 161.25, 159.52, 158.79, 155.92, 155.61, 136.66, 135.81, 134.23, 131.56, 129.92, 128.11, 125.75, 122.23, 114.94, 106.44, 69.09, 66.87, 58.95, 51.82, 47.89, 40.44, 11.89. HRMS m/z calculated for $C_{28}H_{31}Cl_2N_5O_3$ [M+H]$^+$: 556.1877; found 556.1879; purity 97.4% ($t_R$ 20.76 min).

8-benzyl-6-(2,6-dichlorophenyl)-2-44-(2-(diethylamino)ethoxy)phenyeamino)pyrido[2,3-d]pyrimidin-7(8H)-one (171) UH15_7:

16a (16 mg, 0.07 mmol) and 141 (32 mg, 0.07 mmol) were used to make 171.

Yield 68%, yellow solid; $^1$H NMR (400 MHz, $CDCl_3$) δ (ppm) 8.54 (s, 1H), 7.53 (s, 1H), 7.44-7.19 (m, 10H), 6.91 (d, J=9.2 Hz, 2H), 5.60 (s, 2H), 4.08 (t, J=6.4 Hz, 2H), 2.90 (t, J=6.2 Hz, 2H), 2.67 (q, J=7.2 Hz, 4H), 1.09 (t, J=7.3 Hz, 6H). $^{13}$C NMR (100 MHz, $CDCl_3$) δ 161.44, 159.74, 158.78, 155.87, 155.74, 137.01, 136.72, 135.83, 134.30, 131.30, 129.95, 128.41, 128.22, 128.13, 127.32, 125.88, 123.12, 114.91, 106.45, 66.86, 51.83, 47.90, 44.47, 11.87. HRMS m/z calculated for $C_{32}H_{31}Cl_2N_5O_2$ [M+H]$^+$: 588.1928; found 588.1932; purity 98.4% ($t_R$ 22.59 min).

6-(4-chlorophenyl)-2-44-(2-(diethylamino)ethoxy)phenyl)amino)-8-methylpyrido[2,3-d]pyrimidin-7(8H)-one (17d) UH15_8:

16a (19 mg, 0.08 mmol) and 14d (28 mg, 0.08 mmol) were used to make 17d.

Yield 45%, yellow solid; $^1$H NMR (400 MHz, $CDCl_3$) δ (ppm) 8.56 (s, 1H), 7.62-7.60 (m, 3H), 7.54 (d, J=8.8 Hz, 2H), 7.38 (d, J=8.8 Hz, 2H), 6.94 (d, J=8.8 Hz, 2H), 4.07 (t, J=6.2 Hz, 2H), 3.75 (s, 3H), 2.89 (t, J=6.2 Hz, 2H), 2.66 (q, J=7.2 Hz, 4H), 1.08 (t, J=7.3 Hz, 6H). $^{13}$C NMR (100 MHz, $CDCl_3$) δ 162.73, 159.14, 158.38, 155.46, 155.38, 134.62, 134.05, 133.31, 131.73, 130.15, 128.47, 127.83, 121.96, 114.98, 106.95, 66.64, 51.74, 47.81, 28.60, 11.65. HRMS m/z calculated for $C_{26}H_{28}ClN_5O_2$ [M+H]$^+$: 478.2004; found 478.2010; purity 96.5% ($t_R$ 21.33 min).

6-(4-(tert-butyl)phenyl)-2-((4-(2-(diethylamino)ethoxy)phenyl)amino)-8-methylpyrido[2,3-d]pyrimidin-7(8H)-one (17e) UH15_9:

16a (32 mg, 0.14 mmol) and 14e (50 mg, 0.14 mmol) were used to make 17e.

Yield 58%, yellow solid; $^1$H NMR (400 MHz, $CDCl_3$) δ (ppm) 8.54 (s, 1H), 7.63-7.59 (m, 3H), 7.56 (d, J=8.8 Hz, 2H), 7.45 (d, J=8.4 Hz, 2H), 6.94 (d, J=8.8 Hz, 2H), 4.07 (t, J=6.4 Hz, 2H), 3.76 (s, 3H), 2.89 (t, J=6.4 Hz, 2H), 2.65 (q, J=7.2 Hz, 4H), 1.35 (s, 9H), 1.08 (t, J=7.1 Hz, 6H). $^{13}$C NMR (100 MHz, CDCl$_3$) δ 163.08, 159.02, 158.15, 155.41, 155.36, 151.19, 133.27, 132.81, 131.82, 129.11, 128.52, 125.34, 121.87, 114.96, 107.18, 66.91, 51.84, 47.91, 34.74, 31.41, 28.59, 11.92. HRMS m/z calculated for C$_{30}$H$_{37}$N$_5$O$_2$ [M+H]$^+$: 500.3020; found 500.3028; purity 99.8% ($t_R$ 23.44 min).

6-(2,6-dichlorophenyl)-2-44-(2-(diethylamino)ethoxy) phenyl)amino)-8-isobutylpyrido[2,3-d]pyrimidin-7(8H)-one (17m) UH15_10:

16a (23 mg, 0.09 mmol) and 14m (42 mg, 0.09 mmol) were used to make 17m

Yield 36%, yellow solid; $^1$H NMR (400 MHz, CDCl$_3$) δ (ppm) 8.55 (s, 1H), 7.84 (s, 1H), 7.58 (d, J=9.2 Hz, 2H), 7.50 (s, 1H), 7.40 (d, J=7.8 Hz, 2H), 7.25 (dd, J=8.5, 7.6 Hz, 1H), 6.94 (d, J=9.2 Hz, 2H), 4.29 (d, J=7.3 Hz, 2H), 4.08 (t, J=6.2 Hz, 2H), 2.91 (t, J=6.2 Hz, 2H), 2.67 (q, J=7.0 Hz, 4H), 2.42-2.32 (sep, J=6.8, 7.2 Hz, 1H), 1.09 (t, J=7.1 Hz, 6H), 0.98 (d, J=6.4 Hz, 6H). $^{13}$C NMR (100 MHz, CDCl$_3$) δ 161.60, 159.35, 158.63, 155.95, 155.43, 136.28, 135.79, 134.45, 131.81, 129.86, 128.08, 125.95, 121.97, 114.85, 106.32, 66.83, 51.82, 48.30, 47.90, 27.43, 20.36, 11.83. HRMS m/z calculated for C$_{29}$H$_{33}$Cl$_2$N$_5$O$_2$ [M+H]$^+$: 554.2084; found 554.2085.

6-(2,6-dichlorophenyl)-8-methyl-2-((3-(methylsulfonyl) phenyl)amino)pyrido[2,3-d]pyrimidin-7(8H)-one (17f) UH15_11:

16c (21 mg, 0.11 mmol) and 14f (20 mg, 0.05 mmol) were used to make 17f.

Yield 92%, white solid; $^1$H NMR (400 MHz, CDCl$_3$) δ (ppm) 8.69 (d, J=14.2 Hz, 2H), 8.23 (s, 1H), 7.83 (d, J=8 Hz, 1H), 7.66 (d, J=7.2 Hz, 1H), 7.61-7.55 (m, 2H), 7.41 (8 Hz, 2H), 7.31-7.25 (m, 1H), 3.86 (s, 3H), 3.11 (s, 3H). $^{13}$C NMR (100 MHz, CDCl$_3$) δ 161.38, 158.67, 158.58, 155.91, 141.45, 140.02, 136.19, 135.69, 134.00, 130.18, 130.15, 128.15, 127.16, 124.08, 121.57, 118.06, 107.33, 44.63, 28.98. HRMS m/z calculated for C$_{21}$H$_{16}$Cl$_2$N$_4$O$_3$S [M+H]$^+$: 475.0393; found 475.0393. purity 98.2% ($t_R$ 22.98 min).

6-(2,6-dichlorophenyl)-8-methyl-2-((4-(methylsulfonyl) phenyl)amino)pyrido[2,3-d]pyrimidin-7(8H)-one (17f*) UH15_12:

16b (11 mg, 0.05 mmol) and 14f (10 mg, 0.03 mmol) were used to make 17f*.

Yield 75%, white powder; $^1$H NMR (400 MHz, CDCl$_3$) δ (ppm) 8.67 (s, 1H), 7.99-7.91 (m, 4H), 7.78 (s, 1H), 7.79 (s, 1H), 7.42 (d, J=7.8 Hz, 2H), 7.32-7.28 (m, 1H), 3.83 (s, 3H), 3.09 (s, 3H). $^{13}$C NMR (100 MHz, CDCl$_3$) δ 161.29, 158.52, 158.48, 155.90, 143.77, 136.11, 135.66, 134.06, 133.90, 130.21, 128.99, 128.18, 127.55, 119.04, 107.69, 44.90, 28.89. HRMS m/z calculated for C$_{21}$H$_{16}$Cl$_2$N$_4$O$_3$S [M+H]$^+$: 475.0393; found 475.0397; purity 97.6% ($t_R$ 22.92 min).

6-(4-chlorophenyl)-8-methyl-2-43-(methylsulfonyl)phenyl)amino)pyrido12,3-dlpyrimidin-7(8H)-one (17d*) UH15-13:

16c (29 mg, 0.15 mmol) and 14d (26 mg, 0.07 mmol) were used to make 17d*.

Yield 61%, light yellow powder; $^1$H NMR (400 MHz, DMSO-d6) δ (ppm) 10.61 (s, 1H), 8.91 (s, 1H), 8.79 (s, 1H), 8.12 (s, 1H), 7.96 (d, J=8 Hz, 1H), 7.74 (d, J=8.8 Hz, 2H), 7.67-7.56 (m, 2H), 7.51 (d, J=8.8 Hz, 2H), 3.71(s, 3H), 3.23 (s, 3H). HRMS m/z calculated for C$_{21}$H$_{17}$ClN$_4$O$_3$S [M+H]$^+$: 441.0783; found 441.0781.

6-(4-chlorophenyl)-8-isobutyl-2-43-(methylsulfonyl)phenyl)amino)pyrido[12,3-d]pyrimidin-7(8H)-one (17n) UH15_14:

16c (15 mg, 0.07 mmol) and 14n (20 mg, 0.05 mmol) were used to make 17n.

Yield 33%, light yellow solid; $^1$H NMR (400 MHz, CDCl$_3$) δ (ppm) 8.66 (s, 1H), 8.32 (t, J=1.8 Hz, 1H), 8.05 (d, J=8.2 Hz, 1H), 7.74 (s, 1H), 7.71-7.56 (m, 5H), 7.41 (d, J=8.8 Hz, 2H), 4.38 (d, J=7.2 Hz, 2H), 3.11 (s, 3H), 2.40-2.30 (sep, J=6.8, 8.4 Hz, 1H), 0.99 (d, J=6.4 Hz, 6H). HRMS m/z calculated for C$_{24}$H$_{23}$ClN$_4$O$_3$S [M+H]$^+$: 483.1252; found 483.1261.

6-(2-chlorophenyl)-8-methyl-2-43-(methylsulfonyl)phenyl)amino)pyrido12,3-dlpyrimidin-7(8H)-one (17b*) UH15_15:

16c (34 mg, 0.17 mmol) and 14b (50 mg, 0.14 mmol) were used to make 17b*.

Yield 72%, white solid; $^1$H NMR (500 MHz, CDCl$_3$) δ (ppm) 8.71 (s, 1H), 8.65 (s, 1H), 7.79 (d, J=8 Hz, 2H), 7.65 (t, J=9 Hz, 2H), 7.58 (t, J=7.8 Hz, 1H), 7.50-7.47 (m, 1H), 7.38-7.32 (m, 3H), 3.85 (s, 3H), 3.10 (s, 3H). HRMS m/z calculated for C$_{21}$H$_{17}$ClN$_4$O$_3$S [M+H]$^+$: 441.0783; found 441.0784; purity 98.1% ($t_R$ 22.36 min).

6-(2,4-dichlorophenyl)-8-methyl-24(3-(methylsulfonyl)phenyl)amino)pyrido12,3-dlpyrimidin-7(8H)-one (17a*) UH15_16:

16c (8 mg, 0.04 mmol) and 14a (12 mg, 0.03 mmol) were used to make 17a*.

Yield 63%, light yellow solid; $^1$H NMR (500 MHz, CDCl$_3$) δ (ppm) 8.70 (s, 1H), 8.65 (s, 1H), 7.78 (d, J=6.5 Hz, 2H), 7.67-7.56 (m, 3H), 7.50 (s, 1H), 7.32 (s, 2H), 3.84 (s, 3H), 3.10 (s, 3H). $^{13}$C NMR (125 MHz, CDCl$_3$) δ 161.97, 158.59, 158.56, 155.76, 141.56, 139.89, 135.45, 134.94, 134.64, 133.43, 132.49, 130.20, 129.75, 128.05, 127.18, 123.96, 121.65, 117.99, 107.38, 44.60, 28.97. HRMS m/z calculated for C$_{21}$H$_{16}$Cl$_2$N$_4$O$_3$S [M+H]$^+$: 475.0393; found 475.0400; purity 99.5% ($t_R$ 24.04 min).

6-(2,3-dichlorophenyl)-8-methyl-24(3-(methylsulfonyl)phenyl)amino)pyrido2,3-dlpyrimidin-7(8H)-one (17g) UH15_17:

16c (16 mg, 0.08 mmol) and 14g (25 mg, 0.06 mmol) were used to make 17g.

Yield 68%, light yellow solid; IH NMR (600 MHz, DMSO-d6) δ (ppm) 10.68 (s, 1H), 8.93 (s, 1H), 8.81 (s, 1H), 8.00 (m, 2H), 7.74 (d, J=7.8 Hz, 1H), 7.67 (t, J=8.1 Hz, 1H), 7.624 (d, J=8.4 Hz, 1H), 7.49 (t, J=7.8 Hz, 1H), 7.44 (d, J=7.8 Hz, 1H), 3.73 (s, 3H), 3.27 (s, 3H). $^{13}$C NMR (150 MHz, DMSO-d6) 6 161.41, 159.87, 159.18, 155.60, 141.87, 141.02, 138.53, 136.36, 132.29, 131.90, 131.03, 130.75, 130.39, 128.68, 127.61, 124.39, 120.95, 117.61, 106.87, 44.19, 28.75. HRMS m/z calculated for C$_{21}$H$_{16}$Cl$_2$N$_4$O$_3$S [M+H]$^{30}$ : 475.0393; found 475.0397; purity 98.5% ($t_R$ 23.50 min).

6-(2-chloro-4-fluorophenyl)-8-methyl-24(3-(methylsulfonyl)phenyl)amino)pyrido2,3-dlpyrimidin-7(8H)-one (17h) UH15_18:

16c (11 mg, 0.05 mmol) and 14h (20 mg, 0.04 mmol) were used to make 17h.

Yield 60%, white solid; $_1$H NMR (600 MHz, DMSO-d6) δ (ppm) 10.67 (s, 1H), 8.94 (s, 1H), 8.81 (s, 1H), 7.67 (t, J=8.1 Hz, 1H), 7.63-7.60 (m, 2H), 7.53-7.50 (m, 1H), 7.36 (td, J=8.5, 3 Hz, 1H), 3.73 (s, 3H), 3.27 (s, 3H). $^{13}$C NMR (150 MHz, DMSO-d6) δ 162.95, 161.68, 161.31, 159.77, 159.15, 155.56, 141.87, 141.04, 136.63, 134.58, 134.51, 133.87, 132.53, 130.39, 126.80, 124.37, 120.92, 117.59, 117.19, 117.02, 114.88, 114.73, 106.93, 44.18, 28.75. HRMS m/z calculated for C$_{21}$H$_{16}$ClFN$_4$O$_3$S [M+H]$^+$: 459.0688; found 459.0688; purity 97.6% ($t_R$ 22.72 min).

6-(2,5-dichlorophenyl)-8-methyl-2-((3-(methylsulfonyl)phenyl)amino)pyrido[2,3-d]pyrimidin-7(8H)-one (17o) UH15_19:

16c (6 mg, 0.03 mmol) and 14o (10 mg, 0.026 mmol) was used to make 17o.

Yield 92%, white solid; $^1$H NMR (400 MHz, DMSO-d6) δ (ppm) 10.65 (s, 1H), 8.89 (s, 1H), 8.77 (s, 1H), 7.98-7.95 (m, 2H), 7.65-7.56 (m, 3H), 7.53-7.50 (m, 2H), 3.68 (s, 3H), 3.22 (s, 3H). HRMS m/z calculated for $C_{21}H_{16}Cl_2N_4O_3S$ [M+H]$^+$: 475.0393; found 475.0390; purity 97.4% ($t_R$ 23.76 min).

6-(4-hydroxyphenyl)-8-methyl-2-((3-(methylsulfonyl) phenyl)amino)pyrido[2,3-d]pyrimidin-7(8H)-one (17p) UH15_21:

16c (22 mg, 0.11 mmol) and 14p (40 mg, 0.09 mmol) were used to make 17p.

Yield 79%, light yellow solid; $^1$H NMR (400 MHz, DMSO-d6) δ (ppm) 10.52 (s, 1H), 9.62 (s, 1H), 8.86 (s, 1H), 8.78 (s, 1H), 7.94-7.93 (m, 2H), 7.63-7.52 (m, 4H), 6.81 (d, J=8.8 Hz, 2H), 3.69 (s, 3H), 3.21 (s, 3H). HRMS m/z calculated for $C_{21}H_{18}N_4O_4S$ [M+H]$^+$: 423.1122; found 423.1120.

24(4-(2-(diethylamino)ethoxy)phenyl)amino)-6-(4-hydroxyphenyl)-8-methylpyrido[2,3-d]pyrimidin-7(8H)-one (17p*) UH15_22:

16a (20 mg, 0.081 mmol) and 14p (30 mg, 0.067 mmol) were used to make 17p*.

Yield 64%, light yellow solid; $^1$H NMR (400 MHz, CD$_3$OD) δ (ppm) 8.66 (s, 1H), 7.79 (s, 1H), 7.68 (d, J=9.2 Hz, 2H), 7.50 (d, J=8.8 Hz, 2H), 6.99 (d, J=9.2 Hz, 2H), 6.83 (d, J=8.8 Hz), 4.25 (t, J=5.2 Hz, 2H), 3.74 (s, 3H), 3.36-3.34 (m, 2H), 3.11 (q, J=7.2 Hz, 4H), 1.28 (t, J=7.4 Hz, 6H). HRMS m/z calculated for $C_{26}H_{29}N_5O_3$ [M+H]$^+$: 460.2343; found 460.2348.

6-(2,6-dichlorophenyl)-2-44-(2-(diethylamino)ethoxy) phenyl)amino)-8-(3-(methylsulfonyebenzyl)pyrido[2,3-d] pyrimidin-7(8H)-one (17q) UH15_26:

Yield 84%, light yellow solid; $^1$H NMR (600 MHz, CDCl$_3$) δ (ppm) 8.58 (s, 1H), 7.99 (s, 1H), 7.81 (d, J=7.8 Hz, 1H), 7.60-7.39 (m, 7H), 7.32-7.26 (m, 2H), 6.94 (d, J=9 Hz, 2H), 5.68 (s, 2H), 4.10 (t, J=5.7 Hz, 2H), 2.93-2.91 (m, 5H), 2.68 (q, J=7.2 Hz, 4H), 1.09 (t, J=7.2 Hz, 6H). HRMS m/z calculated for $C_{33}H_{33}Cl_2N_5O_4S$ [M+H]$^+$: 666.1703; found 666.1703; purity 95.6% ($t_R$ 21.35 min).

6-(2,6-dichlorophenyl)-2-44-(2-(diethylamino)ethoxy) phenyl)amino)-8-(4-(methylsulfonyebenzyl)pyrido[2,3-d] pyrimidin-7(8H)-one (17r) UH15_27:

Yield 70%, light yellow solid; $^1$H NMR (600 MHz, CDCl$_3$) δ (ppm) 8.58 (s, 1H), 7.81 (d, J=8.4 Hz, 2H), 7.57 (s, 1H), 7.49-7.36 (m, 6H), 7.29-7.26 (m, 2H), 6.92 (d, J=8.4 Hz, 2H), 5.64 (s, 2H), 4.08 (t, J=6.3 Hz, 2H), 3.00 (s, 3H), 2.91 (t, J=6 Hz, 2H), 2.67 (t, J=7.2 Hz, 4H), 1.09 (t, J=6.9 Hz, 6H). HRMS m/z calculated for $C_{33}H_{33}Cl_2N_5O_4S$ [M+H]$^+$: 666.1703; found 666.1716; purity 95.6% ($t_R$ 21.24 min).

6-(4-methoxyphenyl)-8-methyl-2-43-(methylsulfonyl) phenyl)amino)pyrido[2,3-d]pyrimidin-7(8H)-one (17s) UH15_29:

16c (12mg, 0.06 mmol) and 14s (20 mg, 0.05 mmol) were used to make 17s.

Yield 95%, yellow solid; $^1$H NMR (400 MHz, DMSO-d6) δ (ppm) 10.52 (s, 1H), 8.87-8.77 (m, 2H), 7.99-7.94 (m, 2H), 7.66-7.54 (m, 4H), 6.99 (d, J=8.4 Hz, 2H), 3.79 (s, 3H), 3.70 (s, 3H), 3.21 (s, 3H). HRMS m/z calculated for $C_{22}H_{20}N_4O_4S$ [M+H]$^+$: 437.1278; found 437.1282.

2-44-(2-(diethylamino)ethoxy)phenyl)amino)-6-(4-methoxyphenyl)-8-methylpyrido[2,3-d]pyrimidin-7(8H)-one (17s*) UH15_30:

16a (8 mg, 0.03 mmol) and 14s (14 mg, 0.03 mmol) were used to make 17s*.

Yield 66%, yellow solid; $^1$H NMR (400 MHz, CD$_3$OD) δ (ppm) 8.59 (s, 1H), 7.73 (s, 1H), 7.61 (d, J=8.4 Hz, 2H), 7.55 (d, J=8.8 Hz, 2H), 6.94-6.90 (m, 4H), 4.11 (t, J=5.4 Hz, 2H), 3.80 (s, 3H), 3.68 (s, 3H), 3.04 (t, J=5.2 Hz, 2H), 2.82 (q, J=7.2 Hz, 4H), 1.16 (t, J=7 Hz, 6H). HRMS m/z calculated for $C_{27}H_3N_5O_3$ [M+H]$^+$: 474.2500; found 474.2505.

Figure 16:
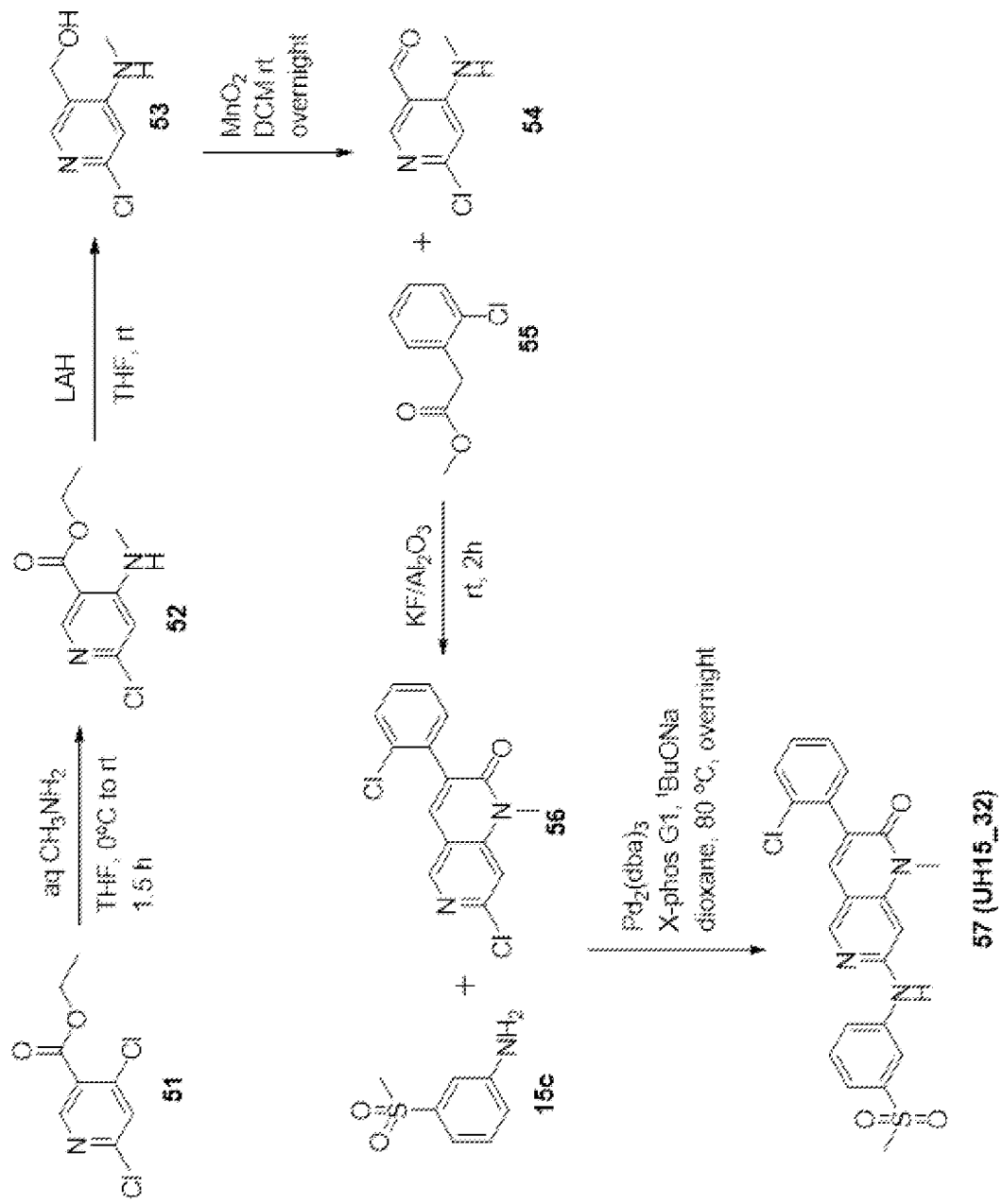
FIG. 16 shows a synthetic scheme for an exemplary inhibitor of protein kinase, in accordance with preferred embodiments.

Preparation of UH15_32:

FIG. 16 shows a synthetic scheme for an exemplary inhibitor of protein kinase, compound UH15_32, in accordance with preferred embodiments.

Ethyl 6-chloro-4-(methylamino)nicotinate (52):

To a solution of Ethyl 4,6-dichloronicotinate 51 (100mg, 0.45 mmol) in THF (3 mL) was added aqueous methyl amine (0.4 mL) at 0° C. and the mixture was stirred for 30 min at the same temperature. After 30 min the reaction mixture was stirred at room temperature for 2 h. Following completion the mixture was concentrated and purified by column chromatography using silica gel (10% EtOAc/ Hexane) to afford 52 (65 mg, 67%) as white solid. $^1$H NMR (400 MHz, CDCl$_3$) δ (ppm) 8.63 (s, 1H), 8.09 (brs, 1H), 6.51 (s, 1H), 4.31 (q, J=6.9 Hz, 2H), 2.89 (d, J=4.8 Hz, 3H), 1.36 (t, J=7 Hz, 3H). $^{13}$C NMR (100 MHz, CDCl$_3$) δ (ppm) 167.61, 156.82, 155.74, 152.86, 107.04, 104.36, 61.00, 29.21, 14.32.

(6-chloro-4-(methylamino)pyridin-3-yl)methanol (53):

The solution of 52 (100 mg, 0.46 mmol) in THF (2 mL) was added dropwise to the suspension of LAH (27 mg, 0.69 mmol) in THF (5 mL) at 0° C. and allowed to stir at room temperature for 30 min The reaction mixture was then cooled at 0° C. and 15% NaOH (2 mL) and water (4 mL) was added dropwise. The reaction mixture was allowed to stir for 1 h, filtered and washed with EtOAc. Solvent was evaporated and the extract was purified by column chromatography using silica gel (2.5% MeOH/DCM) to afford 53 (77mg, 96%) as white solid. $^1$H NMR (400 MHz, CD$_3$OD) δ (ppm) 7.73 (s, 1H), 6.51 (s, 1H), 4.91 (s, 2H), 4.49 (s, 2H), 2.84 (s, 3H). $^{13}$C NMR (100 MHz, CDCl$_3$) δ (ppm) 155.72, 151.09, 145.84, 119.71, 102.79, 59.01, 28.13.

6-chloro-4-(methylamino)nicotinaldehyde (54):

To a solution of 53 (495 mg, 2.86 mmol) in DCM (10 mL), was added MnO$_2$ (1496 mg, 17.20 mmol) and the mixture was allowed to stir overnight at room temperature. The reaction mixture was then filtered, concentrated to remove DCM and purified by column chromatography using silica gel (2% MeOH/DCM) to afford 54 (453 mg, 93%) as white solid. $^1$H NMR (400 MHz, CDCl$_3$) δ (ppm) 9.70 (s, 1H), 8.43 (brs, 1H), 8.16 (s, 1H), 6.43 (s, 1H), 2.83 (d, J=5.6 Hz, 3H).

7-chloro-3-(2-chlorophenyl)-1-methyl-1,6-naphthyridin-2(1H)-one (56):

To a stirred solution of 54 (300 mg, 1.75 mmol) and methyl 2-(2-chlorophenyl)acetate 55 (325 mg, 1.75 mmol) in dry DMA (4 mL), KF/Al$_2$O$_3$ (1800 mg, 40 wt %) was added and the reaction mixture was stirred at room temperature for 2 h. After completion the reaction mixture was filtered through celite and the residual solid was washed with DCM and filtrate was concentrated. The residue was purified by column chromatography using silica gel (20% EtOAc/Hexane) to give 56 (400 mg, 75%) as white solid. $^1$H NMR (400 MHz, CDCl$_3$) δ (ppm) 8.54 (s, 1H), 7.72 (s, 1H), 7.44-7.39 (m, 1H), 7.34-7.26 (m, 4H), 3.65 (s, 3H).

3-(2-chlorophenyl)-1-methyl-7-43-(methylsulfonyl)phenyl)amino)-1,6-naphthyridin-2(1H)-one (57) UH15_32:

To a pre-heated round bottom flask, 56 (30 mg, 0.09 mmol), 15c (20 mg, 0.11 mmol), Pd$_2$(dba)$_3$ (9 mg, 0.009 mmol), XPhos Pd G1 (9 mg, 0.02 mmol) and sodium tert-butoxide (28 mg, 0.29 mmol) was added and flushed with argon for 10 min. Dioxane (1.5 mL) was added to the mixture and flushed again for 5 min and then heated overnight at 80° C. Following completion, the reaction mixture was partitioned between ethyl acetate and water, filtered, concentrated and purified by column chromatography using silica gel (2% MeOH/DCM) to give 57 (UH15_32) (20 mg, 47%) as white solid. $^1$H NMR (400 MHz, CDCl$_3$) δ (ppm) 8.48 (s, 1H), 8.11 (t, J=1.8 Hz, 1H), 7.87 (d, J=8 Hz, 1H), 7.66 (s, 1H), 7.61-7.53 (m, 2H), 7.47-7.29 (m, 5H), 3.65 (s, 3H), 3.11 (s, 3H). $^{13}$C NMR (100 MHz, CDCl$_3$) δ (ppm) 161.45, 155.87, 149.98, 146.87, 141.54, 141.35, 136.97, 135.49, 133.89, 131.62, 130.52, 129.76, 129.58, 128.54, 126.80, 124.41, 120.82, 117.83, 111.72, 91.85, 44.61, 29.71. HRMS m/z calculated for C$_{22}$H$_{18}$ClN$_3$O$_3$S [M+H]$^+$: 440.0830; found 440.0837.

Preparation of UH15_33

Figure 17:
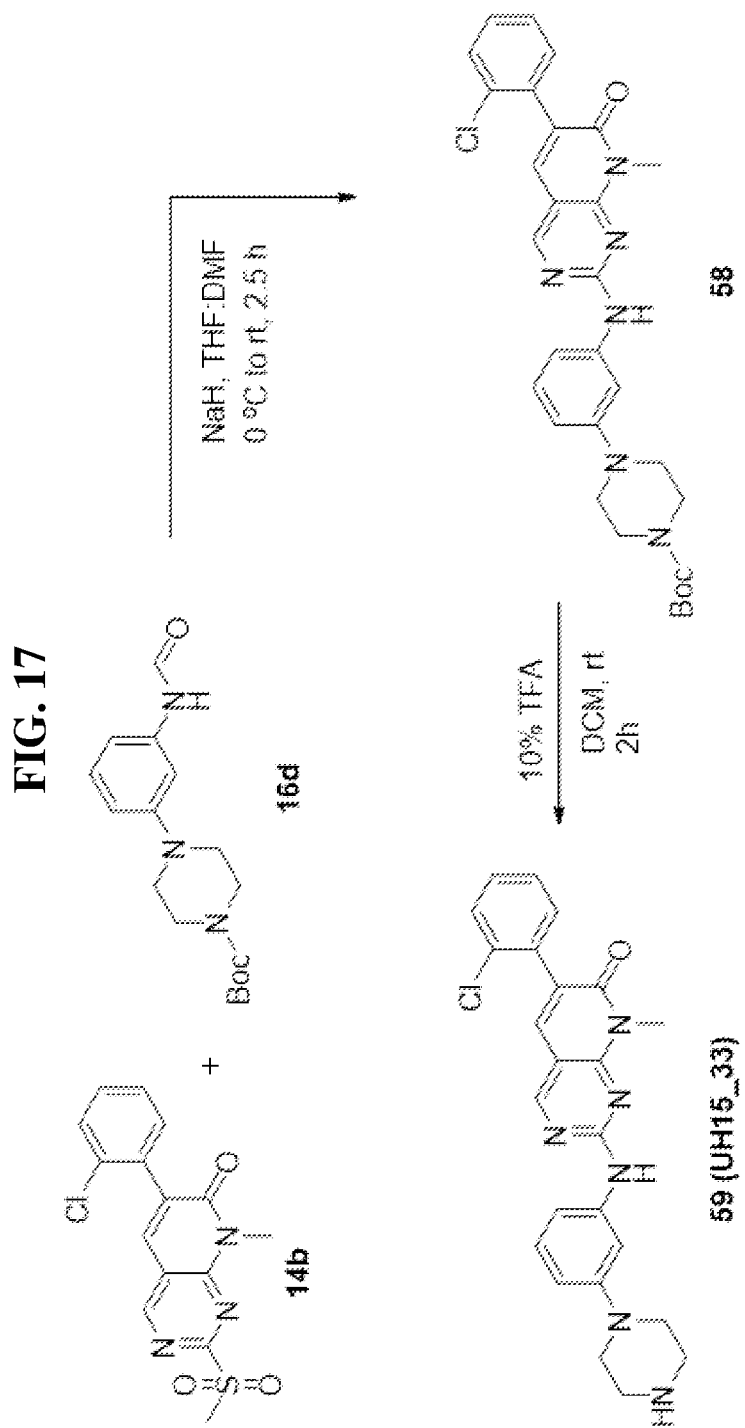
FIG. 17 shows a synthetic scheme for an exemplary inhibitor of protein kinase, in accordance with preferred embodiments.

FIG. 17 shows a synthetic scheme for an exemplary inhibitor of protein kinase, compound UH15_33, in accordance with preferred embodiments.

Tert-butyl 4-(3((6-(2-chlorophenyl)-8-methyl-7-oxo-7,8-dihydropyrido[2,3-d]pyrimidin-2-yl)amino)phenyl)piperazine-1-carboxylate (58):

14b (62 mg, 0.17 mmol) and 16d (54 mg, 0.17 mmol) were used to make 58.

Yield 70%, light yellow solid; $^1$H NMR (400 MHz, CDCl$_3$) δ (ppm) 8.57 (s, 1H), 7.58 (s, 2H), 7.49-7.46 (m, 1H), 7.42-7.41 (m, 1H), 7.37-7.27 (m, 4H), 7.14 (d, J=8.4 Hz, 1H), 6.69 (d, J=8 Hz, 1H), 3.79 (s, 3H), 3.59 (t, J=5 Hz, 4H), 3.19 (t, J=4.8 Hz, 4H), 1.48 (s, 9H). $^{13}$C NMR (100 MHz, CDCl$_3$) δ (ppm) 162.26, 159.03, 158.42, 155.77, 154.84, 152.11, 139.65, 135.42, 135.14, 133.89, 131.70, 129.83, 129.76, 129.63, 128.25, 126.80, 111.89, 111.71, 107.97, 106.77, 80.12, 49.41, 28.70, 28.53.

6-(2-chlorophenyl)-8-methyl-2-((3-(piperazin-1-yl)ophenyl)amino)pyrido[2,3-d]pyrimidin-7(8H)-one (59) UH15_33:

58 (67 mg, 0.12 mmol) was taken in DCM (4.5 mL) and TFA (0.5 mL) was added dropwise. The reaction mixture was stirred at room temperature for 2h. Solvent was evaporated and the crude mixture was purified by column chromatography using silica gel (4% MeOH/DCM) to give 59 (UH15_33) (55 mg, 96%) as light yellow solid. $^1$H NMR (600 MHz, DMSO-d6) δ (ppm) 8.76 (s, 1H), 7.80 (s, 1H), 7.50-7.48 (m, 2H), 7.40-7.34 (m, 3H), 7.24-7.21 (m, 2H), 6.70 (d, J=7.2 Hz, 1H), 3.61 (s, 3H), 3.32 (t, J=4.8 Hz, 4H), 3.21 (t, J=5.2 Hz, 4H). HRMS m/z calculated for C$_{24}$H$_{23}$ClN$_6$O [M+H]$^+$: 447.1695; found 447.1697.

6-(2-chlorophenyl)-8-methyl-2-(pyridin-3-ylamino) pyrido[2,3-d]pyrimidin-7(8H)-one (UH15_34):

14b (15 mg, 0.05 mmol) and 16f (6 mg, 0.05 mmol) were used to make UH15_34.

Yield 67%, white solid; $^1$H NMR (600 MHz, CDCl$_3$) δ (ppm) 8.87 (s, 1H), 8.61 (s, 1H), 8.37 (d, J=4.8 Hz, 1H), 8.23 (d, J=7.8 Hz, 1H), 7.73 (brs, 1H), 7.61 (s, 1H), 7.48-7.47 (m, 1H), 7.36-7.32 (m, 4H), 3.79 (s, 3H). $^{13}$C NMR (150 MHz, CDCl$_3$) δ (ppm) 162.15, 158.88, 158.42, 155.79, 144.45, 141.55, 135.64, 135.23, 134.97, 133.84, 131.64, 129.84, 129.72, 129.00, 126.80, 126.56, 123.66, 107.33, 28.79. HRMS m/z calculated for C$_{19}$H$_{14}$ClN$_5$O [M+H]$^+$: 364.0960; found 364.0960.

6-(2-chlorophenyl)-8-methyl-2-(pyridin-2-ylamino) pyrido[2,3-d]pyrimidin-7(8H)-one (UH15_35):

14b (20 mg, 0.06 mmol) and 16e (8 mg, 0.06 mmol) were used to make UH15_35.

Yield 62%, light yellow solid. $^1$H NMR (600 MHz, DMSO-d6) δ (ppm) 10.40 (s, 1H), 8.88 (s, 1H), 8.35-8.32 (m, 2H), 7.91 (s, 1H), 7.84 (t, J=7.6 Hz, 1H), 7.54 (d, J=7.8 Hz, 1H), 7.44-7.40 (m, 3H), 7.07 (t, J=6.3 Hz, 1H), 3.67 (s, 3H). HRMS m/z calculated for C$_{19}$H$_{14}$ClN$_5$O [M+H]$^+$: 364.0960; found 364.0960.

Figure 18A:
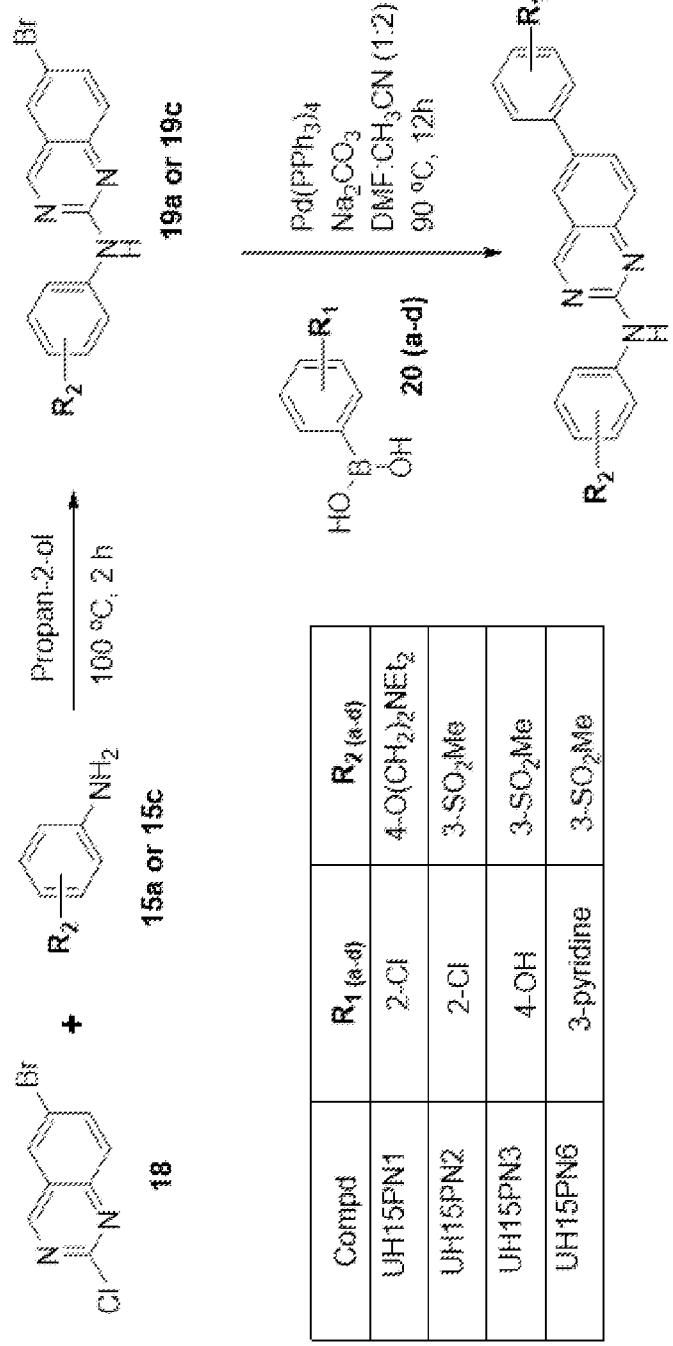
FIG. 18A shows a synthetic scheme for exemplary inhibitors of protein kinases, in accordance with preferred embodiments.
Figure 18B:
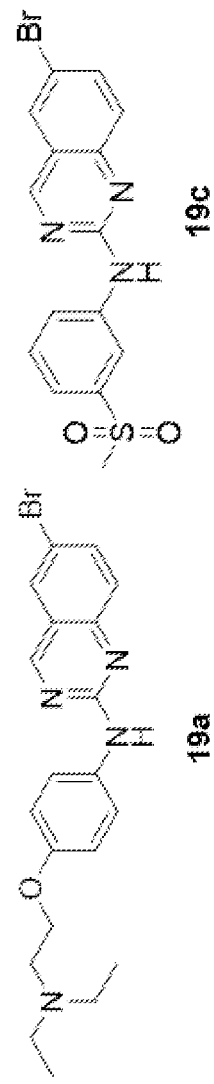
FIG. 18B shows structures of intermediate compounds used in the synthesis of exemplary inhibitors of protein kinases, in accordance with preferred embodiments.
Figure 19:
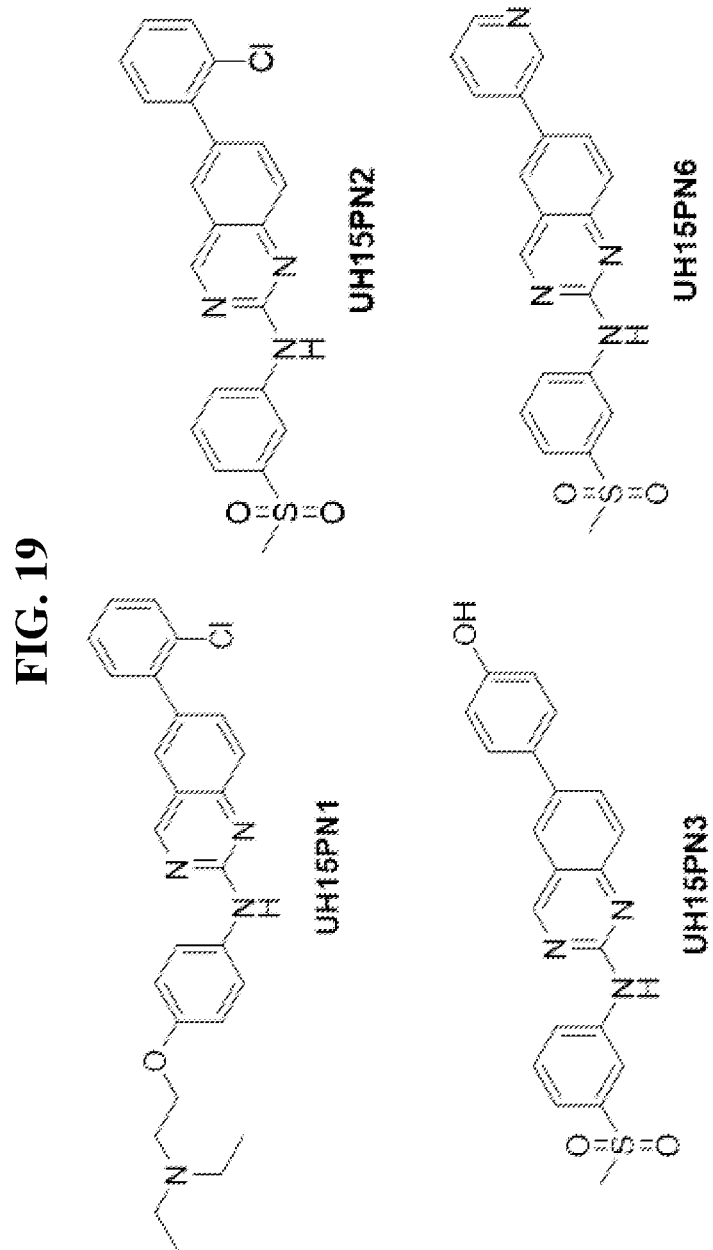
FIG. 19 shows structures of exemplary inhibitors of protein kinases, in accordance with preferred embodiments.

Preparation of UH15PN compounds:

FIG. 18A shows a synthetic scheme for exemplary inhibitors of protein kinases and FIG. 18B shows the structures of intermediate compounds used in the synthesis of these exemplary inhibitors of protein kinases, in accordance with preferred embodiments. FIG. 19 shows structures of exemplary inhibitors of protein kinases, in accordance with preferred embodiments.

6-bromo-N-(4-(2-(diethylamino)ethoxy)phenyl)quinazolin-2-amine (19a):

To a mixture of 6-bromo-2-chloroquinazoline (18) (200 mg, 0.82 mmol) and 15a (207 mg, 0.98 mmol), propan-2-ol (4 mL) was added and the reaction mixture was heated at 100° C. for 2 h. After completion, the reaction mixture was allowed to cool to room temperature and concentrated and purified by column chromatography using silica gel (5% MeOH/DCM) to afford 19 (203 mg, 61%) as yellow solid. $^1$H NMR (600 MHz, CDCl$_3$) δ (ppm) 8.94 (s, 1H), 7.81 (d, J=1.7 Hz, 1H), 7.74 (dd, J=9.3, 2.4 Hz, 1H), 7.65 (d, J=8.9 Hz, 2H), 7.61 (s, 1H), 7.54 (d, J=8.9 Hz, 1H), 6.94-6.90 (m, 2H), 4.08 (t, J=6.2 Hz, 2H), 2.91 (t, J=6.2 Hz, 2H), 2.68 (q, J=7.3 Hz, 4H), 1.09 (t, J=7.2 Hz, 6H). $^{13}$C NMR (150 MHz, CDCl$_3$) δ (ppm) 160.88, 157.30, 154.94, 150.50, 137.65, 132.51, 129.53, 128.04, 121.69, 121.40, 116.08, 114.98, 66.63, 51.74, 47.77, 11.68.

6-(2-chlorophenyl)-N-(4-(2-(diethylamino)ethoxy)phenyl)quinazolin-2-amine UH15PN1:

6-bromo-N-(4-(2-(diethylamino)ethoxy)phenyl)quinazolin-2-amine (19a) (30 mg, 0.07 mmol), (2-chlorophenyl) boronic acid (20a) (17 mg, 0.11 mmol) and Pd(PPh$_3$)$_4$ (8.5 mg, 0.007 mmol) was taken in round bottom flask (rb) and purged with argon for 10 min. DMF (1 mL) and CH$_3$CN (2 mL) solvent mixture were then added to the above reactants and was purged again for 10 min Following purging 1M Na$_2$CO$_3$ (150 µl) solution was added drop wise and started heating at 90° C. for 5 h. After completion the reaction mixture was allowed to cool to rt and solvent was evaporated. The residue was partitioned between water and EtOAc, filtered and concentrated to get a crude mixture which was purified by column chromatography using silica gel (5% MeOH/DCM) to get UH15PN1 (23 mg, 70%) as yellow solid. $^1$H NMR (600 MHz, CDCl$_3$) δ (ppm) 9.08 (s, 1H), 7.84 (dd, J=8.6, 1.7 Hz, 1H), 7.77-7.70 (m, 4H), 7.49 (d, J=8.4 Hz, 1H), 7.46 (s, 1H), 7.41 (dd, J=7.2, 1.7 Hz, 1H), 7.37-7.31 (m, 2H), 6.94 (d, J=9 Hz, 2H), 4.11 (t, J=6.2 Hz, 2H), 2.94 (t, J=6.2 Hz, 2H), 2.71 (q, J=7.1 Hz, 4H), 1.11 (t, J=7.2 Hz, 6H). $^{13}$C NMR (150 MHz, CDCl$_3$) δ (ppm) 162.11, 157.40, 154.76, 151.18, 139.41, 136.17, 134.63, 132.86, 132.69, 131.49, 130.21, 129.01, 127.97, 127.16, 125.77, 121.27, 120.45, 115.01, 66.56, 51.73, 47.78, 11.63.

6-bromo-N-(3-(methylsulfonyl)phenyl)quinazolin-2-amine (19c):

To a mixture of 6-bromo-2-chloroquinazoline (18) (100 mg, 0.41 mmol) and (15c) (85 mg, 0.49 mmol), propan-2-ol (2 mL) was added and the reaction mixture was heated at 100° C. for 2 h. After completion, the reaction mixture was cooled to rt, concentrated and purified by column chromatography using silica gel (2% MeOH/DCM) to afford 19c (150 mg, 97%) as light yellow solid. $^1$H NMR (600 MHz, DMSO-d6) δ (ppm) 10.46 (s, 1H), 9.37 (s, 1H), 8.71 (s, 1H), 8.25-8.22 (m, 2H), 7.97 (d, J=8.1 Hz, 1H), 7.65-7.60 (m, 2H), 7.55-7.54 (m, 1H), 3.23 (s, 3H).

6-(2-chlorophenyl)-N-(3-(methylsulfonyl)phenyl)quinazolin-2-amine (UH15PN2):

6-bromo-N-(3-(methylsulfonyl)phenyl)quinazolin-2-amine (19c) (50 mg, 0.08 mmol) and (2-chlorophenyl) boronic acid (20a) (31 mg, 0.12 mmol) were used to make UH15PN2 (31 mg, 95%) as yellow solid. $^1$H NMR (400 MHz, CDCl$_3$) δ (ppm) 9.19 (s, 1H), 8.63 (s, 1H), 8.11 (d, J=7.2 Hz, 1H), 7.92-7.89 (m, 1H), 7.85-7.83 (m, 3H), 7.64-7.51 (m, 3H), 7.44-7.34 (m, 3H), 3.13 (s, 3H) $^{13}$C NMR (100 MHz, CDCl$_3$) δ (ppm) 162.34, 156.51, 150.59, 141.27, 140.87, 139.17, 136.59, 135.81, 132.67, 131.49, 130.26, 130.10, 129.23, 127.99, 127.25, 126.21, 123.62, 120.93, 120.74, 117.34, 44.58

4-(2-((3-(methylsulfonyl)phenyl)amino)quinazolin-6-yl)phenol (UH15PN3):

19c (30 mg, 0.08 mmol) and (4-hydroxyphenyl)boronic acid (20c) (17 mg, 0.12 mmol) were used to make UH15PN3 (22 mg, 71%) as yellow solid. $^1$H NMR (400 MHz, DMSO-d6) δ (ppm) 10.33 (s, 1H), 9.66 (s, 1H), 9.38 (s, 1H), 8.72 (t, J=2 Hz, 1H), 8.23 (d, J=8.2 Hz, 1H), 8.15-8.12 (m, 2H), 7.71 (d, J=8.4 Hz, 1H), 7.63-7.58 (m, 3H), 7.52-7.49 (m, 1H), 6.89 (d, J=8.8 Hz, 2H), 3.22 (s, 3H).

Figure 20:
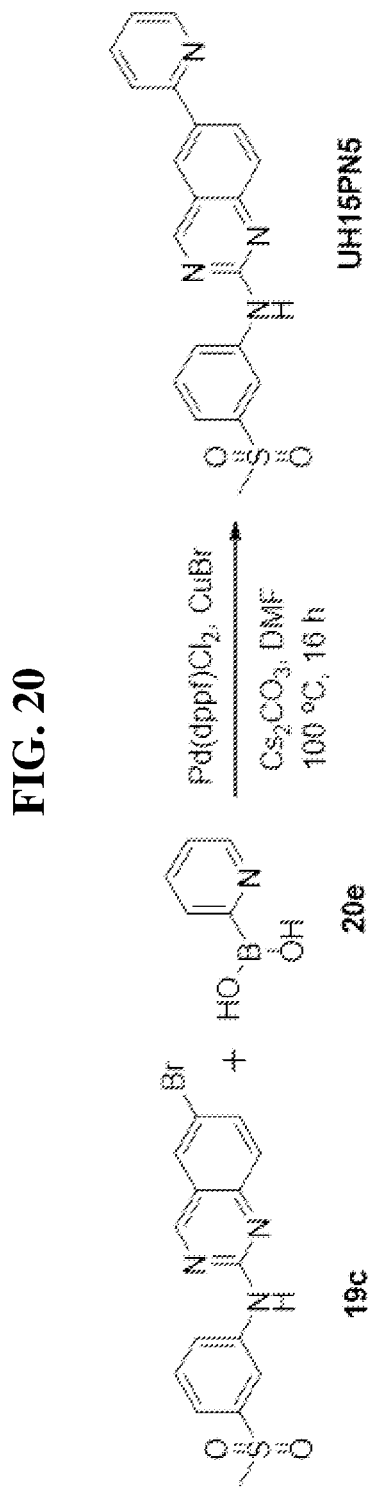
FIG. 20 shows a synthetic scheme for an exemplary inhibitor of protein kinase, in accordance with preferred embodiments.

N-(3-(methylsulfonyl)phenyl)-6-(pyridin-2-yl)quinazolin-2-amine (UH15PN5):

FIG. 20 shows a synthetic scheme for exemplary inhibitors of protein kinase UH15PN5, in accordance with preferred embodiments.

6-bromo-N-(3-(methylsulfonyl)phenyl)quinazolin-2-amine (19c) (20 mg, 0.05 mmol), pyridin-2-ylboronic acid (20e) (22 mg, 0.10 mmol), Pd(dppf)Cl$_2$ (4 mg, 0.005 mmol), CuBr (12 mg, 0.05 mmol) and Cs$_2$CO$_3$ (69 mg, 0.21 mmol) were taken in round bottom flask and purged with argon for 10 min DMF (2 mL) was then added to the above reactants and was purged again for 10 min Following purging, the contents were heated at 100° C. for 16 h. After completion the reaction mixture was allowed to cool to room temperature and solvent was evaporated. The residue was partitioned between water and EtOAc, filtered and concentrated to get a crude mixture which was purified by column chromatography using silica gel (2.5% MeOH/DCM) to get UH15PN5 (15 mg, 60%) as light brown solid. $^1$H NMR (600 MHz, DMSO-d6) δ (ppm) 10.42 (s, 1H), 9.47 (s, 1H), 8.73-8.71 (m, 3H), 8.61 (d, J=8.1 Hz, 1H), 8.25 (d, J=8.4 Hz, 1H), 8.10 (d, J=8.4 Hz, 1H), 7.96-7.93 (m, 1H), 7.77 (d, J=9 Hz, 1H), 7.61 (t, J=7.8 Hz, 1H), 7.53 (d, J=7.2 Hz, 1H), 7.40-7.38 (m, 1H), 3.23 (s, 3H).

N-(3-(methylsulfonyl)phenyl)-6-(pyridin-3-yl)quinazolin-2-amine (UH15PN6):

19c (30 mg, 0.08 mmol) and pyridin-3-ylboronic acid (20d) (15 mg, 0.12 mmol) were used to make UH15PN6 (15 mg, 50%) as yellow solid. 1H NMR (600 MHz, DMSO-d6) δ (ppm) 10. 42 (s, 1H), 9.43 (s, 1H), 9.03 (s, 1H), 8.72 (s, 1H), 8.60 (d, J=4.8 Hz, 1H), 8.37 (s, 1H), 8.27-8.25 (m, 2H), 8.22-8.20 (m, 1H), 7.79 (d, J=9 Hz, 1H), 7.61 (t, J=7.8 Hz, 1H), 7.55-7.52 (m, 2H), 3.23 (s, 3H).

Figure 21:
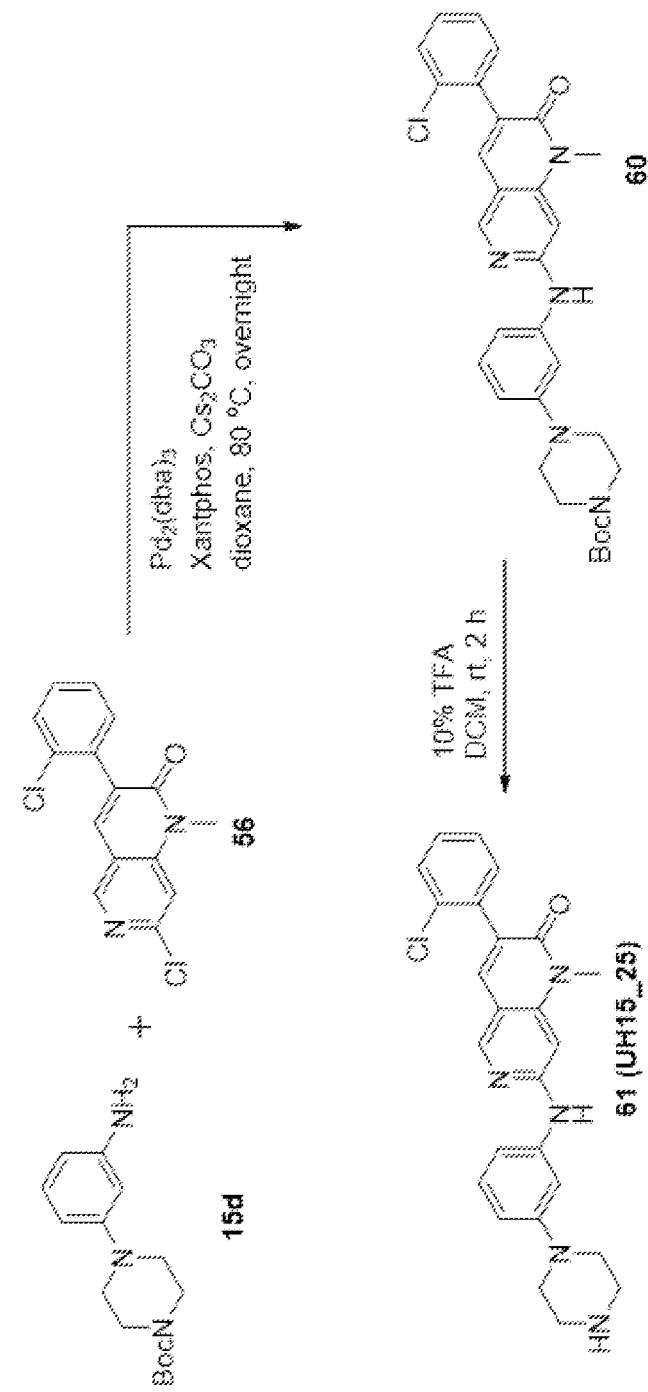
FIG. 21 shows a synthetic scheme for an exemplary inhibitor of protein kinase, in accordance with preferred embodiments.

Preparation of UH15_25:

FIG. 21 shows a synthetic scheme for an exemplary inhibitor of protein kinase UH15_25, in accordance with preferred embodiments.

Tert-butyl 4-(3-43-(2-chlorophenyl)-1-methyl-2-oxo-1,2-dihydro-1,6-naphthyridin-7-yl)amino)phenyl)piperazine-1-carboxylate (60):

To a pre-heated round bottom flask, 56 (20 mg, 0.065 mmol), 15d (22 mg, 0.078 mmol), Pd$_2$(dba)$_3$ (6 mg, 0.006 mmol), Xantphos (8 mg, 0.013 mmol) and caesium carbonate (43 mg, 0.13 mmol) was added and flushed with argon for 10 min Dioxane (1.5 mL) was added to the mixture and flushed again for 5 min and then heated overnight at 80° C. The reaction mixture was then partitioned between ethyl acetate and water, dried over anhydrous Na$_2$SO$_4$, filtered, concentrated and purified by column chromatography using silica gel (1.5% MeOH/DCM) to give 60 (20 mg, 57%) as light yellow solid.

3-(2-chlorophenyl)-1-methyl-7-43-(piperazin-l-yl)phenyl)amino)-1,6-naphthyridin-2(1H)-one (61) UH15_25:

60 (20 mg, 0.036 mmol) was taken in DCM (2 mL) and TFA (0.2 mL) was added dropwise. The reaction mixture was stirred at room temperature for 2 h. Solvent was evaporated, and the crude mixture was purified by column chromatography using silica gel (7% MeOH/DCM) to give 61 (UH15_25) (12 mg, 75%) as light yellow solid. $^1$H NMR (600 MHz, CD$_3$OD) δ (ppm) 8.47 (s, 1H), 7.76 (s, 1H), 7.48-7.47 (m, 1H), 7.37-7.36 (m, 3H), 7.31 (t, J=2 Hz, 1H), 7.23 (t, J=7.8 Hz, 1H), 7.06 (d, J=8.4 Hz, 1H), 6.72-6.70 (m, 2H), 3.61 (s, 3H), 3.33 (t, J=4.8 Hz, 4H), 3.23 (t, J=4.8 Hz, 4H).

Figure 22:
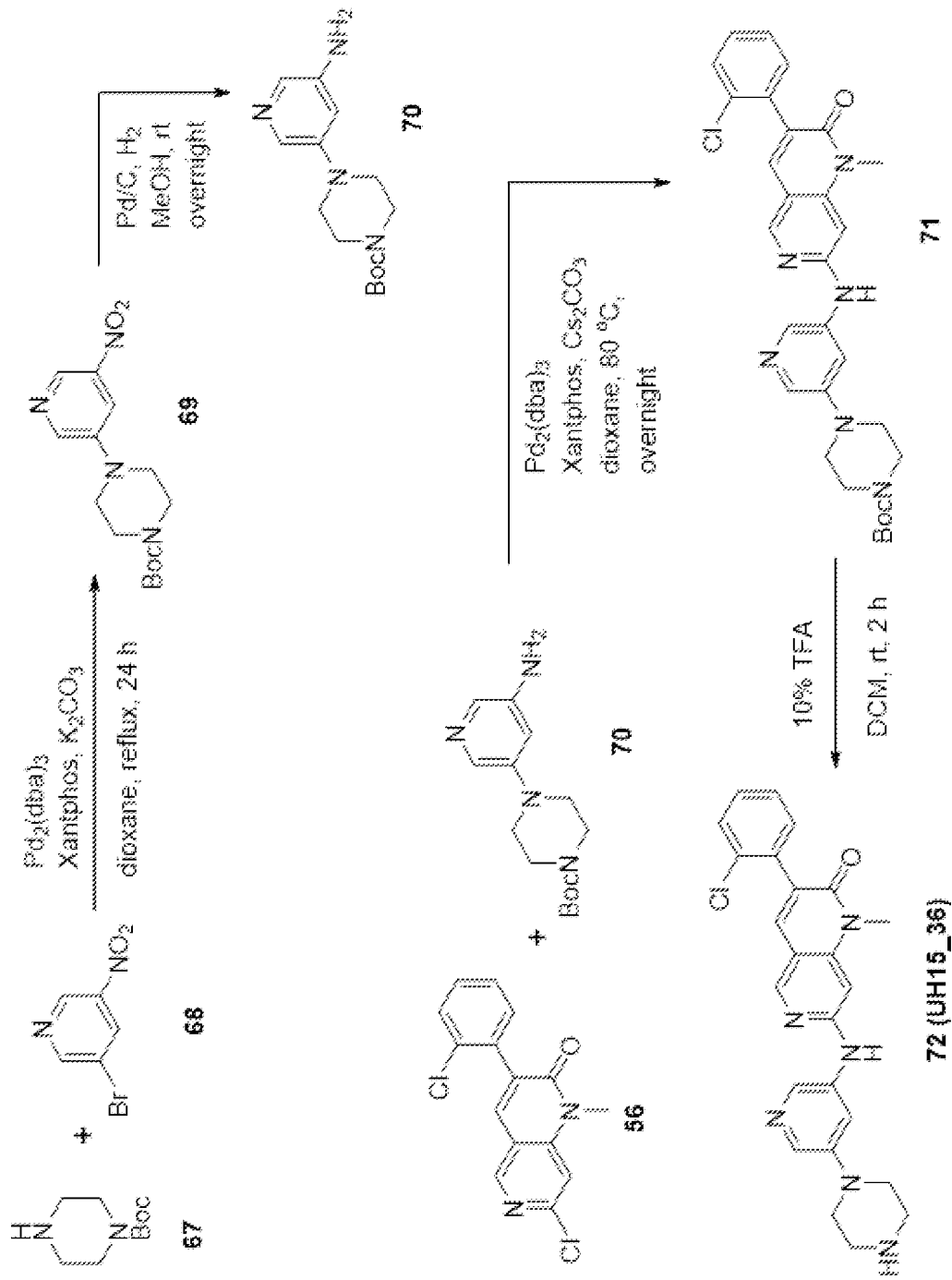
FIG. 22 shows a synthetic scheme for an exemplary inhibitor of protein kinase, in accordance with preferred embodiments.

Preparation of UH15_36:

FIG. 22 shows a synthetic scheme for exemplary inhibitor of protein kinase UH15_36, in accordance with preferred embodiments.

Tert-butyl 4-(5-nitropyridin-3-yl)piperazine-1-carboxylate (69):

To a pre-heated round bottom flask Pd$_2$(dba)$_3$ (125 mg, 0.13 mmol), Xantphos (155 mg, 0.26 mmol) and potassium carbonate (740 mg, 5.36 mmol) was added and flushed with argon for 10 min DMF (4 mL) was added to the mixture and flushed for another 5 min, which was followed by addition of 67 (500 mg, 2.68 mmol) and 68 (545 mg, 2.68 mmol) and then refluxed for 24 h. The reaction mixture was then partitioned between ethyl acetate and water, dried over anhydrous Na$_2$SO$_4$, filtered, concentrated and purified by column chromatography using silica gel (15% EtOAc/DCM) to give 69 (250 mg, 30%) as light yellow solid. $^1$H NMR (600 MHz, DMSO-d$_6$) δ (ppm) 8.72 (s, 1H), 8.69 (s, 1H), 7.94 (s, 1H), 3.46 (t, J=5 Hz, 4H), 3.35 (t, J=5H, 4H), 1.41 (s, 9H).

Tert-butyl 4-(5-aminopyridin-3-yl)piperazine-l-carboxylate (70):

To a solution of 69 (250 mg, 0.81 mmol) in CH$_3$OH (15 mL) was added 10% Pd/C (50 mg) and the reaction was stirred at room temperature in H$_2$ (g) (1 atm) for 4 h. The reaction mixture was then filtered through celite and concentrated to afford 70 (220 mg, 97%) as brown solid which was used in next step without purification.

Tert-butyl 4-(5-43-(2-chlorophenyl)-1-methyl-2-oxo-1,2-dihydro-1,6-naphthyridin-7-yl)amino)pyridin-3-yl)piperazine-1-carboxylate (71):

To a pre-heated round bottom flask, 56 (42 mg, 0.13 mmol), 70 (39 mg, 0.13 mmol), Pd$_2$(dba)$_3$ (13 mg, 0.013 mmol), Xantphos (16 mg, 0.027 mmol) and caesium carbonate (90 mg, 0.27 mmol) was added and flushed with argon for 10 min. Dioxane (3 mL) was added to the mixture and flushed again for 5 min and then heated overnight at 80° C. The reaction mixture was then partitioned between ethyl acetate and water, dried over anhydrous Na$_2$SO$_4$, filtered, concentrated and purified by column chromatography using silica gel (2.5% MeOH/DCM) to give 71 (26 mg, 35%) as light brown solid.

3-(2-chlorophenyl)-1-methyl-7-45-(piperazin-l-yl)pyridin-3-yl)amino)-1,6-naphthyridin-2(1H)-one (72) UH15_36:

71 (20 mg, 0.036 mmol) was taken in DCM (2 mL) and TFA (0.2 ml) was added dropwise. The reaction mixture was stirred at room temperature for 2 h. Solvent was evaporated, and the crude mixture was purified by reverse phase preparative HPLC (95% H$_2$O/CH$_3$CN with 0.1% TFA to 95% CH$_3$CN/H$_2$O with 0.1% TFA) to give 72 (UH15_36) (12 mg, 75%) as light yellow solid. $^1$H NMR (600 MHz, CD$_3$OD) δ (ppm) 9.00 (s, 1H), 8.65 (s, 1H), 8.17-8.10 (m, 2H), 7.87 (s, 1H), 7.51-7.38 (m, 4H), 6.87 (s, 1H), 3.69 (s, 3H), 3.67 (t, J=5 Hz, 4H), 3.43 (t, J=5 Hz, 4H). $^{13}$C NMR (150 MHz, CD3OD) δ (ppm) 161.59, 155.45, 149.42, 148.33, 146.44, 141.68, 137.33, 135.63, 133.69, 131.41, 129.49, 129.33, 129.23, 126.68, 122.48, 121.75, 116.21, 112.27, 93.67, 44.35, 42.71, 28.69.

Figure 23:
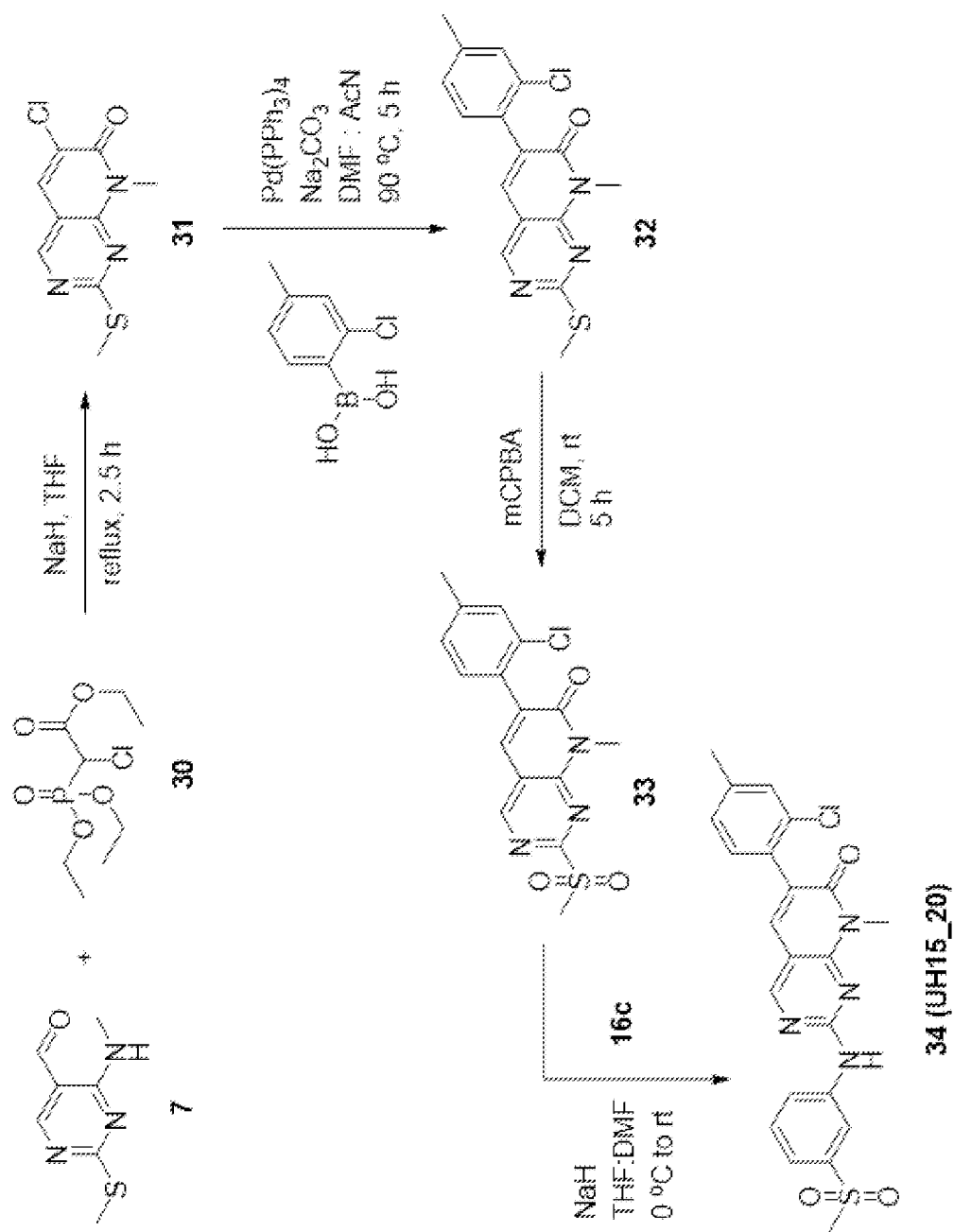
FIG. 23 shows a synthetic scheme for an exemplary inhibitor of protein kinase, in accordance with preferred embodiments.

Preparation of 34 (UH15_20):

FIG. 23 shows a synthetic scheme for exemplary inhibitor of protein kinase UH15_20, in accordance with preferred embodiments.

6-chloro-8-methyl-2-(methylthio)pyridol2,3-dlpyrimidin-7(8H)-one (31):

To a mixture of 7 (20 mg, 0.11 mmol) and NaH (8 mg, 0.33 mmol), THF (1.5 mL) was added and stirred at rt for 10 min under argon. The solution of ethyl 2-chloro-2-(diethoxyphosphoryl)acetate 30 (42 mg, 0.16 mmol) in THF (0.5 mL) was added dropwise and the mixture was refluxed for 2.5 h. After completion, the reaction mixture was cooled to rt, concentrated and extracted using EtOAc and water system. The organic solvent was evaporated and the residue was purified by column chromatography using silica gel (30% EtOAc/Hexane) to afford 31 (10 mg, 42%) as white solid. $^1$H NMR (600 MHz, CDCl$_3$) δ (ppm) 8.59 (s, 1H), 7.82 (s, 1H), 3.80 (s, 3H), 2.62 (s, 3H). $^{13}$C NMR (600 MHz, CDCl$_3$) δ (ppm) 173.60, 159.29, 155.69, 153.30, 132.58, 126.69, 108.98, 29.23, 14.57.

6-(2-chloro-4-methylphenyl)-8-methyl-2-(methylthio)pyrido[2,3-d]pyrimidin-7(8H)-one (32):

31 (24 mg, 0.11 mmol), (2-chloro-4-methylphenyl)boronic acid (28 mg, 0.16 mmol) and Pd(PPh$_3$)$_4$ (13 mg, 0.011 mmol) was taken in round bottom flask (rb) and purged with argon for 10 min DMF (1 mL) and CH$_3$CN (2 mL) were added to the above reactants and the reaction mixture was purged again for 10 min Following purging 1M Na$_2$CO$_3$ (23 mg, 0.21 mmol) (220 μL) solution was added drop wise and started heating at 90° C. for 5 h. After completion, the reaction mixture was cooled to rt and solvent was evaporated. The residue was partitioned between water and EtOAc, filtered and concentrated to get a crude mixture which was purified by column chromatography using silica gel (10% EtOAc/DCM) to get 32 (20 mg, 57%) as white solid. $^1$H NMR (400 MHz, CDCl$_3$) δ (ppm) 8.64 (s, 1H), 7.64 (s, 1H), 7.31-7.23 (m, 2H), 7.14 (d, J=7.6 Hz, 1H), 3.82 (s, 3H), 2.66 (s, 3H), 2.38 (s, 3H). $^{13}$C NMR (400 MHz, CDCl$_3$) δ (ppm) 173.28, 161.96, 156.34, 154.34, 140.33, 134.85, 133.32, 131.64, 131.19, 130.38, 127.67, 109.44, 28.55, 21.15, 14.61.

6-(2-chloro-4-methylphenyl)-8-methyl-2-(methylsulfonyl)pyrido[2,3-d]pyrimidin-7(8H)-one (33):

Yield 68%, white solid; $^1$H NMR (400 MHz, CDCl$_3$) δ (ppm) 8.99 (s, 1H), 7.80 (s, 1H), 7.34 (s, 1H), 7.27-7.24 (m, 1H), 7.17 (d, J=8.4 Hz, 1H), 3.89 (s, 3H), 3.44 (s, 3H), 2.41 (s, 3H). $^{13}$C NMR (400 MHz, CDCl$_3$) δ (ppm) 164.45, 161.33, 157.07, 155.10, 141.20, 136.58, 133.58, 133.10, 130.92, 130.60, 130.56, 127.83, 115.12, 39.35, 29.34, 21.22.

6-(2-chloro-4-methylphenyl)-8-methyl-2-((3-9 (methylsulfonyl)phenyl)amino)pyridol2,3-dlpyrimidin-7(8H)-one (34) UH15_20:

Yield 75%, white solid; $^1$H NMR (400 MHz, DMSO-d6) δ (ppm) 10.60 (s, 1H), 8.88 (s, 1H), 8.76 (s, 1H), 7.96 (d, J=8.8 Hz, 1H), 7.87 (s, 1H), 7.64-7.56 (m, 2H), 7.38 (s, 1H), 7.28 (d, J=8 Hz, 1H), 7.21 (d, J=7.7 Hz, 1H), 3.68 (s, 3H), 3.22 (s, 3H), 2.35 (s, 3H). HRMS m/z calculated for C$_{22}$H$_{19}$ClN$_4$O$_3$S [M+H]$^+$: 455.0939; found 455.0944; purity 99.6% (t$_R$ 23.51 min).

Example 2

Evaluation

Receptor interacting protein kinase 2 (RIPK2) enzyme assay:

Recombinant RIPK2 protein (20 ng per reaction) is diluted in the reaction buffer consisting of 40 mM Tris (pH 7.5); 20 mM MgCl$_2$; 0.1 mg/mL BSA; 50 pM DTT. Diluted protein is added to low volume white 384 well plates (2 μL/well). Inhibitors are diluted in reaction buffer (final 25% DMSO), 1 μL is added to each well and incubated 5 min at room temperature. Reactions are initiated by the addition of 2 μL of 100 μM ATP and 1 mg/mL RS repeat peptide (SignalChem) in the reaction buffer. Plates are sealed with plastic coverslips and incubated at room temperature for 2 h. Reactions are stopped by the addition of 5 μL of ADP-Glo reagent (Promega) and ADP generation reaction is performed for 40 min at room temperature. Luminescence signal is generated by the addition of 10 μL of Kinase detection reagent (Promega) for 30 mM at room temperature. Luminescence signals are determined using appropriate luminescence plate-reader (typical integration time 0.3-1 sec). To calculate percent inhibition, average background signal is subtracted from test well and maximal signal wells. Inhibition, %=(1- (test signal/maximal signal))*100. The percent inhibition at a specified concentration is determined or IC$_{50}$ values are calculated based on a dose range of inhibitor concentrations using non-linear regression in GraphPad Prism software.

Activin-like kinase 2 (ALK2) enzyme assay:

Enzyme inhibitory activity was evaluated in a standard kinase enzyme assay by incubating human ALK2 with the protein substrate casein (1 mg/mL) and γ-$^{33}$ATP (10 [M) in the presence of various concentrations of test compounds (10 nM-100 μM). After 30 min the amount of $^{33}$P-casein was determined. A plot of inhibitor concentration verses % activity was constructed and from this plot an IC$_{50}$ value was determined.

NOD2 signaling assay:

HEK-Blue cells expressing human NOD2 and NFkB-SAEP reporter (Invivogen) are seeded into 96 well clear plates at 7.5×10$^3$ cells per well in 100 μL of DMEM media supplemented with 10% FBS and 1% antibiotic-antimycotic mix. Cells are allowed to attach for 48 h in 5% CO$_2$ tissue culture incubator at 37° C. On the morning of the experiment, media in the wells is replaced with 100 μL of HEK-Blue detection media (Invivogen). Cells are treated with the inhibitors, diluted in DMSO (0.5 μL per well) for 15 min in 5% CO$_2$ tissue culture incubator at 37° C. After that, cells are stimulated by the addition of 1 ng/well L18-MDP (Invivogen). Cells are incubated in 5% CO$_2$ tissue culture incubator at 37° C. for 8 h and absorbance, corresponding to the SEAP in the media, is determined in Wallac3V plate reader (Perkin Elmer). Inhibition, %=(1-((sample signal-unstimulated and DMSO treated cells)/ (L18-MDP stimulated and DMSO treated cells-unstimulated and DMSO treated cells)))*100. IC$_{50}$ values are calculated based on a dose range of inhibitor concentrations using non-linear regression in GraphPad Prism software.

Inhibition of RIPK2 and ALK2 enzyme activities and NOD2 cellular signaling by compounds:

Prepared compounds were evaluated for their ability to inhibit RIPK2 and ALK2 enzyme activities and NOD2 cellular signaling using the methods described above. The percent inhibition at a specified concentration or IC$_{50}$ values for inhibition of RIPK2 enzyme and NOD2 cellular signaling by the compounds are shown in Table 1. IC$_{50}$ values for inhibition of ALK2 enzyme activity by the compounds are also shown in Table 1.

TABLE 1

| | EC$_{50}$ | | |
| --- | --- | --- | --- |
| | Enzyme (nM) | | HEK Blue (μM) |
| Compound | RIPK2 | ALK2 | RIPK2 |
| UH15 | 13.1 | 21.3 | 0.037 |
| UH15_1 | 16.6 | NI | 0.16 |
| UH15_2 | 11.7 | 61.5 | 0.004 |
| UH15_3 | 8.7 | 284 | 0.012 |
| UH15_4 | 53% at 33 nM | 3.7 | 0.015 |
| UH15_5 | 55% at 33 nM | 18.2 | 0.27 |
| UH15_6 | 32% at 33 nM | 17.8 | 0.008 |
| UH15_7 | 21.0 | 8.0 | 0.009 |
| UH15_8 | 13.1 | 2945 | 0.95 |
| UH15_9 | 95.5 | NI | 1.98 |
| UH15_10 | 5.5 | 9 | 0.0028 |
| UH15_11 | 6.6 | 972 | 0.022 |
| UH15-12 | 14.6 | 136 | 0.136 |
| UH15_13 | 10.7 | NI | NI |
| UH15-14 | 67.6 | NI | NI |
| UH15_15 | 8.0 | 2516 | 0.02 |
| UH15_16 | 27.0 | NI | 1.05 |
| UH15_17 | 34.6 | NI | 1.23 |
| UH15_18 | 16.4 | NI | 0.183 |
| UH15_19 | 22.4 | | 0.731 |
| UH15_20 | 15.7 | | 0.484 |
| UH15_21 | 16.0 | 24800 | |
| UH15_22 | 25.0 | 13 | 0.005 |
| UH15_25 | | | 0.055 |
| UH15_26 | 25.1 | 96 | 0.0055 |
| UH15_27 | 21.0 | | 0.123 |
| UH15_29 | 11.5 | NI | NI |
| UH15_30 | 21.3 | NI | 0.627 |
| UH15_32 | 27.3 | NI | 0.406 |
| UH15_33 | 21.6 | 226 | 0.0002 |
| UH15_34 | 35.2 | 1100 | 0.034 |
| UH15_35 | 87.4 | | 0.949 |
| UH15PN1 | 22.1 | 326 | 0.168 |
| UH15PN2 | 30.2 | NI | 0.353 |
| UH15PN3 | 29.6 | 8420 | |
| UH15PN5 | 41.5 | | 1.96 |
| UH15PN6 | 25.0 | | 0.45 |

NI: no inhibition observed

What is claimed is:

1. A compound demonstrating protein kinase inhibitory activity and having a structure of:

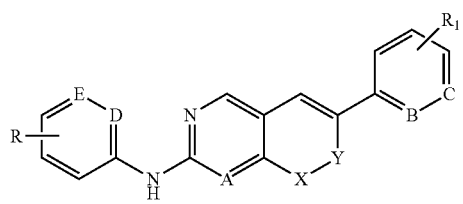

wherein R is SO$_2$Me at one available ring position, wherein Me is methyl;
A is N;
D is N or CH;
E is N, CH, or C—R;
B and C are independently N, CH, or C—Cl;
R$_1$ is H, or R$_1$ is Cl, F, OCH$_3$, C(CH$_3$)$_3$, or OH at one available ring position; and
X—Y is

wherein R$_2$ is H, alkyl, alkylhydroxyl, alkylalkoxyl, or alkylaryl.

2. The compound of claim 1, wherein R$_2$ is methyl, ethyl, isobutyl, 2-hydroxyethyl, 2-methoxyethyl, benzyl, or phenethyl.

3. A pharmaceutical composition comprising a therapeutically effective amount of the compound of claim 1 and a pharmaceutically acceptable excipient, adjuvant, carrier, buffer, stabilizer, or mixture thereof.

4. A compound demonstrating protein kinase inhibitory activity, wherein the compound has a structure of:

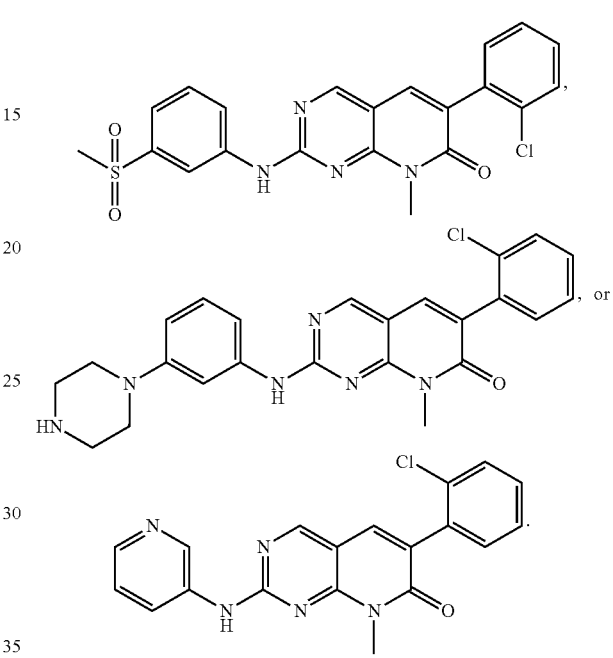

5. A pharmaceutical composition comprising a therapeutically effective amount of the compound of claim 4 and a pharmaceutically acceptable excipient, adjuvant, carrier, buffer, stabilizer, or mixture thereof.

6. A compound demonstrating protein kinase inhibitory activity and having a structure of:

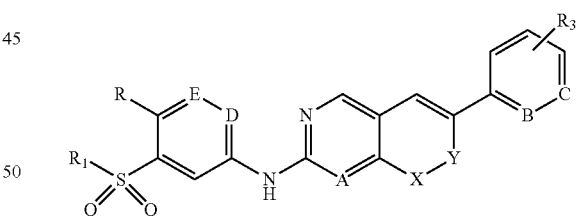

wherein R is H,

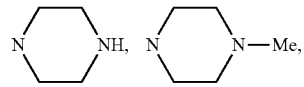

SO$_2$Me,

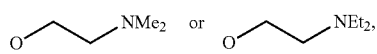

wherein Me is methyl and Et is ethyl;
R$_1$ is any alkyl or aryl group;
A is N;

D is N or CH;
E is N, CH, or C—R;
B and C are independently N, CH, or C—Cl;
$R_3$ is H, or $R_3$ is Cl, F, $OCH_3$, $C(CH_3)_3$, or OH at one available ring position; and
X—Y are

wherein $R_2$ is H, alkyl, alkylhydroxyl, alkylalkoxyl, or alkylaryl.

7. The compound of claim 6, wherein $R_1$ is methyl, ethyl, or propyl.

8. The compound of claim 6, wherein $R_2$ is methyl, ethyl, isobutyl, 2-hydroxyethyl, 2-methoxyethyl, benzyl, or phenethyl.

9. A pharmaceutical composition comprising a therapeutically effective amount of the compound of claim 6 and a pharmaceutically acceptable excipient, adjuvant, carrier, buffer, stabilizer, or mixture thereof.

* * * * *

UNITED STATES PATENT AND TRADEMARK OFFICE
CERTIFICATE OF CORRECTION

PATENT NO. : 11,174,255 B2
APPLICATION NO. : 16/613003
DATED : November 12, 2019
INVENTOR(S) : Gregory Cuny et al.

It is certified that error appears in the above-identified patent and that said Letters Patent is hereby corrected as shown below:

In the Specification

1. In Column 1, Line 9, delete ""Pyridol[2,3-d]pyrimidin-7-ones" and insert -- "Pyrido[2,3-d]pyrimidin-7-ones --, therefor.

2. In Column 7, Line 30, delete "CDCl$_{13}$)" and insert -- CDCl$_3$) --, therefor.

3. In Column 7, Lines 49-50, delete "6-(2-chlorophenyl)-8-methyl-2-(methylthio)pyridol2,3-dlpyrimidin-7(8H)-imine (9b):" and insert -- 6-(2-chlorophenyl)-8-methyl-2-(methylthio)pyrido[2,3-d]pyrimidin-7(8H)-imine (9b): --, therefor.

4. In Column 7, Lines 54-55, delete "8-methyl-2-(methylthio)-6-phenylpyridol2,3-dlpyrimidin-7(8H)-imine (9c):" and insert -- 8-methyl-2-(methylthio)-6-phenylpyrido[2,3-d]pyrimidin-7(8H)-imine (9c): --, therefor.

5. In Column 10, Line 6, delete "(10" and insert -- (10 μl, --, therefor.

6. In Column 11, Lines 4-5, delete "6-(2,6-dichlorophenyl)-8-(4-(methylsulfonyl)benzyl)-2-(methylthio)pyridol2,3-dlpyrimidin-7(8H)-one (13r):" and insert -- 6-(2,6-dichlorophenyl)-8-(4-(methylsulfonyl)benzyl)-2-(methylthio)pyrido[2,3-d]pyrimidin-7(8H)-one (13r): --, therefor.

7. In Column 11, Lines 10-11, delete "6-(4-methoxyphenyl)-8-methyl-2-(methylthio)pyridol2,3-dlpyrimidin-7(8H)-one (13s):" and insert -- 6-(4-methoxyphenyl)-8-methyl-2-(methylthio)pyrido[2,3-d]pyrimidin-7(8H)-one (13s): --, therefor.

8. In Column 11, Line 27, delete "(methylthio)pyridol2,3-dlpyrimidin-7(8H)-one" and insert -- (methylthio)pyrido[2,3-d]pyrimidin-7(8H)-one --, therefor.

9. In Column 12, Line 30, delete "DEPT 6" and insert -- DEPT δ --, therefor.

Signed and Sealed this
Seventeenth Day of May, 2022

*Katherine Kelly Vidal*

Katherine Kelly Vidal
*Director of the United States Patent and Trademark Office*

CERTIFICATE OF CORRECTION (continued)
U.S. Pat. No. 11,174,255 B2

10. In Column 13, Line 6, delete "(140):" and insert -- (14o): --, therefor.

11. In Column 15, Lines 19-21, delete "6-(2,4-dichlorophenyl)-2-44-(2-(diethylamino)ethoxy)phenyl) amino)-8-methylpyridol2,3-dlpyrimidin-7(8H)-one (17a) UH15_1:" and insert -- 6-(2,4-dichlorophenyl)-2-((4-(2-(diethylamino)ethoxy)phenyl)amino)-8-methylpyrido[2,3-d]pyrimidin-7(8H)-one (17a) UH15_1: --, therefor.

12. In Column 15, Line 30, delete "[M+H]$^{30}$;" and insert -- [M+H]$^+$: --, therefor.

13. In Column 15, Lines 32-34, delete "6-(2-chlorophenyl)-2-44-(2-(diethylamino)ethoxy)phenyl) amino)-8-methylpyridol2,3-dlpyrimidin-7(8H)-one (17b) UH15_2:" and insert -- 6-(2-chlorophenyl)-2-((4-(2-(diethylamino)ethoxy)phenyl)amino)-8-methylpyrido[2,3-d]pyrimidin-7(8H)-one (17b) UH15_2: --, therefor.

14. In Column 15, Line 46-47, delete "2-44-(2-(diethylamino)ethoxy)phenyl)amino)-8-methyl-6-phenylpyrido[2,3-d]pyrimidin-7(8H)-one (17c) UH15__3:" and insert -- 2-((4-(2-(diethylamino) ethoxy)phenyl)amino)-8-methyl-6-phenylpyrido[2,3-d]pyrimidin-7(8H)-one (17c) UH15_3: --, therefor.

15. In Column 15, Lines 59-60, delete "2-44-(2-(diethylamino)ethoxy)phenyl)amino)-8-ethyl-6-phenylpyrido[2,3-d]pyrimidin-7(8H)-one (17i) UH15_4:" and insert -- 2-((4-(2-(diethylamino) ethoxy)phenyl)amino)-8-ethyl-6-phenylpyrido[2,3-d]pyrimidin-7(8H)-one (17i) UH15_4: --, therefor.

16. In Column 16, Lines 4-6, delete "2-44-(2-(diethylamino)ethoxy)phenyl)amino)-8-(2-hydroxyethyl)-6-phenylpyrido[2,3-d]pyrimidin-7(8H)-one (17j) UH15_5:" and insert -- 2-((4-(2-(diethylamino)ethoxy)phenyl)amino)-8-(2-hydroxyethyl)-6-phenylpyrido[2,3-d]pyrimidin-7(8H)-one (17j) UH15_5: --, therefor.

17. In Column 16, Lines 17-19, delete "6-(2,6-dichlorophenyl)-2-44-(2-(diethylamino)ethoxy) phenyl)amino)-8-(2-methoxyethyl)pyrido[2,3-d]pyrimidin-7(8H)-one (17k) UH15_6:" and insert -- 6-(2,6-dichlorophenyl)-2-((4-(2-(diethylamino)ethoxy)phenyl)amino)-8-(2-methoxyethyl)pyrido[2,3-d]pyrimidin-7(8H)-one (17k) UH15_6: --, therefor.

18. In Column 16, Lines 32-34, delete "8-benzyl-6-(2,6-dichlorophenyl)-2-44-(2-(diethylamino) ethoxy)phenyeamino)pyrido[2,3-d]pyrimidin-7(8H)-one (171) UH15_7:" and insert -- 8-benzyl-6-(2,6-dichlorophenyl)-2-((4-(2-(diethylamino)ethoxy)phenyl)amino)pyrido[2,3-d]pyrimidin-7(8H)-one (17l) UH15_7: --, therefor.

19. In Column 16, Lines 46-48, delete "6-(4-chlorophenyl)-2-44-(2-(diethylamino)ethoxy) phenyl)amino)-8-methylpyrido[2,3-d]pyrimidin-7(8H)-one (17d) UH15_8:" and insert -- 6-(4-chlorophenyl)-2-((4-(2-(diethylamino)ethoxy)phenyl)amino)-8-methylpyrido[2,3-d]pyrimidin-7(8H)-one (17d) UH15_8: --, therefor.

20. In Column 17, Lines 9-11, delete "6-(2,6-dichlorophenyl)-2-44-(2-(diethylamino)ethoxy) phenyl)amino)-8-isobutylpyrido[2,3-d]pyrimidin-7(8H)-one (17m) UH15_10:" and insert -- 6-(2,6-

CERTIFICATE OF CORRECTION (continued)
U.S. Pat. No. 11,174,255 B2 dichlorophenyl)-2-((4-(2-(diethylamino)ethoxy)phenyl)amino)-8-isobutylpyrido[2,3-d]pyrimidin-7(8H)-one (17m) UH15_10: --, therefor.

21. In Column 17, Lines 51-53, delete "6-(4-chlorophenyl)-8-methyl-2-43-(methylsulfonyl) phenyl)amino)pyrido12,3-dlpyrimidin-7(8H)-one (17d*) UH15-13:" and insert -- 6-(4-chlorophenyl)-8-methyl-2-((3-(methylsulfonyl)phenyl)amino)pyrido[2,3-d]pyrimidin-7(8H)-one (17d*) UH15_13: --, therefor.

22. In Column 17, Lines 61-63, delete "6-(4-chlorophenyl)-8-isobutyl-2-43-(methylsulfonyl)phenyl) amino)pyrido[12,3-d]pyrimidin-7(8H)-one (17n) UH15_14:" and insert -- 6-(4-chlorophenyl)-8-isobutyl-2-((3-(methylsulfonyl)phenyl)amino)pyrido[2,3-d]pyrimidin-7(8H)-one (17n) UH15_14: --, therefor.

23. In Column 18, Lines 6-9, delete "6-(2-chlorophenyl)-8-methyl-2-43-(methylsulfonyl)phenyl) amino)pyrido12,3-dlpyrimidin-7(8H)-one (17b*) UH15_15:" and insert -- 6-(2-chlorophenyl)-8-methyl-2-((3-(methylsulfonyl)phenyl)amino)pyrido[2,3-d]pyrimidin-7(8H)-one (17b*) UH15_15: --, therefor.

24. In Column 18, Lines 17-19, delete "6-(2,4-dichlorophenyl)-8-methyl-24(3-(methylsulfonyl) phenyl)amino)pyrido12,3-dlpyrimidin-7(8H)-one (17a*) UH15_16:" and insert -- 6-(2,4-dichlorophenyl)-8-methyl-2-((3-(methylsulfonyl)phenyl)amino)pyrido[2,3-d]pyrimidin-7(8H)-one (17a*) UH15_16: --, therefor.

25. In Column 18, Lines 31-33, delete "6-(2,3-dichlorophenyl)-8-methyl-24(3-(methylsulfonyl) phenyl)amino)pyrido2,3-dlpyrimidin-7(8H)-one (17g) UH15_17:" and insert -- 6-(2,3-dichlorophenyl)-8-methyl-2-((3-(methylsulfonyl)phenyl)amino)pyrido[2,3-d]pyrimidin-7(8H)-one (17g) UH15_17: --, therefor.

26. In Column 18, Line 40, delete "6" and insert -- δ --, therefor.

27. In Column 18, Line 44, delete "[M+H]$^{30}$ :" and insert -- [M+H]$^{+}$ : --, therefor.

28. In Column 18, Lines 46-48, delete "6-(2-chloro-4-fluorophenyl)-8-methyl-24(3-(methylsulfonyl)phenyl)amino)pyrido2,3-dlpyrimidin-7(8H)-one (17h) UH15_18:" and insert -- 6-(2-chloro-4-fluorophenyl)-8-methyl-2-((3-(methylsulfonyl)phenyl)amino)pyrido[2,3-d]pyrimidin-7(8H)-one (17h) UH15_18: --, therefor.

29. In Column 19, Lines 16-19, delete "24(4-(2-(diethylamino)ethoxy)phenyl)amino)-6-(4-hydroxyphenyl)-8-methylpyrido[2,3-d]pyrimidin-7(8H)-one (17p*) UH15_22:" and insert -- 2-((4-(2-(diethylamino)ethoxy)phenyl)amino)-6-(4-hydroxyphenyl)-8-methylpyrido[2,3-d]pyrimidin-7(8H)-one (17p*) UH15_22: --, therefor.

30. In Column 19, Lines 28-30, delete "6-(2,6-dichlorophenyl)-2-44-(2-(diethylamino)ethoxy) phenyl)amino)-8-(3-(methylsulfonyebenzyl)pyrido[2,3-d]pyrimidin-7(8H)-one (17q) UH15_26:" and insert -- 6-(2,6-dichlorophenyl)-2-((4-(2-(diethylamino)ethoxy)phenyl)amino)-8-(3-(methylsulfonyl)benzyl)pyrido[2,3-d]pyrimidin-7(8H)-one (17q) UH15_26: --, therefor.

31. In Column 19, Lines 38-40, delete "6-(2,6-dichlorophenyl)-2-44-(2-(diethylamino)ethoxy) phenyl)amino)-8-(4-(methylsulfonyebenzyl)pyrido[2,3-d]pyrimidin-7(8H)-one (17r) UH15_27:" and insert -- 6-(2,6-dichlorophenyl)-2-((4-(2-(diethylamino)ethoxy)phenyl)amino)-8-(4-(methylsulfonyl)benzyl)pyrido[2,3-d]pyrimidin-7(8H)-one (17r) UH15_27: --, therefor.

32. In Column 19, Lines 49-51, delete "6-(4-methoxyphenyl)-8-methyl-2-43-(methylsulfonyl) phenyl)amino)pyrido[2,3-d]pyrimidin-7(8H)-one (17s) UH15_29:" and insert -- 6-(4-methoxyphenyl)-8-methyl-2-((3-(methylsulfonyl)phenyl)amino)pyrido[2,3- -d]pyrimidin-7(8H)-one (17s) UH15_29: --, therefor.

33. In Column 19, Lines 59-61, delete "2-44-(2-(diethylamino)ethoxy)phenyl)amino)-6-(4-methoxyphenyl)-8-methylpyrido[2,3-d]pyrimidin-7(8H)-one (17s*) UH15_30:" and insert -- 2-((4-(2-(diethylamino)ethoxy)phenyl)amino)-6-(4-methoxyphenyl)-8-methylpyrido[2,3-d]pyrimidin-7(8H)-one (17s*) UH15_30: --, therefor.

34. In Column 20, Line 2, delete "$C_{27}H_3N_5O_3$" and insert -- $C_{27}H_{31}N_5O_3$ --, therefor.

35. In Column 20, Lines 58-59, delete "3-(2-chlorophenyl)-1-methyl-7-43-(methylsulfonyl)phenyl) amino)-1,6-naphthyridin-2(1H)-one (57) UH15_32:" and insert -- 3-(2-chlorophenyl)-1-methyl-7-((3-(methylsulfonyl)phenyl)amino)-1,6-naphthyridin-2(1H)-one (57) UH15_32: --, therefor.

36. In Column 23, Lines 57-59, delete "Tert-butyl 4-(3-43-(2-chlorophenyl)-1-methyl-2-oxo-1,2-dihydro-1,6-naphthyridin-7-yl)amino)phenyl)piperazine-l-carboxylate (60):" and insert -- Tert-butyl 4-(3-((3-(2-chlorophenyl)-1-methyl-2-oxo-1,2-dihydro-1,6-naphthyridin-7-yl)amino)phenyl) piperazine-1-carboxylate (60): --, therefor.

37. In Column 24, Lines 4-5, delete "3-(2-chlorophenyl)-1-methyl-7-43-(piperazin-l-yl)phenyl) amino)-1,6-naphthyridin-2(1H)-one (61) UH15_25:" and insert -- 3-(2-chlorophenyl)-1-methyl-7-((3-(piperazin-1-yl)phenyl)amino)-1,6-naphthyridin-2(1H)-one (61) UH15_25: --, therefor.

38. In Column 24, Lines 45-47, delete "Tert-butyl 4-(5-43-(2-chlorophenyl)-1-methyl-2-oxo-1,2-dihydro-1,6-naphthyridin-7-yl)amino)pyridin-3-yl)piperazine-1-carboxylate (71):" and insert -- Tert-butyl 4-(5-((3-(2-chlorophenyl)-1-methyl-2-oxo-1,2-dihydro-1,6-naphthyridin-7-yl)amino)pyridin-3-yl)piperazine-1-carboxylate (71): --, therefor.

39. In Column 24, Lines 59-61, delete "3-(2-chlorophenyl)-1-methyl-7-45-(piperazin-l-yl)pyridin-3-yl)amino)-1,6-naphthyridin-2(1H)-one (72) UH15_36:" and insert -- 3-(2-chlorophenyl)-1-methyl-7-((5-(piperazin-1-yl)pyridin-3-yl)amino)-1,6-naphthyridin-2(1H)-one (72) UH15_36: --, therefor.

40. In Column 25, Lines 13-14, delete "6-chloro-8-methyl-2-(methylthio)pyridol2,3-dlpyrimidin-7(8H)-one (31):" and insert -- 6-chloro-8-methyl-2-(methylthio)pyrido[2,3-d]pyrimidin-7(8H)-one (31): --, therefor.

41. In Column 25, Lines 58-60, delete "6-(2-chloro-4-methylphenyl)-8-methyl-2-((3-9 (methylsulfonyl)phenyl)amino)pyridol2,3-dlpyrimidin-7(8H)-one (34) UH15__20:" and insert -- 6-(2-chloro-4-methylphenyl)-8-methyl-2-((3-(methylsulfonyl)phenyl)amino)pyrido[2,3-d]pyrimidin-7(8H)-one (34) UH15_20: --, therefor.

42. In Column 26, Line 20, delete "30 mM" and insert -- 30 min --, therefor.